(12) United States Patent
Klimberg et al.

(10) Patent No.: US 7,709,529 B2
(45) Date of Patent: May 4, 2010

(54) TREATMENT OF CANCER WITH GLUTAMINE

(75) Inventors: V. Suzanne Klimberg, Little Rock, AR (US); Robert G. Petit, II, Langhorne, PA (US); Edward C. Shinal, Pennington, NJ (US)

(73) Assignee: Eisai Inc., Ridgefield Park, NJ (US)

( * ) Notice: Subject to any disclaimer, the term of this patent is extended or adjusted under 35 U.S.C. 154(b) by 389 days.

(21) Appl. No.: 10/633,402

(22) Filed: Aug. 1, 2003

(65) Prior Publication Data

US 2005/0090451 A1 Apr. 28, 2005

Related U.S. Application Data

(60) Provisional application No. 60/400,446, filed on Aug. 1, 2002.

(51) Int. Cl.
*A61K 31/195* (2006.01)
(52) U.S. Cl. ............... 514/561; 514/23; 514/53; 514/563
(58) Field of Classification Search .......... 514/563, 514/23, 53, 561
See application file for complete search history.

(56) References Cited

U.S. PATENT DOCUMENTS

| | | | |
|---|---|---|---|
| 2,283,817 A | 5/1942 | Martin et al. ............ 167/55 |
| 2,868,693 A | 1/1959 | Shive et al. ............ 167/55 |
| 3,058,942 A | 10/1962 | Kirkland et al. | |
| 4,647,459 A | 3/1987 | Peters et al. | |
| 4,671,953 A | 6/1987 | Stanley et al. | |
| 4,849,408 A | 7/1989 | Sommermeyer et al. | |
| 4,857,555 A | 8/1989 | Smith et al. ............ 514/563 |
| 4,983,595 A | 1/1991 | Benjamin et al. | |
| 5,039,704 A | 8/1991 | Smith et al. ............ 514/563 |
| 5,160,331 A | 11/1992 | Forester et al. | |
| 5,248,697 A | 9/1993 | Wilmore | |
| 5,366,723 A | 11/1994 | Tulok ............ 424/10 |
| 5,397,803 A | 3/1995 | Smith et al. ............ 514/563 |
| 5,438,042 A | 8/1995 | Schmidl et al. | |
| 5,438,075 A | 8/1995 | Skubitz et al. | |
| 5,484,602 A | 1/1996 | Stanley et al. | |
| 5,545,668 A | 8/1996 | Skubitz et al. ............ 514/561 |
| 5,607,975 A | 3/1997 | Smith et al. ............ 514/563 |
| 5,658,895 A | 8/1997 | Aoi et al. ............ 514/58 |
| 5,684,045 A | 11/1997 | Smith et al. ............ 514/563 |
| 5,726,146 A | 3/1998 | Almada et al. | |
| 5,744,166 A | 4/1998 | Illum | |
| 5,763,485 A | 6/1998 | Smith et al. ............ 514/563 |
| 5,792,753 A | 8/1998 | Falk et al. | |
| 5,817,695 A * | 10/1998 | Pellico ............ 514/558 |
| 5,849,335 A | 12/1998 | Ballevre et al. | |
| 5,891,467 A | 4/1999 | Willis | |
| 5,932,235 A | 8/1999 | Ninomiya et al. | |
| 5,985,850 A | 11/1999 | Falk et al. | |
| 6,102,254 A | 8/2000 | Ross | |
| 6,159,492 A | 12/2000 | Manzone et al. | |
| 6,166,083 A | 12/2000 | Barrett et al. | |
| 6,391,332 B1 | 5/2002 | Somerville et al. | |
| 6,479,068 B1 | 11/2002 | Sherratt et al. | |
| 6,666,811 B1 * | 12/2003 | Good ............ 600/8 |
| 6,734,170 B2 | 5/2004 | Petit et al. | |
| 7,041,651 B2 | 5/2006 | Petit, II et al. | |
| 2003/0099722 A1 | 5/2003 | Baxter | |
| 2004/0176319 A1 | 9/2004 | Petit et al. | |
| 2004/0265359 A1 | 12/2004 | Sacks et al. | |
| 2006/0069230 A1 | 3/2006 | Papisov | |

FOREIGN PATENT DOCUMENTS

| | | |
|---|---|---|
| CA | 2374003 | 11/2000 |
| EP | 0614659 | 9/1994 |
| EP | 0238553 B1 | 5/1997 |
| EP | 0845265 | 6/1998 |
| EP | 0873749 | 10/1998 |
| JP | 62-169730 | 7/1987 |
| JP | 62-283927 | 12/1987 |
| JP | 6-501000 | 1/1994 |
| JP | 06-192108 | 7/1994 |
| JP | 07-010743 | 1/1995 |
| JP | 09-187233 | 7/1997 |
| JP | 10-511637 | 11/1998 |
| WO | WO-8701589 A1 | 3/1987 |
| WO | WO-92/04895 A1 | 4/1992 |
| WO | WO-9608238 A1 | 3/1996 |
| WO | WO-9706813 A1 | 2/1997 |

(Continued)

OTHER PUBLICATIONS

Abcouwer, S F., et al., "Glutamine deprivation induces the expression of GADD45 and GADD153 primarily by mRNA stabilization", *Journal of Biological Chemistry*, 274(40), (Oct. 1, 1999),28645-28651.

(Continued)

*Primary Examiner*—James D Anderson
(74) *Attorney, Agent, or Firm*—Schwegman, Lundberg & Woessner, P.A.

(57) ABSTRACT

Provided are methods of treating cancer, and/or the side effects of cancer therapy, involving the administration of glutamine, optionally in combination with a carbohydrate carrier that enhances the absorption of glutamine.

18 Claims, 23 Drawing Sheets

FOREIGN PATENT DOCUMENTS

| WO | WO-97/14310 | | 4/1997 |
|---|---|---|---|
| WO | WO-9843643 A1 | | 10/1998 |
| WO | 00/69470 | * | 11/2000 |
| WO | WO-00/69470 A2 | | 11/2000 |

OTHER PUBLICATIONS

Anderson, P M., et al., "Effect of low-dose oral glutamine on painful stomatitis during bone marrow transplantation", *Bone Marrow Transplant*, 22 (4), (Aug. 1998),339-344.

Anderson, P., et al., "Oral glutamine reduces the duration and severity of stomatitis after cytotoxic cancer chemotherapy", *Cancer*, 83 (7), (Oct. 1, 1998),1433-1439.

Ayala, E., et al., "Effect of L-lysine monohydrochloride on cutaneous herpes simplex virus in the guinea pig", *Journal of Medical Virology*, 28(1), (May 1989), 16-20.

Baslow, M. H., et al., "Analysis of the nature of the metabolic lesions responsible for development of the observed clinical symptoms", *Journal of Molecular Neuroscience*, 9(2), (Oct. 1997),109-125.

Bines, J., et al., "Reducing parenteral requirement in children with short bowel syndrome: impact of an amino acid-based complete infant formula", *Journal of Pediatric Gastroenterology & Nutrition*, 26(2), (Feb. 1998),123-128.

Cao, Y., et al., "Effect of 7,12-dimethylbenz[a]anthracene (DMBA) on gut glutathione metabolism", *Journal of Surgical Research*, 100(1), (Sep. 2001),135-140.

Cao, Y., et al., "Glutamine enhances gut glutathione production", *Jpen: Journal of Parenteral & Enteral Nutrition*, 22(4), (Jul.-Aug. 1998),224-227.

Cardona, P., "Administration of glutamine and its dipeptides in parenteral nutrition. Which patients are candidates?", *Nutricion Hospitalaria*, 13(1), (Jan.-Feb. 1998),8-20.

Fahr, M., et al., "Vars Research Award. Glutamine enhances immunoregulation of tumor growth.", *Jpen: Journal of Parenteral & Enteral Nutrition*, 18(6), Nov.-Dec. 1994 ,471-476.

Feng, Zuliang, et al., "Glutamine prevents DMBA-induced breast cancer growth", *Surgical Forum*, 47(0), (1996),524-526.

Guerrant, R L., et al., "Cryptosporidiosis: an emerging, highly infectious threat", *Emerging Infectious Diseases*, 3(1), (Jan.-Mar. 1997),51-57.

Juhl, J. H., et al., "Fibromyalgia and the serotonin pathway", *Alternative Medicine Review*, 3(5), (Oct. 1998),367-375.

Karinch, A M., et al., "Glutamine metabolism in sepsis and infection", *Journal of Nutrition*, 131(9 Suppl), (Sep. 2001),2535S-2577S.

Klimberg, V S., et al., "Glutamine facilitates chemotherapy while reducing toxicity", *Jpen: Journal of Parenteral & Enteral Nutrition*, 16(6 Suppl), (Nov.-Dec. 1992),83S-87S.

Klimberg, V S., et al., "Glutamine suppresses PGE2 synthesis and breast cancer growth", *Journal of Surgical Research*, 63(1), (Jun. 1996),293-297.

Klimberg, V S., et al., "Honorary Lectureship. Glutamine, cancer, and its therapy", *American Journal of Surgery*, 172(5), (Nov. 1996),418-424.

Labow, B I., et al., "Glutamine", *World Journal of Surgery*, 24(12), (Dec. 2000),1503-1513.

Mastroiacovo, P., et al., "Amino acids for dialysis patients", *Clinical Therapeutics*, 15(4), (Jul.-Aug. 1993),698-704.

Neu, J, et al., "Enteral glutamine supplementation for very low birth weight infants decreases morbidity", *Journal of Pediatrics*, 131(5), (Nov. 1997),691-699.

Obrador, E, et al., "Glutamine potentiates TNF-alpha-induced tumor cytotoxicity", *Free Radical Biology & Medicine*, 31(5), (Sep. 1, 2001),642-650.

Piccirillo, N, et al., "Glutamine-enriched parenteral nutrition after autologous peripheral blood stem cell transplantation: effects on immune reconstitution and mucositis", *Haematologica*, 88(2), (Feb. 2003),192-200.

Rouse, K, et al., "Glutamine enhances selectivity of chemotherapy through changes in glutathione metabolism", *Annals of Surgery*, 221(4), (Apr. 1995),420-426.

Skubitz, K M., et al., "Oral glutamine to prevent chemotherapy induced stomatitis: a pilot study", *Journal of Laboratory & Clinical Medicine*, 127(2), (Feb. 1996),223-228.

Tsai, G, et al., "D-serine added to antipsychotics for the treatment of schizophrenia", *Biological Psychiatry*, 44(11), (Dec. 1, 1998),1081-1089.

Wu, G, et al., "Dietary glutamine supplementation prevents jejunal atrophy in weaned pigs", *Journal of Nutrition*, 126(10) (Oct. 1996),2578-2584.

Yaqoob, P., et al., "Cytokine production by human peripheral blood mononuclear cells: differential senstivity to glutamine availability", *Cytokine*, 10(10), (Oct. 1998),790-794.

Alverdy, J C., "Effects of Glutamine-Supplemented Diets on Immunology of the Gut", *Journal of Parenteral & Enteral Nutrition*, 14(4) (Supp), (1990),109S-113S.

Alverdy, J C., "Parenteral Nutrition Results in Bacterial Translocation from the Gut and Death Following Chemotherapy", *14th Clinical Congress Abstracts*, 14 (1)(Supp), (1990), p. 8S.

American College of Physicians, "Parenteral Nutrition in Patients Receiving Cancer Chemotherapy", *Annuals of Internal Medicine*, 110(9), (1989), 734-736.

Brown, M G., "Glutamine-enhanced Enteral Diet Improves Nitrogen Balance Without Increasing Portal Ammonia", *British Journal of Surgery*, 78(11), (1991),1305-1306.

Burke, D J., "Effect of Route of Glutamine Administration GM Mortality Following Experimental Enterocolitis", *14th Clinical Congress Abstracts*, 14(1) (Supp), (1991),1 Page.

Burke, D. J., "Glutamine-Supplemented Total Parenteral Nutrition Improves Gut Immune Function", *Archives of Surgery*, 124(12), (1989),1396-9.

Dechelotte, P., "Absorption and Metabolic Effects of Enterally Administered Glutamine in Humans", *Journal of Physiology*, 260(5)(Pt 1), (1991),G677-G682.

Deferrari, G., "Splanchnic Exchange of Amino Acids After Amino Acid Ingestion in Patients with Chronic Renal Insufficiency", *American Journal of Clinical Nutrition*, 48(1), (1988),72-83.

Evans, M. A., "Intestinal Fuels: Glutamine, Short-Chain Fatty Acids, and Dietary Fiber", *Journal of the American Dietetic Association*, 92(10), (1992),1239-1246.

Fischer, J. E., "Adjuvant Parenteral Nutrition in the Patient with Cancer", *Surgery*, 96(3), (1984),578-580.

Fischer, J. E., "Total Parenteral Nutrition, Glutamine, and Tumor Growth", *Jpen: Journal of Parenteral & Enteral Nutrition*, 14(4) (Supp), (1990),86S-88S.

Fong, Y. M., "Total Parenteral Nutrition and Bowel Rest Modify the Metabolic Response to Endotoxin in Humans", *Annals of Surgery*, 210(4), (1989),449-457.

Fox, A. D., "Effect of a Glutamine-Supplemented Enteral Diet on Methotrexate-Induced Enterocolitis", *Journal of Parenteral & Enteral Nutrition*. 12(4), (1988),325-331.

Fox, A. D., "Reduction of the Severity of Enterocolitis by Glutamine-Supplemented Enteral Diets", *Surgical Forum*, 38, (1987),43-44.

Jacobs, D. O., "Combined Effects of Glutamine and Epidermal Growth Factor on the Rat Intestine", *Surgery*, 104(2), (1988),358-364.

Jacobs, D. O., "Disparate Effects Of 5-Fluorouracil On The Ileum And Colon Of Enterally Fed Rats With Protection By Dietary Glutamine", *Surgical Forum*, 38, (1987),45-46.

Klimberg, V. S., "Oral Glutamine Accelerates Healing of the Small Intestine and Improves Outcome After Whole Abdominal Radiation", *Archives of Surgery*, 125(8), (1990),1040-1045.

Klimberg, V. S., "Prophylactic Glutamine Protects the Intestinal Mucosa from Radiation Injury", *Cancer*, 66(1), (1990),62-68.

Moore, F. A., "TEN Versus TPN Following Major Abdominal Trauma—Reduced Septic Morbidity", *The Journal of Trauma*, 29(7), (1989),916-923.

O'Dwyer, S. T., "5-Fluorouracil Toxicity on Small Intestinal Mucosa But Not White Blood Cells is Decreased by Glutamine", *Clinical Research*, 35(3), (1987),p. 369A.

O'Dwyer, S. T., et al., "Chapter 28—New Fuels for the Gut", *In: Clinical Nutrition—Enteral and Tube Feeding*, 2nd Edition, Rombeau. J. L., et al., editors,. Rombeau, W. B. Saunders Company, (1990),540-555.

Parry-Billings, M., "Does Glutamine Contribute to Immunosuppression After Major Burns?", *The Lancet*, 336(8714), (1990),523-525.

Rombeau, J. L., "A Review of the Effects of Glutamine-Enriched Diets on Experimentally Induced Enterocolitis", *Journal of Parenteral & Enteral Nutrition*, 14(4) (Supp), (1990),100S-105S.

Schloerb, P. R., et al., "Total Parenteral Nutrition With Glutamine in Bone Marrow Transplantation and Other Clinical Applications (A Randomized, Double-Blind Study)", *Journal of Parenteral and Enteral Nutrition*, 17,5, (1993),407-413.

Shou, J., "Dietary Manipulation of Methotrexate-Induced Enterocolitis", *Journal of Parenteral & Enteral Nutrition*, 15(3), (1991),307-312.

Smith, R. J., "Glutamine Nutrition and Requirements", *Journal of Parenteral & Enteral Nutrition*, 14(4) (Supp), (1990),94S-99S.

Souba, W. W., "Glutamine Nutrition in the Management of Radiation Enteritis", *Journal of Parenteral & Enteral Nutrition*, 14(4) (Supp), (1990),106S-108S.

Souba, W. W., "Glutamine Nutrition: Theoretical Considerations and Therapeutic Impact", *Journal of Parenteral & Enteral Nutrition*, 14(5) (Supp), (1990),237S-243S.

Souba, W. W., "Intestinal Consumption of Intravenously Administered Fuels", *Journal of Parenteral & Enteral Nutrition*, 9(1), (1985),18-22.

Souba, W. W., "Oral Glutamine Reduces Bacterial Translocation Following Abdominal R.adiation", *Journal of Surgical Research*, 48(1), (1990),1-5.

Souba, W. W., "The Gut as a Nitrogen-Processing Organ in the Metabolic Response to Critical Illness", *Nutrition Support Services*, 8, (1988),15-22.

Steiger, E., "Effects of Nutrition on Tumor Growth and Tolerance to Chemotherapy", *Journal of Surgical Research*, 18(4), (1975),455-66.

Van Zaanen, H. C. T., et al., "Parenteral Glutamine Dipeptide Supplementation Does Not Ameliorate Chemotherapy-Induced Toxicity", *Cancer*, 74(10), (1994),2879-2884.

Vanderhoof, J. A., "Effects of Oral Supplementation of Glutamine on Small Intestinal Mucosal Mass Following Resection", *Journal of the American College of Nutrition*, 11(2), (1992),223-227.

Wells, C. L., "The Effect of Dietary Glutamine and Dietary RNA on Ileal Flora, Ileal Histology, and Bacterial Translocation in Mice", *Nutrition*, 6(1) (1990),70-83.

Windmueller, H. G., "Glutamine Utilization by the Small Intestine", *Advances in Enzymology & Related Areas of Molecular Biology*, 53, (1982),201-37.

Windmueller, H. G., "Intestinal Metabolism of Glutamine and Glutamate from the Lumen as Compared to Glutamine from Blood", *Archives of Biochemistry & Biophysics*, 171(2), (1975),662-672.

Windmueller, H. G., "Respiratory Fuels and Nitrogen Metabolism In Vivo in Small Intestine of Fed Rats. Quantitative importance of glutamine, glutamate, and aspartate", *Journal of Biological Chemistry*. 255(1), (1980),107-112.

Ziegler, T. R., "Clinical and Metabolic Efficacy of Glutamine-Supplemented Parenteral Nutrition After Bone Marrow Transplantation. A Randomized, Double-Blind, Controlled Study", *Annals of Internal Medicine*, 116(10), (1992),821-828.

Ziegler, T. R., "Safety and Metabolic Effects of L-Glutamine Administration in Humans", *Journal of Parenteral & Enteral Nutrition*, 14(4 Suppl), (1990), 137S-146S.

"International Search Report, for Application No. PCT/US03/23987, date mailed Apr. 28, 2005", 7 Pages.

"Myths About Radiation Therapy", breastcancer.org, http://www.breastcancer.org/cmn_myt_radMyh_pf.html, (Observed Jun. 30, 2005), 3 Pages.

"Side Effects of Radiation Therapy", CancerCansultants.com, http://patient.cancerconsultants.com/print.aspx?id=23109, (Observed Jun. 30, 2005), 6 pages.

Culliford, S. J., et al., "Activation of a Novel Organic Solute Transpoeter in Mammalian Red Blood Cells", *Journal of Physiology*, 489, (1995), 755-65.

Krishnamurthy, Rajesh, et al., "Mammographic Finding after Breast Conservation Therapy", *RadioGraphics 1999, 19 Breast Imaging*, (1999), S53-S62.

Medina, Miguel A., "Glutamine and Cancer", *J. Nutr.*, 131, (2001), 2539S-2542S.

Spilkervet, F. K., et al., "Effect of chlorhexidine rinsing on the oropharyngeal ecology in patients with head and neck cancer who have irradiation mucositis", *Oral Surg Oral Med Oral Pathol*, vol. 67 No. 2 (1989), 154-161.

Steenge, G. R., et al., "Stimulatory Effect of Insulin on Creatine Accumulation in Human Skeletal Muscle", *American Journal of Physiology*, 275, (Dec. 1998), E974-E979.

"Parent Nutrition in Patients Receiving Cancer Chemotherapy", *American College of Physicians*, A position paper in 1989 American College Physicians,(1989),734.

Bozzetti, F., et al., "Glutamine supplementation in cancer patients receiving chemotherapy: a double-blind randomized study", *Nutrition*, 13(7-8), (Jul.-Aug. 1997), 748-751.

"Definition of "Endothelium"", *Stedman's Medical Dictionary 27th Edition*, 2000, Williams & Wilkins, (2000), 3 pgs.

"Definition of "Epithelium"", *Stedman's Medical Dictionary 27th Edition*, 2000, Williams & Wilkins, (2000), 3pgs.

DARISIMALL.COM, "Web Printout of Ora-Plus product Description", [Online] [retrieved on Dec. 6, 2007]. Retrieved from the Internet: <URL: http://store.darisimall.com/631580.html>, 1 pg.

Endemann, D. H., et al., "Endothelial Dysfunction", *J. Am. Soc. Nephrol*, 15(8), (2004), 1983-1992.

"U.S. Appl. No. 09/993,465 Non Final Office Action mailed Jul. 30, 2003", 12 pgs.

"U.S. Appl. No. 09/993,465 Notice of Allowance mailed Dec. 12, 2003", 5 pgs.

"U.S. Appl. No. 09/993,465 Preliminary Amendment filed Nov. 14, 2001", 3 pgs.

"U.S. Appl. No. 09/993,465 Response filed Oct. 30, 2003 to Non Final Office Action mailed Jul. 30, 2003", 7 pgs.

"U.S. Appl. No. 10/796,261 Non Final Office Action mailed Jan. 11, 2005", 10 pgs.

"U.S. Appl. No. 10/796,261 Notice of Allowance mailed Jun. 29, 2005", 6 pgs.

"U.S. Appl. No. 10/796,261 Response filed Apr. 15, 2005 to Non Final Office Action mailed Jan. 11, 2005", 6 pgs.

"U.S. Appl. No. 10/847,810 Final Office Action mailed Oct. 21, 2005", 5 pgs.

"U.S. Appl. No. 10/847,810 Non Final Office Action mailed May 6, 2005", 8 pgs.

"U.S. Appl. No. 10/847,810 Notice of Allowance mailed Jan. 5, 2006", 8 pgs.

"U.S. Appl. No. 10/847,810 Preliminary Amendment filed May 18, 2004", 6 pgs.

"U.S. Appl. No. 10/847,810 Response filed Jul. 21, 2005 to Non Final Office Action mailed May 6, 2005", 11 pgs.

"U.S. Appl. No. 10/847,810 Response filed Nov. 10, 2005 to Final Office Action mailed Oct. 21, 2005", 6 pgs.

"U.S. Appl. No. 11/679,517, Preliminary Amendment filed May 3, 2007", 6 pgs.

03767028.8, "European Application Serial No. 03767028.8, Office Action mailed May 7, 2009", 2 pgs.

2,493,764, "Canadian Application No. 2,493,764 Office action Mailed Jan. 19, 2009", 4 pgs.

Coghlin Dickson, T. M, et al., "Effect of oral glutamine supplementation during bone marrow transplantation.", *JPEN J Parenter Enteral Nutr.*, 24(2), (Mar.-Apr., 2000), 61-6.

Hong, R. W, et al., "Glutamine preserves liver glutathione after lethal hepatic injury.", *Ann Surg.*, 215(2), (Feb. 1992), 114-9.

Jebb, S. A, et al., "5-fluorouracil and folinic acid-induced mucositis: no effect of oral glutamine supplementation.", *Br J Cancer.*, 70(4), (Oct. 1994), 732-5.

Jensen, J. P, et al., "Prevention of chronic radiation enteropathy by dietary glutamine.", *Ann Surg Oncol.*, 1(2), (Mar. 1994), 157-63.

Klimberg, V. S, et al., "Effect of supplemental dietary glutamine on methotrexate concentrations in tumors.", *Arch Surg.*, 127(11), (Nov. 1992), 1317-20.

PA/A/2005/001267, "Mexicon Application No. PA/a/2005/001267 Office Action Mailed Mar. 11, 2009", 2.

Peterson, D. E, et al., "Phase III study: AES-14 in chemotherapy patients at risk for mucositis", *Proc Am Soc Clin Oncol*, 22, 2003 ASCO Annual Meeting, (2003), Abstract 2917.

Petit, R. G, et al., "Aesgen-14 (uptake-enhanced L-glutamine suspension) reduces severe mucositis in acute radiation model where aqueous L-glutamine suspension is ineffective", *Proc Am Soc Clin Oncol*, 21, 2002 ASCO Annual Meeting, (2002), Abstract 2861.

Pytlik, R., et al., "Standardized parenteral alanyl-glutamine dipeptide supplementation is not beneficial in autologous transplant patients: a randomized, double-blind, placebo controlled study.", *Bone Marrow Transplant.*, 30(12), (Dec. 2002), 953-61.

Savarese, D. M, et al., "Prevention of chemotherapy and radiation toxicity with glutamine.", *Cancer Treat Rev.*, 29(6), (Dec. 2003), 501-13.

Schloerb, P. R, et al., "Oral and parenteral glutamine in bone marrow transplantation: a randomized, double-blind study", *JPEN J Parenter Enteral Nutr.*, 23(3), (May-Jun. 1999), 117-22.

"U.S. Appl. No. 11/679,517, Final Office Action mailed Jul. 17, 2008", 9 pgs.

"Canadian Application Serial No. 2,493,764, Office Action mailed Jan. 17, 2007", 2 pgs.

"Canadian Application Serial No. 2,493,764, Office Action mailed Dec. 17, 2007", 3 pgs.

"Canadian Application Serial No. 2,493,764, Response filed Jun. 16, 2008 to Office Action mailed Dec. 17, 2007", 11 pgs.

"Canadian Application Serial No. 2,493,764, Response filed Jul. 17, 2007 to Canadian Office Action mailed Jan. 17, 2007", 14 pgs.

"Chinese Patent Application Serial No. 03823601.X (781.020CN1), First Office Action mailed Aug. 10, 2007", (w/ English Translation),10 pgs.

"European Application No. 03767028.8, Office Action mailed on Aug. 22, 2008", 9 pgs.

"Guide to Inspections of Lyophilization of Parenterals", [Online]. [retrieved Jul. 9, 2008]. Retrieved from the Internet: <URL: http://www.fda.gov/ora/inspect_ref/igs/Iyophi.html>, 35 pgs.

"Japanese Application Serial No. 2004526274 Office Action Mailed Dec. 2, 2008", 3 pgs.

"New Zealand Application Serial No. 538405, Examination Report mailed Apr. 11, 2006", 3 pgs.

"New Zealand Application Serial No. 538405, Examination Report mailed Jul. 25, 2007", 2 pgs.

"New Zealand Application Serial No. 538405, Response filed Oct. 23, 2007 to Examination Report mailed Jul. 25, 2007", 2 pgs.

"New Zealand Application Serial No. 538405, Response mailed Jul. 11, 2007 to Examination Report mailed Apr. 11, 2006", 28 pgs.

"New Zealand Patent Application Serial No. 556447 Examination Report mailed Jul. 16, 2007", 2 pgs.

Yagasaki, K., et al., "Actions of Amino Acids on the Proliferation and Invasion of Hepatoma Cells in Culture", *Reports of The Research Commitee of Essential Amino Acids*, No. 146, (1996), 84-87.

\* cited by examiner

RELATIVE L-ASPARAGINE UPTAKE INTO CELL MONOLAYER FROM VEHICLE vs NON-VEHICLE

RELATIVE L-GLUTAMINE UPTAKE INTO CELL MONOLAYER FROM VEHICLE vs NON-VEHICLE

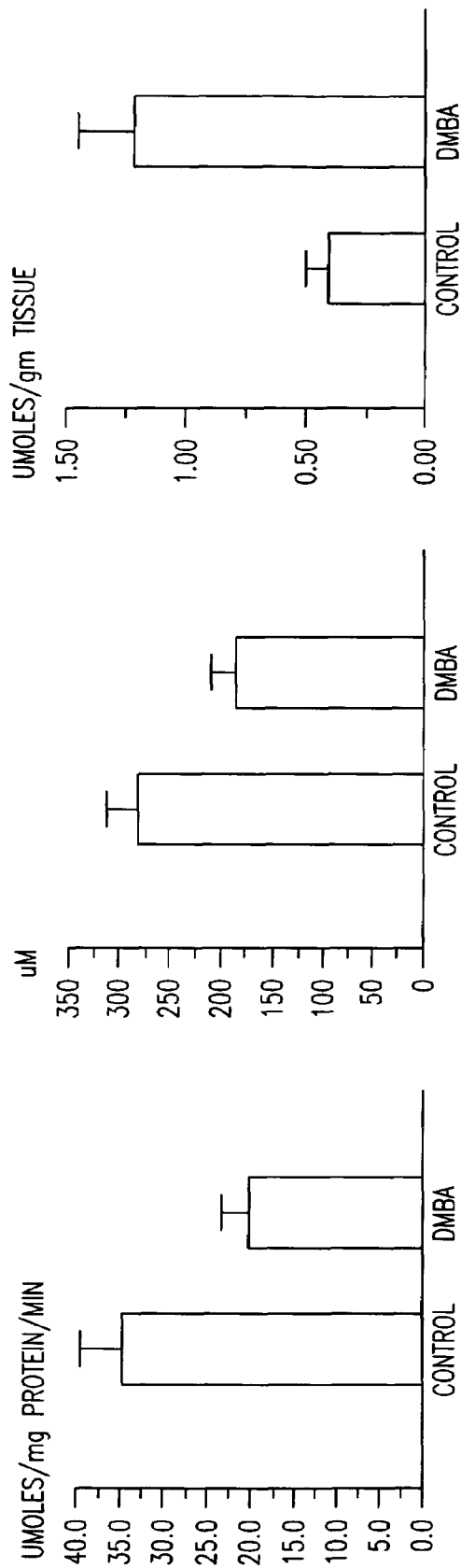

*p<0.05, ANOVA, GLN vs. FA AND H2O

*p<0.05, ANOVA, GLN vs. FA AND H2O

TREATMENT OF CANCER WITH GLUTAMINE

RELATED APPLICATIONS

This application claims priority from U.S. provisional application 60/400,446, filed Aug. 1, 2002, which is incorporated by reference.

BACKGROUND OF THE INVENTION

Absorption of biomolecules, such as amino acids and proteins, is critical to cellular function. About 75 percent of the solids in the mammalian body are proteins, including enzymes, polypeptides such as cytokines, nucleoproteins, transport proteins, and structural proteins. The principal functional constituents of these proteins, amino acids, polypeptides and isolated amino acids, are also important for cellular metabolic functions. The amino acid glutamine, for example, serves important functions in metabolism, including transport of carbon and nitrogen between tissues. It is a precursor for hepatic and renal gluconeogenesis, as well as urea synthesis in the liver and ammonia production in the kidney. A number of cell types, particularly the cells of the intestinal mucosa, also utilize large amounts of glutamine as their major source of respiratory fuel.

The effectiveness of amino acid supplementation for treatment of a variety of physiologic disorders has been demonstrated. D-serine supplementation, for example, augments the beneficial effects of antipsychotics for the treatment of schizophrenia. (Tsai, G., et al., Biol. Psychiatry (1998) 44(11): 1081-1089.) L-tryptophan or 5-hydroxytryptophan supplementation has been shown to improve symptoms of depression, anxiety, insomnia and pain in patients with fibromyalgia. (Juhl, J. H., Altern. Med. Rev. (1998) 3(5): 367-375.) Dietary supplementation with 8 essential and 9 nonessential amino acids provided improved health, tone, and mood in dialysis patients, in whom protein malnutrition is a common problem. (Mastroiacovo, P., et al., Clin. Ther. (1993) 15(4): 698-704.) Nutritional supplementation with aspartic acid has been suggested for the treatment of Canavan disease, a rare recessive autosomal genetic disorder generally resulting in death within several years of onset. (Baslow, M. H., et al., J. Mol. Neurosci. (1997) 9(2): 109-125.) L-lysine has also been demonstrated to have therapeutic use for lesions associated with herpes simplex virus type 1 (HSV-1). (Ayala, E. And D. Krokorian, J. Med. Virol. (1989) 28(1): 16-20.)

Glutamine supplementation has been shown to provide numerous benefits, including stimulation of certain cells of the immune system and general promotion of cellular growth. Depletion of glutamine results in atrophy of epithelial tissue, with associated bacterial translocation. Clinical supplementation of glutamine reduces epithelial atrophy and accelerates recovery.

Dietary glutamine supplementation has been proposed for the treatment of patients recovering from surgery or suffering from sepsis, inflammation, burns, or trauma. Topical administration, usually in the form of a "swish and swallow" solution for oral use to repair the damaged epithelial tissue of mouth or esophageal sores, can be effective in many patients who have undergone bone marrow transplantation or chemotherapy. (Skubitz, et al., J. Lab. Clin. Med. (1996) 127(2): 223-8; Anderson, et al., Bone Marrow Transplant (1998) 22(4): 339-44.)

Glutamine supplementation can be beneficial for cancer therapy for both its direct and indirect results. Glutamine supplementation has been shown to increase glutathione release from the gut in Fisher-344 rats. (Cao, Y., et al., J. Parenter. Enteral Nutr. (1998) 22(4): 224-227.) When given in conjunction with either radiation or chemotherapy, glutamine has been demonstrated to increase selectivity of either therapy for tumor cells. (Klimberg, V. and J. McClellan, Am. J. Surg. (1996) 172(5): 418-424.) In one study, tumor growth in rats receiving glutamine, either by gavage or as a food additive, decreased by 40% within three weeks. (Fahr, M., et al., J. Parenter. Enteral Nutr. (1994) 18(6): 471-476.) In a separate study, tumor volume loss in rats receiving methotrexate was nearly doubled when glutamine was added to the diet. (Klimberg, V., et al., J. Parenter. Enteral Nutr. (1992) 16 (6 Suppl): 83S-87S.) Decreased tumor growth in glutamine-supplemented rats has been correlated with greater natural killer cell activity, presumably due to glutathione-mediated suppression of prostaglandin E2 (PGE2) synthesis. (Klimberg, V., et al., J. Surg. Res. (1996) 63(1): 293-297.)

Formulations for the administration of amino acids, particularly glutamine, are described in U.S. provisional patent application No. 60/134,442 filed May 17, 1999 and incorporated by reference herein.

The effectiveness of amino acid supplementation has been limited in some individuals due to aging or disease. Effective supplementation with certain amino acids is further limited to varying degrees by the low aqueous solubility and limited cellular uptake of some amino acids. Glutamine, for example, exhibits a low solubility in water (48 g/l at 30° C., 26 g/l at 18° C., 18 g/l at 0° C.; The Merck Index, 12th Edition) and a low chemical stability in aqueous solution (11 days at 22-24° C.). (Cardona, P., Nutr. Hosp. (1998) 13(1): 8-20).

Transport of small molecules into various cell types is controlled by alternate transport systems, making it more difficult to devise methods for increasing cellular uptake into particular cell types. Despite the need for methods to enhance the uptake of amino acids and other small molecules, methods for increasing initial direct absorption of amino acids, peptides and other compounds into cells such as epithelial cells, the type of cells initially responsible for initial uptake of many bioactive compounds, has not been described.

Therefore, a continuing need exists for methods to increase cellular uptake of bioactive compounds into mammalian cells.

*Cryptosporidium parvum* is a leading cause of persistent diarrhea in developing countries. It is particularly problematic in AIDS patients, the elderly, and the very young, in whom it can cause a life-threatening diarrhea. Therefore, there is a continuing need for methods to treat cryptosporidiosis.

Wounds, injuries, and infections of the skin, such as abrasions, burns, ulcers, herpetic lesions, and insect stings, are common, painful, and often disfiguring. Therefore, a need exists for methods to promote healing of skin and associated tissues damaged by wounds, injuries, and infections of the skin.

Cancer is the second leading killer in the United States. There is a need for methods to prevent and treat cancers in general and particular types of cancer, such as breast cancer.

The primary tools for treatment of cancer are radiation therapy and chemotherapy. However, these tools are often unable to halt or reverse the progression of cancer. Furthermore, both chemotherapy and radiation have side-effects that limit the quality of life for cancer patients and often require curtailing treatment.

Therefore, a continuing need exists for methods to treat cancer, to enhance the effectiveness of current treatments for cancer, to prevent recurrence and metastasis of cancer, and to alleviate the side-effects of chemotherapy and radiation therapy.

SUMMARY

The invention provides methods of treating or preventing various conditions, particularly cancer and conditions associated with cancer treatment, by administration of glutamine. For instance, one embodiment of the invention provides a method of preventing metastatis in a mammal afflicted with cancer, such as a human cancer patient, involving administering an effective amount of glutamine. Other embodiments of the invention provide a method of preventing recurrence of cancer and a method of inhibiting the onset of cancer in a mammal involving administering an effective amount of glutamine. Another embodiment of the invention provides a method of protecting non-mucosal tissue such as skin or breast tissue against damage from radiation therapy or chemotherapy by administering glutamine. Another embodiment of the invention provides a method of reducing or preventing pain arising from a non-mucosal tissue by administering glutamine. Another embodiment of the invention provides a method of promoting healing of skin damaged by wound, injury, or infection involving administering glutamine. Another embodiment of the invention provides a method of treating an infection such as a *Cryptosporidium* infection (cryptosporidiosis) in a mammal by administering glutamine.

It has unexpectedly also been found that the effectiveness of glutamine in these applications can be enhanced by the coadministration of an effective amount of a carbohydrate, such as a saccharide. For example, another embodiment of the invention provides a method of enhancing the effectiveness of chemotherapy and/or radiation therapy of a mammal afflicted with cancer by administering glutamine in combination with an effective amount of carbohydrate.

Another embodiment of the invention provides a method of increasing the therapeutic index of chemotherapy and/or radiation therapy by administering to a mammalian subject afflicted with cancer a composition comprising (a) glutamine or a pharmaceutically acceptable salt thereof in an amount effective to increase glutathione concentration in at least one normal tissue and decrease glutathione concentration in tumor tissue, thereby reducing the susceptibility of the normal tissue and increasing the susceptibility of the tumor tissue to killing by the chemotherapy and/or radiation therapy, and (b) carbohydrate in an amount effective to increase the absorption of glutamine by the subject.

Another embodiment of the invention provides a method of promoting apoptosis of cancer cells by administering to a mammalian subject a composition containing glutamine and at least one carbohydrate in an amount effective to increase the absorption of glutamine by the subject.

Several proteins are known to promote or inhibit cancer cell proliferation, or alternatively apoptosis (programmed cell death). The inventors have discovered that administration of glutamine increases the levels of pro-apoptotic proteins such as Bad, Bax, p21, and caspase-3, and decreases the levels of proteins that are anti-apoptotic or promote cancer cell proliferation, such as Bcl-2, IGF-1, IGF-1R, and Akt. Accordingly, certain embodiments of the invention provide methods of increasing the protein levels, gene expression, or enzyme activity of Bad, Bax, or p21 by administering to a mammalian subject a composition comprising (a) glutamine or a pharmaceutically acceptable salt thereof and (b) carbohydrate in an amount effective to increase the absorption of glutamine by the subject. Likewise, certain embodiments of the invention provide methods of decreasing the protein levels or gene expression of IGF-1, IGF-1R, or Akt by administering to a mammalian subject a composition comprising (a) glutamine or a pharmaceutically acceptable salt thereof and (b) carbohydrate in an amount effective to increase the absorption of glutamine by the subject.

The invention provides a composition and a method for increasing cellular uptake of bioactive agents, particularly those compounds termed "small molecules," and more particularly glutamine into the cells of mammalian tissue. The composition is a solution, dispersion, or suspension comprising an aqueous vehicle and an effective amount of glutamine, in combination with an amount of carbohydrate effective to achieve increased transport (absorption) of the glutamine into the target cells in vivo or in vitro. The transport (absorption) is increased over the amount that would enter the cells under physiological conditions, i.e., under homeostatic conditions, when the cells are contacted with the glutamine dissolved or suspended in water or in a physiological salt solution. Preferably, the transport (absorption) is increased by a factor of at least about 100-2000 times that which is obtainable by employing an up-to saturated aqueous solution of the active agent. The mechanism by which carbohydrate enhances uptake of small molecules into mammalian cells in vitro or in vivo is unknown.

The carbohydrate carrier can comprise a monosaccharide, such as glucose, a disaccharide, such as sucrose, or a combination of monosaccharides and disaccharides. The carbohydrate carrier can also comprise a sugar alcohol such as mannitol, sorbitol or xylitol. The carbohydrate carrier can also comprise a polysaccharide such as high fructose corn syrup or corn syrup solids, wherein the corn syrup or corn syrup solids, hydrous or anhydrous, constitute a solution phase for the active agent(s). The carrier can be combined with water, or with a mixture of water with pharmaceutically acceptable alkanols, alkylene glycols or polyols such as glycerol, to form a solution. Preferably the organic solvents constitute a minor proportion of the aqueous phase, preferably $\leqq$5-10 vol-%.

The solution can be a true solution or a flowable "solid solution." It can be administered by a variety of means for the administration of liquids, including toothpaste, chewing gum, hard or soft gelatin capsules, suppositories, enemas, mouthwashes, or other liquid dosage forms such as topically applied lotions, or drinks, such as a shake.

Administration of the composition of the invention can provide treatment for a variety of physiologic disorders ameliorated by enhancement of absorption of bioactive agents into damaged or intact tissues, especially disorders affecting the endothelial cells and fibroblasts of epithelial tissue. Such physiologic disorders involving damaged tissue, include, for example, lesions of the oral, esophageal, and/or gastrointestinal mucosa following radiation or chemotherapy in patients treated for cancer or in whom bone marrow transplant is performed, gastric and peptic ulcers, burns, major and minor trauma wounds, viral lesions, inflammatory bowel disorder, Crohn's disease, Sjoren's syndrome, xerostoma, and cryptosporidiosis.

Pharmaceutical dosage compositions are also provided, consisting of either bulk-packaged or individually-packaged pre-mixed dry or liquid formulations of a therapeutically effective dose of an amino acid such as glutamine in admixture with an amount of carbohydrate carrier effective to achieve increased absorption of the amino acid into epithelial cells. Kits can also be provided comprising, separately packaged in one container, dry formulation(s) and pre-measured aqueous vehicle(s).

BRIEF DESCRIPTION OF THE DRAWINGS

FIG. 26 shows the effect of ingesting DMBA on glutathione (GSH) transport measured in rat jejunal basolateral membrane vesicles.

FIG. 27 shows the portal blood glutathione (GSH) concentration of rats 1 week after ingesting BMDA or sesame oil (control).

FIG. 28 shows the effect of ingesting DMBA on the concentration of glutathione (GSH) in rat gut mucosa.

DETAILED DESCRIPTION OF THE INVENTION

Figure 1:
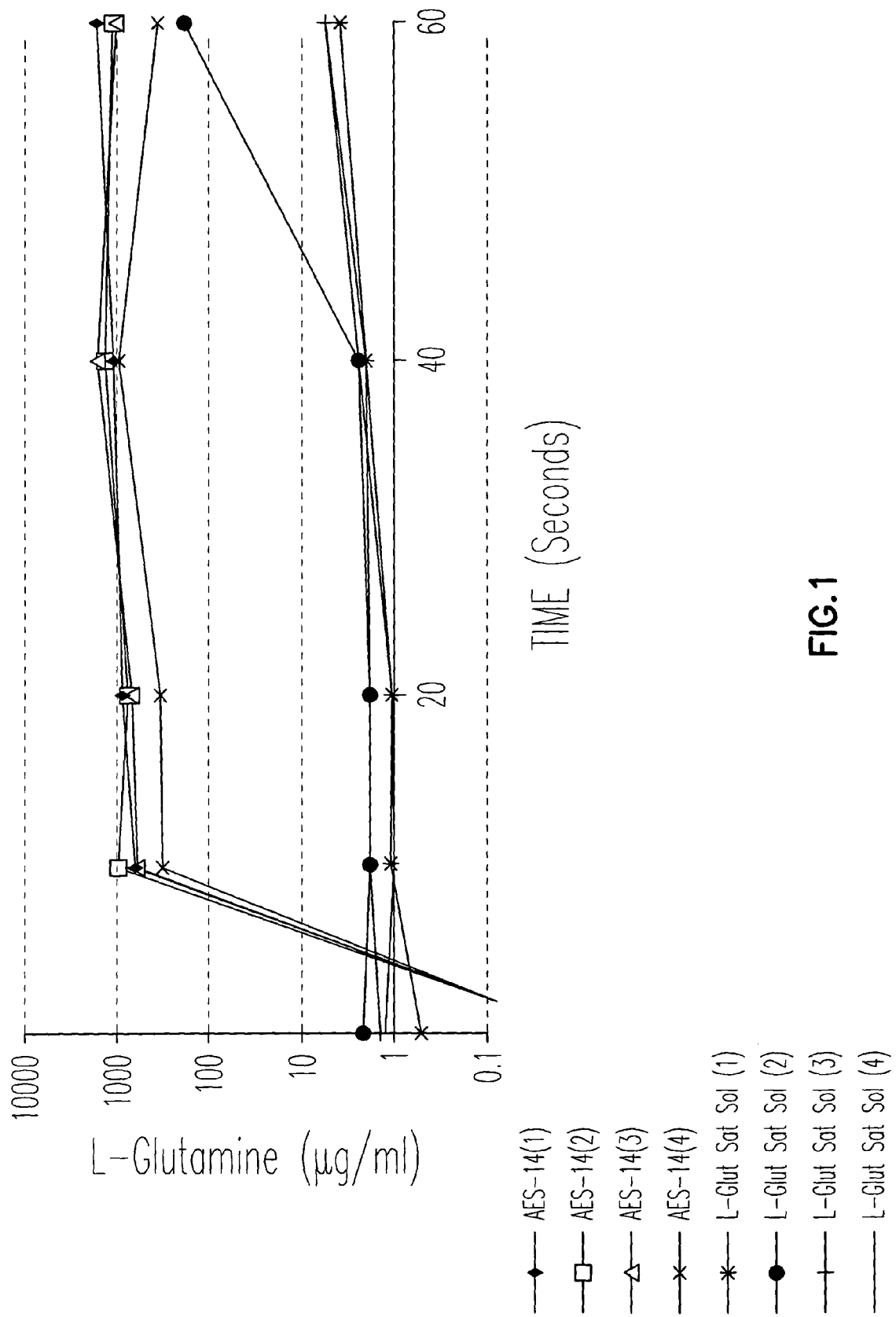
FIG. 1 and FIG. 2 are graphs illustrating the increased amino acid uptake achieved using a composition and method of the invention. The amino acid glutamine was administered to CaCo cells in combination with an effective amount of carbohydrate carrier (7:1 ratio of carbohydrate carrier to amino acid) (Aesgen-14), with amino acid administered as a saturated solution without additional components (L-Glut Sat Sol) as a control. As indicated by the figure legend and the graph, intracellular glutamine concentration was increased significantly in cells treated with a combination of amino acid and carbohydrate carrier, as compared to that achieved by glutamine administration alone. Incubation time in seconds is indicated on the X axis, with cellular glutamine uptake on the Y axis.
Figure 2:
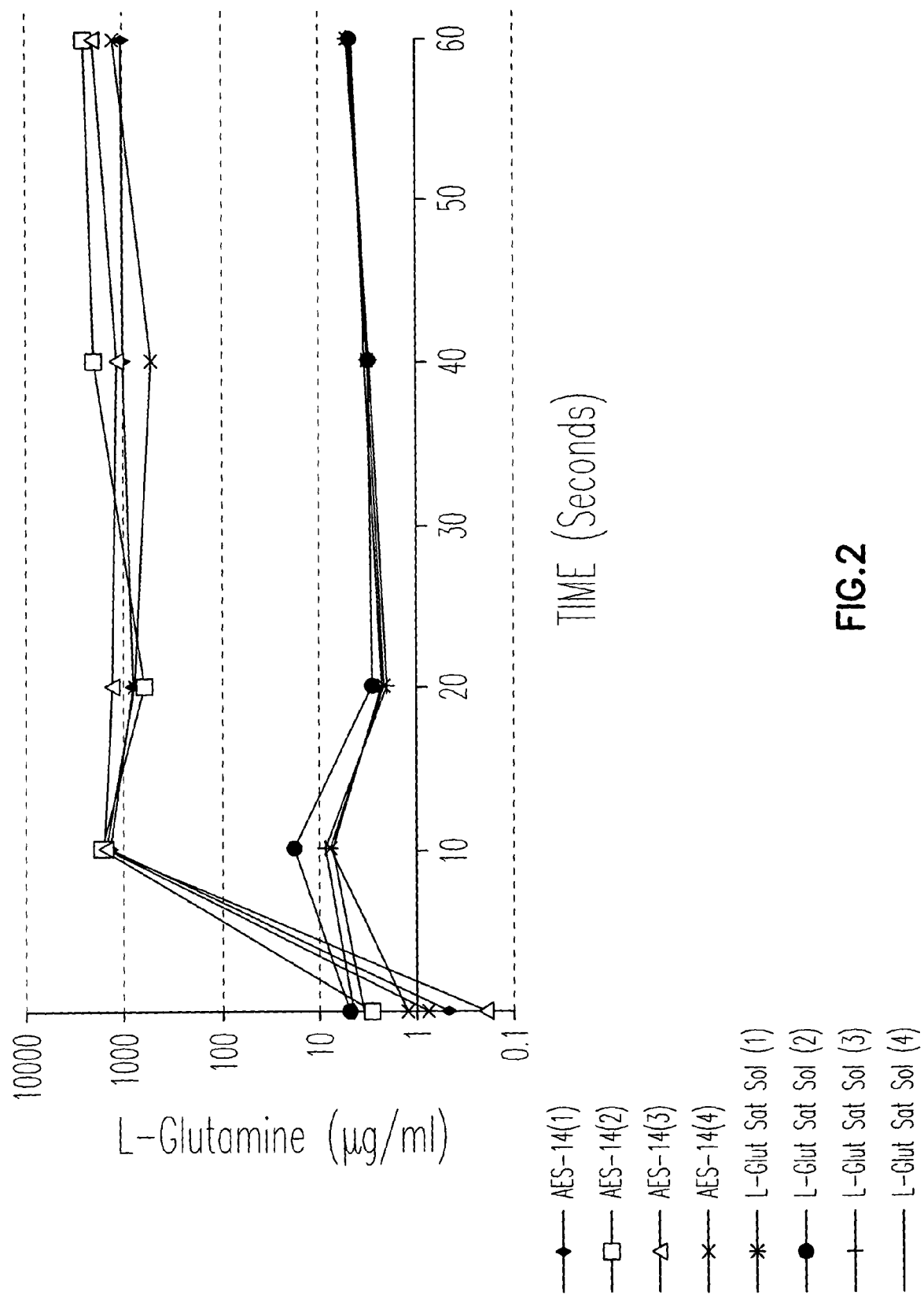
Figure 3:
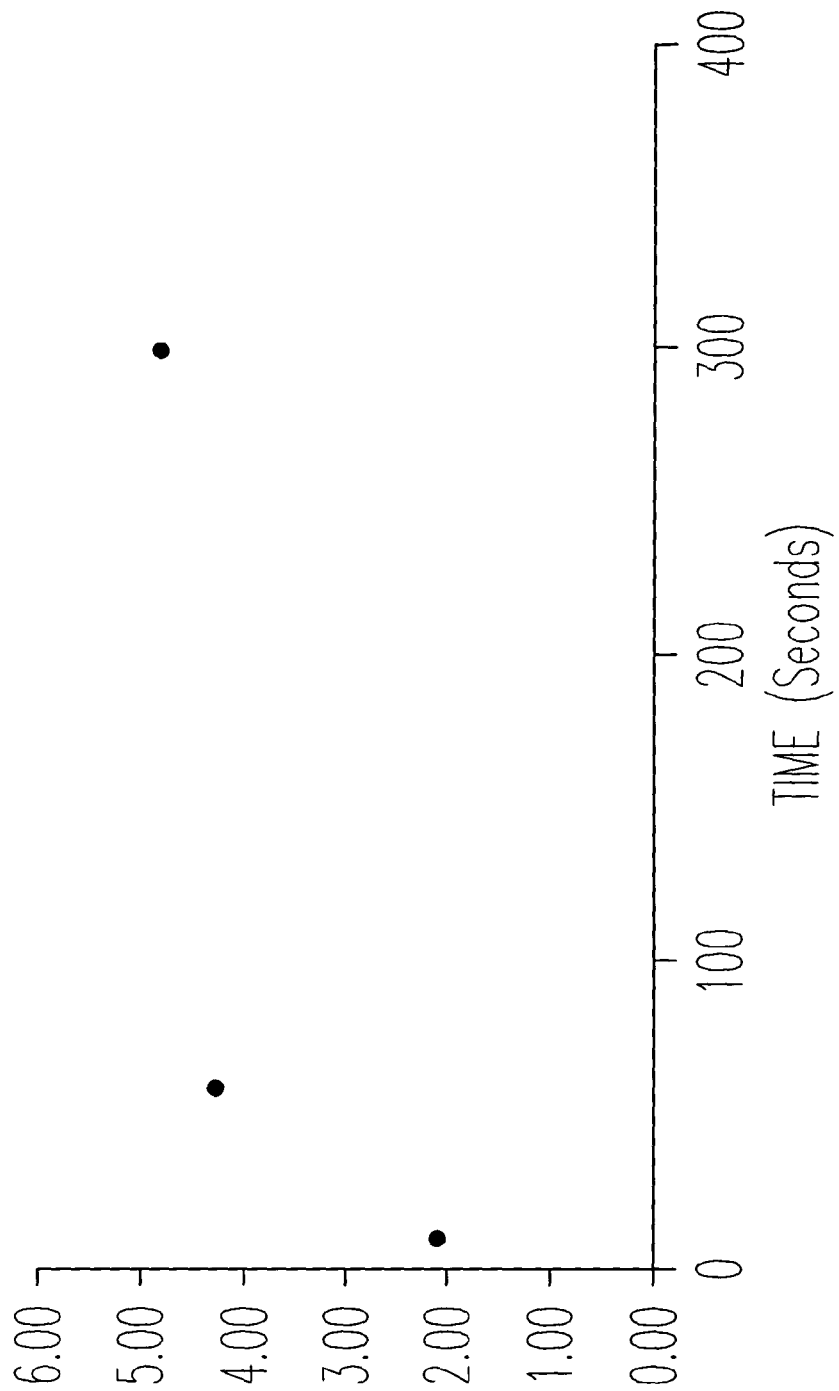
FIG. 3 depicts the relative effect of vehicle on L-glutamine cellular uptake.
Figure 4:
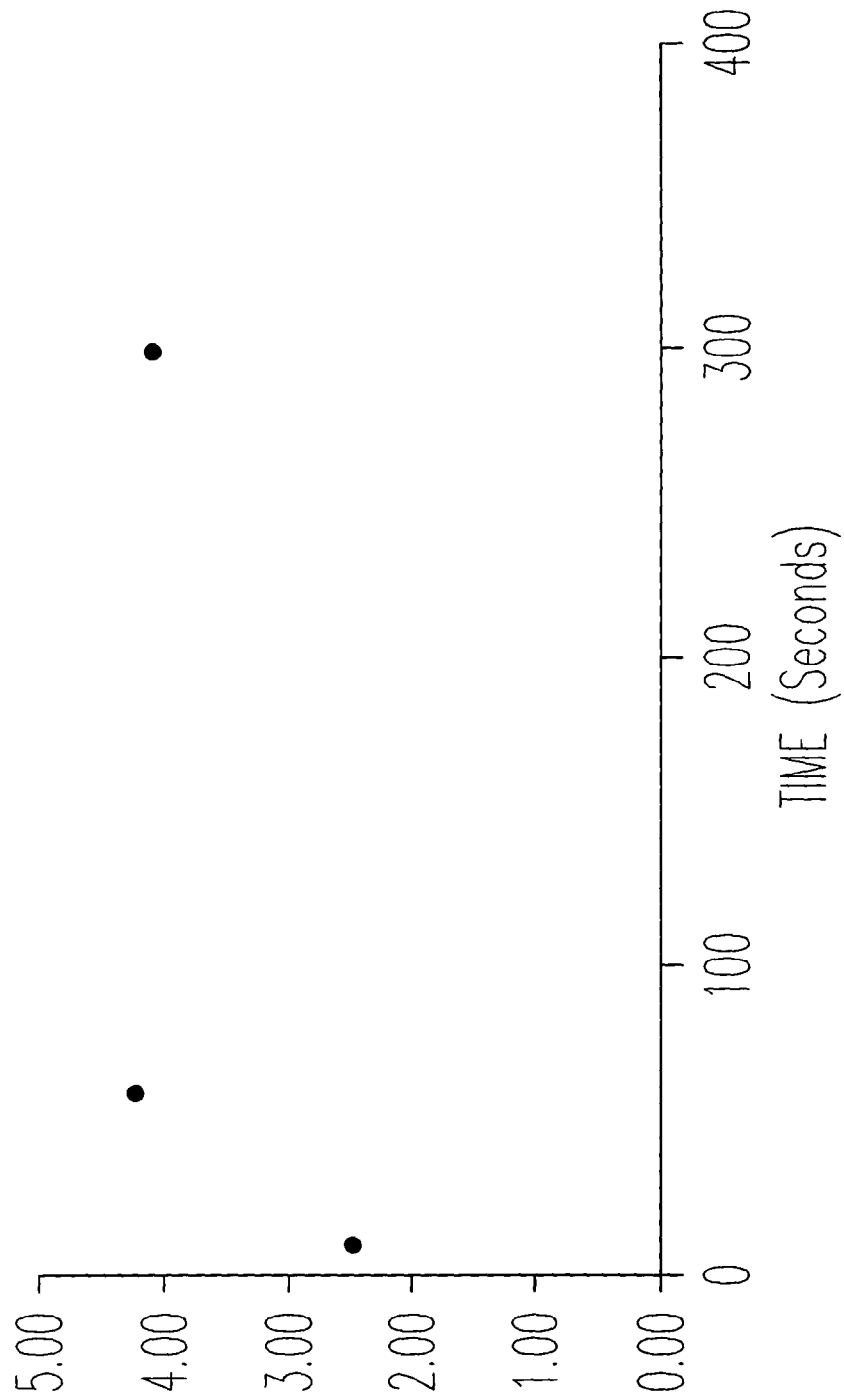
FIG. 4 depicts the relative effect of vehicle on glycylsarcosine cellular uptake.
Figure 5:
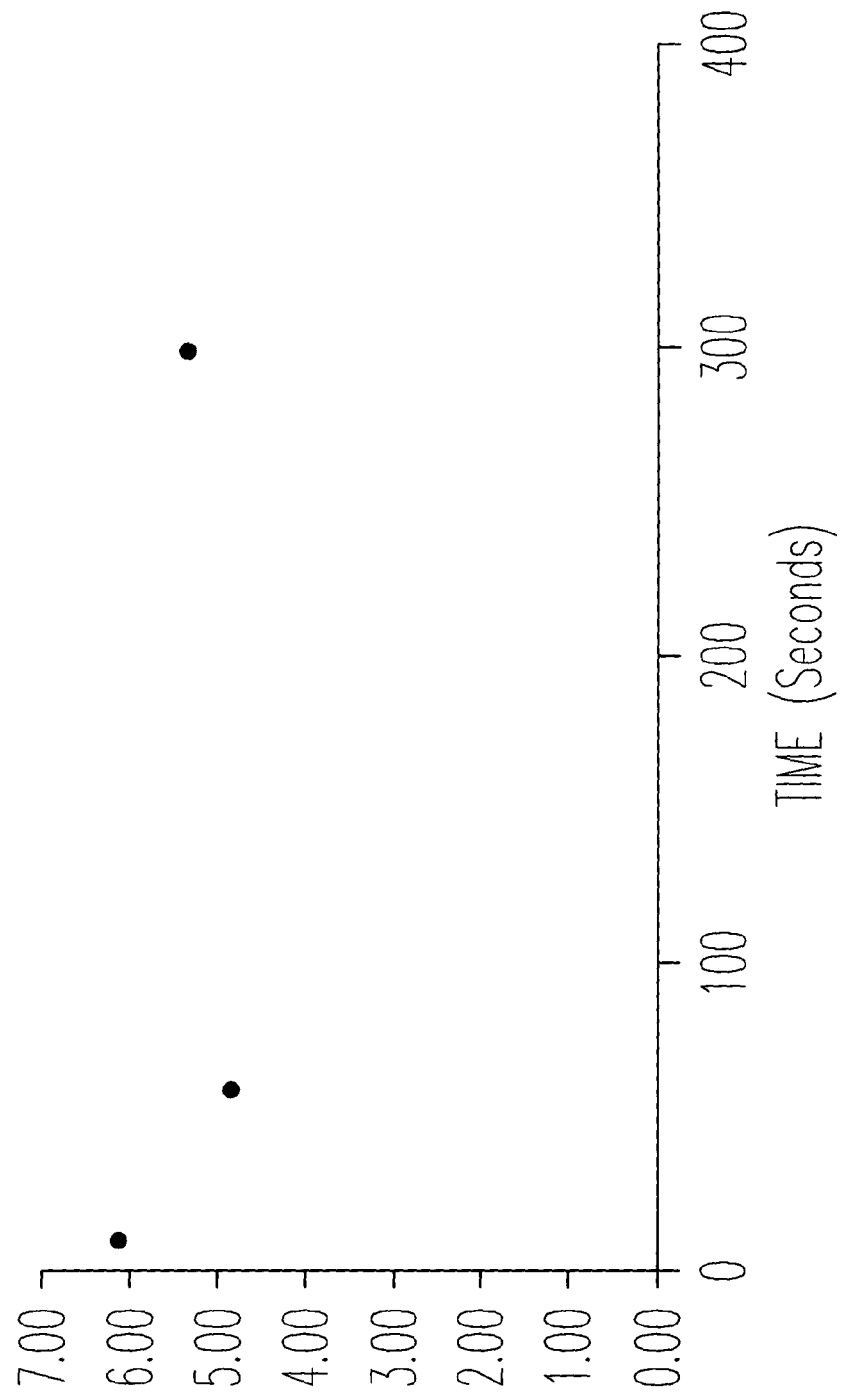
FIG. 5 depicts the relative effect of vehicle on L-asparagine cellular uptake.
Figure 6:
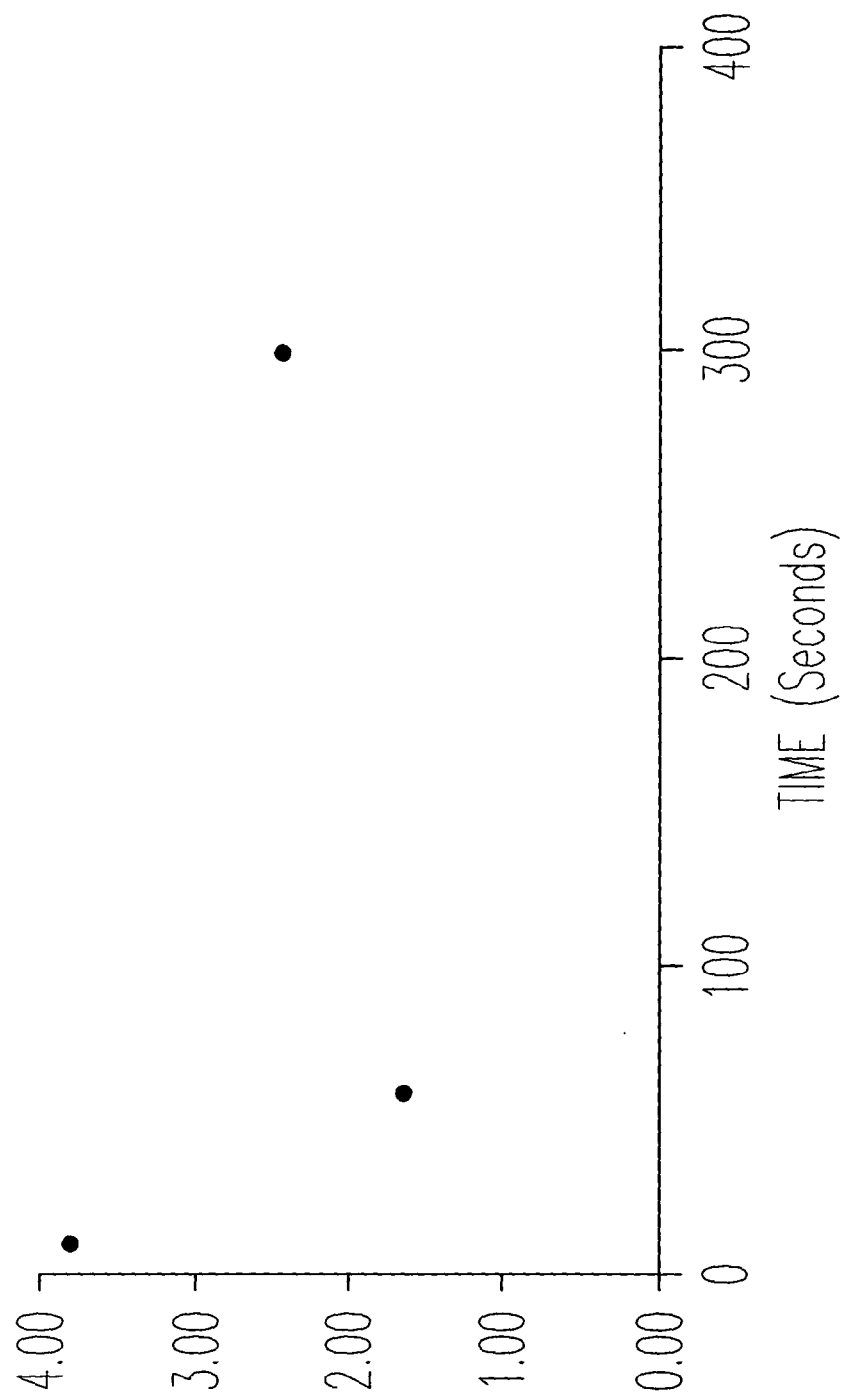
FIG. 6 depicts the relative effect of vehicle on acyclovir cellular uptake.

The inventors have discovered a composition that increases the cellular uptake of bioactive agents into mammalian cells in vitro or in vivo. Using the composition and method of the invention, increased gastrointestinal epithelial cell uptake of the amino acid glutamine by a factor of about 150× or more within ten seconds after administration has been demonstrated. The present invention also provides a method for treating patients suffering from a number of pathophysiological conditions, using the composition to increase cellular uptake of bioactive agents in therapeutic amounts.

As used herein, the term "bioactive agent" refers to a molecule that exerts a therapeutic or nutritive effect on a mammal following absorption of an effective amount of the molecule by the target cells.

As used herein, the term "effective amount" refers to an amount that causes a detectable biological change in a target cell population, and preferably an amount that accomplishes a therapeutic effect, i.e., reduces at least one symptom of a pathology or disease afflicting the mammal.

As used herein, "amino acid" includes, for example, alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine, valine, citrulline, g-aminobutyric acid, hydroxyproline, and omithine, as well as dipeptides such as glutamyl glutamate and tripeptides such as glutathione. (See *Remington's Pharmaceutical Sciences* (19th ed.) at pages 389-392.) The composition and method are particularly useful, however, for increasing absorption of those amino acids which exhibit limited aqueous solubility and/or poor cellular uptake, such as glutamine. Limited aqueous solubility, as used herein, is defined as a solubility of less than about 5 grams amino acid in 100 ml water at 22-25° C.

As used herein, the term "glutamine" includes glutamine (glutamic acid 5-amide) and hydrolyzable derivatives of glutamine, such as esters and/or amides of glutamine (e.g., short peptides), with a molecular weight smaller than about 1000, preferably smaller than about 500, that yield glutamine in the body of a mammal. Pharmaceutically acceptable salts of glutamine can also be employed in the present methods, including the acid addition salts of amines, such as hydrochlorides, acetates, tartrates, citrates, and the like, and carboxylate salts, such as sodium and potassium salts. The weight of glutamine or weight ratio of glutamine to other components, in the context of a salt or hydrolyzable derivative of glutamine, refers to the weight of the glutamine portion of a hydrolyzable glutamine derivative, or the weight of the glutamine portion of a salt of glutamine. For instance, since the formula weight of sodium glutamine is 168 and the formula weight of glutamine is 146, a composition containing 1 gram of sodium glutamine would be considered to contain 0.87 grams of glutamine.

The present solutions can also enhance the in vitro or in vivo cellular absorption of a wide variety of bioactive agents, preferably in therapeutic amounts, particularly of the entities generally referred to as "small molecules."

As used herein, the term "small molecule" includes single molecular entities such as amino acids, steroids, cytokines, hormones, hormonal regulators, enzymes, vitamins and the like that generally have a molecular weight of less than 30 kD, preferably less than 25 kD, most preferably less than 10 kD, i.e., a molecular weight of $\leq 5000$ daltons.

As used herein, the term "oligopeptide" is a peptide comprised of 2 to 20 amino acids.

As used herein, the term "therapeutic index" refers to the ratio of killing of cancer cells to killing of normal or non-target cells by chemotherapy or radiation therapy.

As used herein, "natural killer cell activity" refers to the cell killing activity of natural killer cells. This can be measured, for instance, in a cytotoxicity assay such as that described in Example 10 below.

Enhanced absorption of bioactive agents into the skin or intact mucosal tissue of the gut can also be used to administer bioactive agents having an effect on organs or tissues remote from the site of administration.

"Carbohydrate," as used herein, includes those sugars known as monosaccharides and disaccharides, polyols, hydroxy analogs or sugar alcohols, such as, for example, xylitol, sorbitol, and mannitol, and their polymers, such as dextrins, high fructose corn syrup, and corn syrup solids. It is well known in the art that certain mono- and disaccharides form sugar alcohols, or hydroxy analogs. Certain of these hydroxy analogs, particularly sorbitol and xylitol, have proven to provide the benefit of a sugar taste without the cariogenic properties of the mono- and disaccharides from which they are derived.

The mechanism by which carbohydrate enhances uptake of small molecules into mammalian cells in vitro or in vivo is unknown. In some embodiments, there will be a major proportion by weight of carbohydrate in the final composition, e.g., greater than 80-90 weight percent. In some cases the composition can be essentially free of added water, i.e., can be a "solid solution," the carbohydrate acting as a "solvent" for the active ingredient. Such "solid solutions" can be flowable, semisolid or even solid. The ratio of carbohydrate to active agent can be about 0.5:1 to about 50:1. It can be, for instance, approximately 1.5:1 w/w to 20:1 w/w in a dry preparation, and greater than 4:1 w/v in final aqueous solution, preferably 4:1 w/v to 15:1 w/v, most preferably greater than 7:1 w/v, achieved either by constitution of the preparation with aqueous solvent or by delivery into the aqueous environment of the extracellular fluids surrounding the target tissue.

"Cell," as used herein, includes any cell that can be contacted by the present composition in accord with the present method, such as epithelial cells, endothelial cells, skin cells, fibroblasts or neuronal cells. More specifically, cells in which the composition and method of the present invention have been demonstrated to increase absorption of the amino acid glutamine are gastrointestinal epithelial cells., including cells of the mouth, throat, esophagus, stomach, intestines, colon and rectum, endothelial cells and fibroblasts.

"Constitution with aqueous solvent," as used herein, includes constitution with water, physiological salt solutions or buffers, fruit juice or other liquid which contains a high percentage of water, or with extracellular fluids surrounding the tissue to which the composition is applied, such as saliva, mucous, gastric fluids, spinal fluid, and the like.

Statements of the Invention

One embodiment of the invention provides a method of preventing metastasis in a mammalian subject afflicted with cancer, the method comprising administering to the subject a composition comprising a therapeutically effective amount of glutamine or a pharmaceutically acceptable salt thereof. The composition may also include carbohydrate in an amount effective to increase the absorption of glutamine by the subject.

Another embodiment of the invention provides a method of preventing recurrence of cancer comprising orally administering to a mammalian subject in remission from cancer or undergoing anti-cancer therapy a composition comprising a therapeutically effective amount of glutamine or a pharmaceutically acceptable salt thereof. The composition may also include carbohydrate in an amount effective to increase the absorption of glutamine by the subject.

Another embodiment of the invention provides a method of inhibiting the onset of cancer in a mammalian subject at risk of developing cancer comprising administering to the subject a composition comprising a therapeutically effective amount of glutamine or a pharmaceutically acceptable salt thereof and carbohydrate in an amount effective to increase the absorption of glutamine by the subject. Preferably the administration is oral.

Another embodiment of the invention provides a method of protecting non-mucosal tissue against damage from radiation therapy, the method comprising: administering to a mammalian subject afflicted with cancer and treated with radiation therapy a composition comprising a therapeutically effective amount of glutamine or a pharmaceutically acceptable salt thereof, that protects the non-mucosal tissue against damage from the radiation therapy. The composition may also include carbohydrate in an amount effective to increase the absorption of glutamine by the subject.

This method can allow the subject to be treated with a higher dose of radiation and/or treated with radiation for a longer time.

The non-mucosal tissue can be breast tissue or associated upper body tissue.

The composition can prevent increased breast density or lessens the severity of increased breast density caused by radiation therapy. The composition can also prevent edema or lessens the severity of edema, for instance edema of breast tissue.

The non-mucosal tissue protected can also be skin.

The composition can protect the appearance of the non-mucosal tissue.

Another embodiment of the invention provides a method of protecting skin against damage from chemotherapy, the method comprising: administering to a mammalian subject afflicted with cancer and treated with chemotherapy a composition comprising a therapeutically effective amount of glutamine or a pharmaceutically acceptable salt thereof, that protects the skin against damage from the chemotherapy. The composition may also include carbohydrate in an amount effective to increase the absorption of glutamine by the subject.

Another embodiment of the invention provides a method of protecting breast tissue against damage from chemotherapy, the method comprising: administering to a mammalian subject afflicted with cancer and treated with chemotherapy a composition comprising a therapeutically effective amount of glutamine or a pharmaceutically acceptable salt thereof, that protects the breast tissue against damage from the chemotherapy. The composition may also include carbohydrate in an amount effective to increase the absorption of glutamine by the subject.

Another embodiment of the invention provides a method of reducing or preventing pain arising from a non-mucosal tissue, the method comprising: administering to a mammalian subject afflicted with cancer and treated with chemotherapy and/or radiation therapy a composition comprising a therapeutically effective amount of glutamine or a pharmaceutically acceptable salt thereof, that reduces or prevents pain in the non-mucosal tissue arising from the treatment. The composition may also include carbohydrate in an amount effective to increase the absorption of glutamine by the subject.

The composition can allow the subject to be treated with a higher dose of radiation and/or treated with radiation for a longer time. If the subject is treated with chemotherapy, the composition can allow the subject to be treated with a higher dose of a chemotherapeutic agent and/or treated with the chemotherapeutic agent for a longer time.

The composition can allows the reduction or elimination of the need for further pain control for the subject for pain caused by chemotherapy and/or radiation therapy.

The non-mucosal tissue can be, for instance breast tissue or skin.

Another embodiment of the invention provides a method of protecting skin of a mammal against radiation injury, the method comprising administering to a mammal prior to exposure to radiation, a composition comprising an effective amount of glutamine or a pharmaceutically acceptable salt thereof. The composition may also include carbohydrate in an amount effective to increase the absorption of glutamine by the subject. The composition can be administered topically or internally. The radiation injury can be, for instance, caused by sun exposure (sunburn), or by artificial radiation exposure, as by therapeutic irradiation caused by internal or external sources.

Another embodiment of the invention provides a method of promoting healing of skin damaged by wound, injury, or infection comprising: administering to a mammalian subject a composition comprising a therapeutically effective amount of glutamine or a pharmaceutically acceptable salt thereof, so as to promote healing of non-mucosal tissue damaged by wound, injury, or infection of the skin. The composition may also include carbohydrate in an amount effective to increase the absorption of glutamine by the subject.

The non-mucosal tissue can be epithelial tissue (e.g., skin). The composition can be administered topically or internally. The composition can be a solid, gel, paste, or syrup.

The tissue can be tissue damaged by a wound, such as an abrasion or laceration. The tissue can be tissue damaged by injury, such as a burn, sunburn, radiation injury, ulcer (e.g., a decubitus ulcer), or insect bite or sting. The tissue can be tissue damaged by bacterial, fungal or viral infection (e.g., a herpetic lesion).

Another embodiment of the invention provides a method of treating cryptosporidiosis in a mammalian subject, the method comprising administering to the subject a composition comprising a therapeutically effective amount of glutamine or a pharmaceutically acceptable salt thereof. The composition may also include carbohydrate in an amount effective to increase the absorption of glutamine by the subject.

Another embodiment of the invention provides a method of enhancing the effectiveness of chemotherapy and/or radiation therapy, comprising: administering to a mammalian subject treated for cancer with chemotherapy and/or radiation therapy a therapeutically effective amount of a composition comprising glutamine or a pharmaceutically acceptable salt thereof and at least one carbohydrate in an amount effective to increase the absorption of glutamine by the subject.

Another embodiment of the invention provides a method of increasing the therapeutic index of chemotherapy and/or radiation therapy comprising: administering to a mammalian subject treated for cancer with chemotherapy and/or radiation therapy a composition comprising (a) glutamine or a pharmaceutically acceptable salt thereof in an amount effective to increase glutathione concentration in at least one normal tissue and decrease glutathione concentration in tumor tissue, thereby reducing the susceptibility of the normal tissue and increasing the susceptibility of the tumor tissue to killing by the chemotherapy and/or radiation therapy, and (b) at least one carbohydrate in an amount effective to increase the absorption of glutamine by the subject.

Another embodiment of the invention provides a method of promoting apoptosis of cancer cells comprising: administering to a mammalian subject afflicted with cancer a therapeutically effective amount of a composition comprising glutamine or a pharmaceutically acceptable salt thereof and at least one carbohydrate in an amount effective to increase the absorption of glutamine by the subject.

Certain embodiments of the invention provide methods of increasing the protein levels, gene expression, or enzyme activity of Bad, Bax, or p21 in cells or tissue (e.g., breast tissue or serum) by administering to a mammalian subject a composition comprising (a) glutamine or a pharmaceutically acceptable salt thereof and (b) carbohydrate in an amount effective to increase the absorption of glutamine by the subject.

Other embodiments of the invention provide methods of decreasing the protein levels or gene expression of IGF-1, IGF-1R, or Akt in cells or tissue (e.g., breast tissue or serum) by administering to a mammalian subject a composition comprising (a) glutamine or a pharmaceutically acceptable salt thereof and (b) carbohydrate in an amount effective to increase the absorption of glutamine by the subject.

These increases or decreases of protein levels, gene expression, or enzyme activity can occur in cancer cells, such as breast cancer cells, in non-cancerous cells, or in extracellular tissue such as serum.

Another embodiment of the invention provides a method of enhancing natural killer cell activity in a mammalian subject comprising: administering to the subject a composition comprising (a) glutamine or a pharmaceutically acceptable salt thereof in an amount effective to increase natural killer cell activity in the subject and (b) carbohydrate in an amount effective to increase the absorption of glutamine by the subject. The subject can, for instance, be a cancer or HIV patient.

In the methods of the invention, the amount of glutamine administered to the mammalian subject can be, for instance, at least 0.5 mg/day/kg body mass of the subject or 0.2 to 3.0 g/day/kg body mass.

Including carbohydrate in the glutamine compositions enhances the absorption of glutamine by mammalian cells, thus allowing the administration of lower amounts of glutamine. Thus, in particular embodiments of the methods of the invention, the amount of glutamine administered to the subject is less than 0.5, less than 0.2, less than 0.1, or less than 0.05 g/day/kg body mass of the subject.

In particular embodiments of the invention, the carbohydrate comprises one or more monosaccharides or disaccharides. In other embodiments, the carbohydrate comprises a sugar alcohol.

In particular embodiments, the weight ratio of total carbohydrate to glutamine in the composition is 0.5:1 to 50:1.

In particular embodiments, the weight ratio of total carbohydrate to glutamine is at least 4:1 in an aqueous solution, either after preparation with an aqueous solvent or after delivery in an aqueous environment of the mammalian subject.

In particular embodiments, the composition comprises no more than 5 naturally occurring amino acids other than glutamine, no more than 3 naturally occurring amino acids other than glutamine, or no naturally occurring amino acids other than glutamine.

The mammalian subject can be a human.

When administered in association with radiation therapy, the compositions of the invention can be administered after, while, or before administering the radiation therapy. Likewise, when administered in association with chemotherapy, the compositions of the invention can be administered after, while, or before administering the chemotherapy.

The compositions of the invention can also be administered after or before surgically treating the subject for cancer.

The compositions of the invention can also be administered before, after, or while treating the subject with an anti-cancer biological agent. Examples of biological agents include proteins such as monoclonal antibodies, enzymes, or certain hormones; interferon; cells such as macrophages; or non-protein hormones.

Another embodiment of the invention is the use of glutamine to prepare a medicament effective to prevent metastasis in a mammalian subject afflicted with cancer.

Another embodiment of the invention is the use of glutamine to prepare a medicament effective to prevent recurrence of cancer, comprising: preparing a medicament comprising glutamine or a pharmaceutically acceptable salt thereof, wherein oral administration of the medicament to a mammalian subject in remission from cancer or undergoing anti-cancer therapy is effective to prevent recurrence of cancer in the subject.

Another embodiment of the invention is the use of glutamine and at least one carbohydrate to prepare a medicament effective to prevent the onset of cancer in a mammalian subject at risk of developing cancer, comprising: preparing a medicament comprising glutamine or a pharmaceutically acceptable salt thereof and at least one carbohydrate, wherein the medicament is effective at a lower dose of glutamine to prevent the onset of cancer in the mammalian subject by administration than an otherwise identical medicament lacking carbohydrate.

Another embodiment of the invention is the use of glutamine or a pharmaceutically acceptable salt thereof to prepare a medicament effective to protect non-mucosal tissue against damage from radiation therapy.

Another embodiment of the invention is the use of glutamine or a pharmaceutically acceptable salt thereof to prepare a medicament effective to protect skin of a mammalian subject afflicted with cancer and treated with chemotherapy against damage from chemotherapy.

Another embodiment of the invention is the use of glutamine or a pharmaceutically acceptable salt thereof to prepare a medicament effective to protect breast tissue of a mammalian subject afflicted with cancer and treated with chemotherapy against damage from the chemotherapy.

Another embodiment of the invention is the use of glutamine or a pharmaceutically acceptable salt thereof to prepare a medicament effective to prevent pain arising from a non-mucosal tissue in a mammalian subject afflicted with cancer and treated with chemotherapy and/or radiation therapy.

Another embodiment of the invention is the use of glutamine or a pharmaceutically acceptable salt thereof to prepare a medicament effective to protect skin of a mammal against radiation injury.

Another embodiment of the invention is the use of glutamine or a pharmaceutically acceptable salt thereof to prepare a medicament effective to promote healing of skin damaged by wound, injury, or infection comprising: preparing a medicament comprising glutamine or a pharmaceutically acceptable salt thereof, wherein the medicament is effective to promote healing in a mammalian subject of non-mucosal tissue damaged by wound, injury, or infection of the skin.

Another embodiment of the invention is the use of glutamine or a pharmaceutically acceptable salt thereof to prepare a medicament effective to treat cryptosporidiosis in a mammalian subject.

Another embodiment of the invention is the use of glutamine or a pharmaceutically acceptable salt and at least one carbohydrate to prepare a medicament effective to enhance the effectiveness of chemotherapy and/or radiation therapy, comprising: preparing a medicament comprising glutamine or a pharmaceutically acceptable salt thereof and at least one carbohydrate, wherein the medicament is effective at a lower dose of glutamine to enhance the effectiveness of chemotherapy and/or radiation therapy than an otherwise identical medicament lacking carbohydrate.

Another embodiment of the invention is the use of glutamine or a pharmaceutically acceptable salt thereof and at least one carbohydrate to prepare a medicament effective to increase the therapeutic index of chemotherapy and/or radiation therapy, comprising: preparing a medicament comprising glutamine or a pharmaceutically acceptable salt thereof and at least one carbohydrate, wherein the medicament is effective to increase glutathione concentration in at least one normal tissue and decrease glutathione concentration in tumor tissue, thereby reducing the susceptibility of the normal tissue and increasing the susceptibility of the tumor tissue to killing by the chemotherapy and/or radiation therapy, wherein the medicament is effective at a lower dose of glutamine to increase glutathione concentration in the at least one normal tissue and decrease glutathione concentration in the tumor tissue than an otherwise identical medicament lacking carbohydrate.

Another embodiment of the invention is the use of glutamine or a pharmaceutically acceptable salt thereof and at least one carbohydrate to prepare a medicament effective to promote apoptosis of cancer cells in a mammalian subject, comprising: preparing a medicament comprising glutamine or a pharmaceutically acceptable salt thereof and at least one carbohydrate, wherein the medicament is effective at a lower dose of glutamine to promote apoptosis of the cancer cells than an otherwise identical medicament lacking carbohydrate.

Another embodiment of the invention is the use of glutamine or a pharmaceutically acceptable salt thereof and at least one carbohydrate to prepare a medicament effective to increase Bad protein in cells of a mammalian subject, comprising: preparing a medicament comprising glutamine or a pharmaceutically acceptable salt thereof and at least one carbohydrate, wherein the medicament is effective at a lower dose of glutamine to increase the amount of Bad protein in the cells of the subject than an otherwise identical medicament lacking carbohydrate.

Another embodiment of the invention is the use of glutamine or a pharmaceutically acceptable salt thereof and at least one carbohydrate to prepare a medicament effective to increase Bax protein in cells of a mammalian subject, comprising: preparing a medicament comprising glutamine or a pharmaceutically acceptable salt thereof and at least one carbohydrate, wherein the medicament is effective at a lower dose of glutamine to increase the amount of Bax protein in the cells of the subject than an otherwise identical medicament lacking carbohydrate.

Another embodiment of the invention is the use of glutamine or a pharmaceutically acceptable salt thereof and at least one carbohydrate to prepare a medicament effective to increase p21 protein in cells of a mammalian subject, comprising: preparing a medicament comprising glutamine or a pharmaceutically acceptable salt thereof and at least one carbohydrate, wherein the medicament is effective at a lower dose of glutamine to increase the amount of p21 protein in the cells of the subject than an otherwise identical medicament lacking carbohydrate.

Another embodiment of the invention is the use of glutamine or a pharmaceutically acceptable salt thereof and at least one carbohydrate to prepare a medicament effective to increase the amount and/or activity of caspase-3 protein in cells of a mammalian subject, comprising: preparing a medicament comprising glutamine or a pharmaceutically acceptable salt thereof and at least one carbohydrate, wherein the medicament is effective at a lower dose of glutamine to increase the amount and/or activity of the caspase-3 protein in the cells of the subject than an otherwise identical medicament lacking carbohydrate.

Another embodiment of the invention is the use of glutamine or a pharmaceutically acceptable salt thereof and at least one carbohydrate to prepare a medicament effective to decrease Bcl-2 protein in cells of a mammalian subject, comprising: preparing a medicament comprising glutamine or a pharmaceutically acceptable salt thereof and at least one carbohydrate, wherein the medicament is effective at a lower dose of glutamine to decrease the amount of Bcl-2 protein in the cells of the subject than an otherwise identical medicament lacking carbohydrate.

Another embodiment of the invention is the use of glutamine or a pharmaceutically acceptable salt thereof and at least one carbohydrate to prepare a medicament effective to decrease IGF-1 protein in cells of a mammalian subject, comprising: preparing a medicament comprising glutamine or a pharmaceutically acceptable salt thereof and at least one carbohydrate, wherein the medicament is effective at a lower dose of glutamine to decrease the amount of IGF-1 protein in the cells of the subject than an otherwise identical medicament lacking carbohydrate.

Another embodiment of the invention is the use of glutamine or a pharmaceutically acceptable salt thereof and at least one carbohydrate to prepare a medicament effective to decrease IGF-1R protein in cells of a mammalian subject, comprising: preparing a medicament comprising glutamine or a pharmaceutically acceptable salt thereof and at least one carbohydrate, wherein the medicament is effective at a lower dose of glutamine to decrease the amount of IGF-1R protein in the cells of the subject than an otherwise identical medicament lacking carbohydrate.

Another embodiment of the invention is the use of glutamine or a pharmaceutically acceptable salt thereof and at least one carbohydrate to prepare a medicament effective to decrease Akt protein in cells of a mammalian subject, comprising: preparing a medicament comprising glutamine or a pharmaceutically acceptable salt thereof and at least one carbohydrate, wherein the medicament is effective at a lower dose of glutamine to decrease the amount of Akt protein in the cells of the subject than an otherwise identical medicament lacking carbohydrate.

Formulation of a Composition for Increasing Solubility and Absorption of an Amino Acid In accord with the present invention, at least one bioactive agent is combined with a carbohydrate in the presence of water, so as to form an aqueous solution. The carbohydrate can be, e.g., a monosaccharide, including, for example, allose, altrose, arabinose, dihydroxyacetone, erythrose, erythrulose, fructose, galactose, glucose, glyceraldehyde, gulose, lyxose, idose, mannose, psicose, ribose, ribulose, sorbitol, tagatose, threose, xylose, xylulose, and their respective hydroxy analogs, such as sorbitol from sorbose, mannitol from mannose, and xylitol from xylose. Alternatively, the carbohydrate can be a disaccharide, such as maltose or sucrose, or both, or their polymers, such as dextrins, maltodextrins, and high fructose corn syrup products. The carbohydrate carrier can also be composed of any combination of monosaccharides, disaccharides, or both, or of other carbohydrates. For many applications, the hydroxy analog of the sugar is preferable, particularly where a noncariogenic sugar is needed. Examples of hydroxy analogs include the sugar alcohols, xylitol, sorbitol, and mannitol.

Carbohydrate concentration, measured as weight/volume, in the solid composition is preferably 20% to 99%. At a certain concentration, the carbohydrate will complex and reduce the amount of free water available as a solute for the active agent, so that the transport of the active agent into the target cell is significantly increased.

A preferred embodiment of the composition provides a mixture of solids including about 5-50% w/w glutamine (most preferably L-glutamine), about 15-50% w/w carbohydrate carriers, including a disaccharide (most preferably sucrose), a sugar alcohol or polyol (most preferably sorbitol), and glycerin, an effective amount of buffer, or buffering compound (most preferably anhydrous monobasic sodium phosphate), about 1-5% w/w modified cellulose (most preferably Avicel® Cellulose Gel), with the remainder optionally comprising stabilizers and emulsifying agents (xanthan gum, carrageenan), preservatives (methylparaben, potassium sorbate), a defoamant (simethicone), and flavoring.

A more preferred embodiment provides approximately 5-15% w/w glutamine, 30-50% w/w carbohydrate carriers, including a disaccharide (most preferably sucrose), a sugar alcohol or polyol (most preferably sorbitol), and glycerin, with the remainder of dry solids comprising an effective amount of a buffer, or buffering compound (most preferably anhydrous monobasic sodium phosphate), modified cellulose (most preferably Avicel® Cellulose Gel), and optionally comprising stabilizers and emulsifiers (xanthan gum, carrageenan), preservatives (methylparaben, potassium sorbate), defoamants (simethicone), and flavoring.

A preferred liquid composition provides 5-25% w/v L-glutamine, 20-40% w/v carbohydrate carrier, including a disaccharide, a sugar alcohol, and glycerin, 5-10% w/v citric acid, and an effective amount of buffer (preferably 0.4-0.8% sodium phosphate), and the remainder water or alcohol-water, with optional stabilizers, preservatives, emulsifiers and flavorings.

Use of a carbohydrate carrier in the composition can increase the cellular absorption of the amino acid by at least ten times over direct administration of the amino acid in water. For example, a preferred aqueous composition of 38% w/v L-glutamine, 30% w/v sucrose, and 2.8% w/v sorbitol produced a 360-fold increase in glutamine uptake by CaCo cells (an epithelial mucosa cell line) over that obtained by use of an aqueous glutamine solution alone.

Excipients can also be added to the composition, provided that the necessary concentration of carbohydrate carrier is maintained. These can include a sweetener/solvent, such as glycerin; emulsifying and stabilizing agents, such as cellulose gel (for example, Avicel® Microcrystalline Cellulose Gel (FMC Corp., Philadelphia, Pa.)), xanthan gum or carrageenan; preservatives and stabilizers, such as citric acid, and methylparaben; a defoamant/base ingredient, such as simethicone; flavoring, or other ingredients which improve the stability and administration of the composition.

Delivery of an Increased Concentration of an Active Agent

The invention provides a method of delivery of increased concentrations of active agent to target cells in vivo or in vitro by a number of alternate routes. For example, the active agent can be mixed with a carbohydrate and water, and optionally gelling or thickening agents. The mixture can be administered as a solution, gel, or suspension. Where desired, undissolved materials can be removed by allowing the mixture to stand to allow undissolved particles to settle out, or can be centrifuged to isolate the supernatant. The supernatant solution can then be parenterally, or orally applied to target tissue, as by intravenous injection of infusion.

Glutamine and the compositions of the invention can be formulated as pharmaceutical compositions and administered to a mammalian host, such as a human patient in a variety of forms adapted to the chosen route of administration, e.g., parenterally (e.g., intravesously, topically, or enterally), or orally. It can also be administered by intramuscular, topical or subcutaneous routes, or by direct administration to the gastrointestinal tract, e.g., by enema or suppository. Preferably it is administered orally.

Application of the preparation can include, but is not limited to, topical administration by swabbing directly on a wound resulting from, for example, burn, trauma, or viral infection, e.g., in ointment, gel or liquid form, including administration by transdermal patches. In a preferred embodiment, the compositions of the invention are administered orally. The preparation can be applied to oral, nasal, and esophageal lesions by oral rinse, a gel, or an ingestible drink. For either oral rinse or ingestible drink, the carbohydrate carrier can be chosen from among a number of monosaccharides, disaccharides, or a combination of both, or from their polymers, such as dextrins, maltodextrins, and high fructose corn syrup products. Preferred carbohydrate carriers include sucrose, sorbitol and high fructose corn syrup products. Either a suspension or a drink can be provided as a dry mixture of carbohydrate carrier and an effective amount of amino acid, for reconstitution with water, juice, or other liquid. Bulk packaging of the dry mixture or packets containing single applications can be provided to a patient, health care provider, or any individual for whom the delivery of an increased concentration of active agent is desired. Before administration, the preparation can be constituted with water, juice, or other liquid to provide for easy administration and increase the absorption of glutamine into the epithelial tissue. Premixed liquid bulk or unit dosage forms can also be employed.

Application of the composition having a relatively low concentration of free water can also be accomplished by providing a lozenge or a form of candy or other medicated confection, such as a common lollipop, which utilizes a suitable carbohydrate carrier, such as sucrose or sorbitol, and a gelling or thickening agent, as needed. Chewing gum can also be used to deliver the carbohydrate carrier, such as sucrose, xylitol, sorbitol, or corn syrup solids, and amino acid. In a preferred form, the chewing gum can incorporate a central pocket of flavored syrup, composed of the appropriate mixture of carbohydrate carrier, such as xylose, sorbitol, or sucrose, and an effective amount of the amino acid. Formulations for preparation of chewing gum with a soft core portion are described in U.S. Pat. No. 4,352,823 (Cherukuri, et al., Oct. 5, 1982) and U.S. Pat. No. 4,352,825 (Cherukuri, et al., Oct. 5, 1982). Alternatively, a solid solution of a biologically active agent can be used in the preparation of chewing gum, lozenges, or a candy form such as a lollipop. Such solid solutions can be formed from comelts, coprecipitates, or by mechanical activation of the carbohydrate carrier and the biologically active agent. The candy or gum is placed in the mouth, where the surrounding fluids dissolve it. In this aqueous environment, the carbohydrate can proved the carrier to facilitate absorption of the glutamine into the epithelial cells of the oral cavity, the esophagus, and the stomach.

A toothpaste can also be formed to incorporate a carbohydrate carrier and active agent. Microencapsulation of ingredients in toothpaste compositions has been described in U.S. Pat. No. 4,348,378 (Kosti, Sep. 7, 1982), U.S. Pat. No. 4,071,614 (Grimm, Jan. 31, 1978), and U.S. Pat. No. 3,957,964 (Grimm, May 18, 1976), which describe the addition of encapsulated flavorings and anti-plaque ingredients to standard toothpaste preparations.

The composition of the present invention can also be delivered by suppository to epithelial tissues of the colon and rectum. Methods of preparation of suppository formulations are known in the art. One such method has been described in U.S. Pat. No. 4,439,194 (Harwood, et al., Mar. 27, 1984), which describes a water and drug delivery system for suppository use. An enema preparation can also be formed of a carbohydrate carrier and an amino acid, incorporating a sufficient amount of water to form an aqueous solution. A solid solution of the biologically active agent in the carbohydrate carrier can also be administered in a suppository or enema, drawing the aqueous component from the colon or rectum.

When delivery to the stomach is preferred, a filled capsule can be used. One such method has been described in U.S. Pat. No. 5,569,466 (Tanner, et al., Oct. 29, 1996), which describes the preparation of fill compositions for soft elastic gelatin capsules. Enteric coated capsules or tablets, or enteric coated microparticles can be employed to deliver the compositions to the upper or lower intestines.

The composition can be delivered in ice cream formulations, as well as frozen confections such as the common popsicle. Frozen formulations can be especially effective for the treatment of oral and esophageal ulcers, since they can combine, for example, both the beneficial effects of glutamine, as well as the soothing effects of the cold mixture.

Glutamine and the compositions of the invention may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compositions of the invention may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the glutamine to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Glutamine and the compositions of the invention can also be adapted for topical administration to the eye. An ophthalmologically acceptable vehicle such as an aqueous vehicle, a gel or an ointment is employed. Such vehicles can be buffered to about pH 5-6 and can also contain preservatives, thickeners and solubilizing agents as needed. Preferably, the compositions are formulated as eye drops. Exemplary liquid eye drop compositions contain 0.1% sodium hyaluronate (average molecular weight 1,800,000) or 0.1% Polysorbate 80 by weight to volume in water. The liquid compositions also may contain buffers, isotonic salts, and preservatives such as EDTA and thimerisol.

Ophthalmic aqueous compositions of the invention have ophthalmically compatible pH and osmolality. Preferably these compositions incorporate means to inhibit microbial growth, for example through preparation and packaging under sterile conditions and/or through inclusion of an antimicrobially effective amount of an ophthalmically acceptable preservative.

In a preferred embodiment, the composition is an in situ gellable aqueous composition, more preferably an in situ gellable aqueous solution. Such a composition comprises a gelling agent in a concentration effective to promote gelling upon contact with the eye or with lacrimal fluid in the exterior of the eye. Suitable gelling agents non-restrictively include thermosetting polymers such as tetra-substituted ethylene diamine block copolymers of ethylene oxide and propylene oxide (e.g., poloxamine 1307); polycarbophil; and polysaccharides such as gellan, carrageenan (e.g., kappa-carrageenan and iota-carrageenan), chitosan and alginate gums.

The term "in situ gellable" herein is to be understood as embracing not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye. Indeed, it can be advantageous to formulate a composition of the invention as a gel, to minimize loss of the composition immediately upon administration, as a result for example of lacrimation caused by reflex blinking. Although it is preferred that such a composition exhibit further increase in viscosity or gel stiffness upon administration, this is not absolutely required if the initial gel is sufficiently resistant to dissipation by lacrimal drainage to provide the effective residence time specified herein.

The compositions of the invention can also be administered to the eye by an ophthalmic delivery device. For instance, the compositions may be applied to a contact lens before the lens is placed in the eye, or after the contact lens is in the eye.

In any of these preparations, glutamine has a stable shelf-life and can be provided to the patient well in advance of the time of administration. The preparations can be stored in the clinic or the patient's home for administration as needed.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Method for Treating Mammalian Subjects by Enhancing Amino Acid Absorption

The composition of the present invention, and its various methods of delivery, can be used in a method for treating a variety of mammalian, especially human, physiologic disorders. The method is most effective for treatment of disorders involving epithelial tissue, particularly gastrointestinal epithelium (including oropharynx, esophagus, stomach, intestines and colon).

The method provides the previously described composition, a combination of therapeutically effective dosage of a selected amino acid, or a combination of amino acids, with an effective amount of carbohydrate carrier(s) which increase(s) aqueous solubility and cellular absorption of the amino acid or amino acids for administration to the epithelial tissue of the patient.

The invention is particularly useful for delivery of therapeutic levels of amino acids which exhibit limited aqueous solubility, such as the dietary amino acids tryptophan, tyrosine, glutamine, aspartic acid, asparagine, glutamic acid, histidine, isoleucine, leucine, methionine, and phenylalanine. Both D- and L-amino acids, as well as amino acids such as citrulline, g-aminobutyric acid, hydroxyproline, and omithine, for example, can be delivered by the method to increase cellular absorption.

Carbohydrate carriers useful for the composition administered in the method of the invention can be chosen from among the sugars, either monosaccharide or disaccharide, including, for example, D-allose, D-altrose, D-arabinose, D-erythrose, D-erythrulose, D-fructose, D-galactose, D-glucose, D-glyceraldehyde, D-gulose, D-lyxose, D-idose, D-mannose, D-psicose, D-ribose, D-ribulose, D-sorbose, D-tagatose, D-talose, D-threose, D-xylose, D-xylulose, maltose, lactose, and sucrose. In some patients or physiological conditions, as, for example, when it is important to choose a carbohydrate carrier which will not promote tooth decay or cause a sudden increase in blood glucose levels, it may be preferable to choose a polyol, or sugar alcohol, such as, for example, sorbitol, erythritol, maltitol, mannitol, or xylitol.

For children, particularly, a sugar alcohol may be a preferable carrier, and can produce added benefit beyond the desired therapeutic effect on the target tissue. For example, xylitol reduces the growth of Streptococcus pneumoniae and has been shown to have a preventive effect against acute otitis media when incorporated into chewing gum for children. (Uhari, M., et al., *Brit. Med. J.* (1996) 313(7066): 1180-1184.) Use of xylitol as a carbohydrate carrier for glutamine in a chewing gum formulation used to treat damaged oral or esophageal epithelial tissue after chemotherapy or bone marrow transplant can, therefore, also provide a protective benefit against a pathogenic organism.

The method comprises identification of physiologic disorders for which amino acid supplementation is indicated. More particularly, it provides a method for delivering increased intracellular amino acid supplementation to patients who exhibit symptoms of a physiologic disorder for which amino acid supplementation may be of therapeutic value. Numerous physiologic disorders, or diseases, have been linked, for example, to defective amino acid metabolism or defective absorption. In many situations, it is desirable to deliver large intracellular concentrations of an amino acid. In most situations, it is also preferable to do so by administering a limited dose of the selected amino acid or amino acids. This has not previously been possible, however, since many amino acids exhibit limited aqueous solubility and intracellular absorption—and must therefore be administered in large doses to achieve a desired effect. Physiological conditions for which amino acids supplementation has been indicated, and for which the method of the present invention is therefore beneficial for increasing intracellular delivery of amino acid supplements, are described below. These examples are not intended to limit the use of the method described herein, but are presented as examples of the wide variety of physiologic disorders for which the method of the present invention will be useful.

Enhancing Amino Acid Absorption for the Treatment of Children and Adults with Short Bowel Syndrome Short bowel syndrome is associated with surgical resection of the large intestine, and results in decreased surface area for absorption. The tissue of the bowel is often irritated, with accompanying symptoms such as cramping and diarrhea. An amino-acid-based complete infant formula has been demonstrated to be effective in improving feeding tolerance, eliminating the need for parenteral nutrition, and improving intestinal function in children with severe short bowel syndrome. (Bines, J., et al., *J. Pediatr. Gastroenterol. Nutr.* (1998) 26(2): 123-128.) The present invention provides a method for increasing absorption of amino acids, particularly those amino acids which exhibit limited aqueous solubility and cellular uptake (e.g., tryptophan, tyrosine, glutamine, aspartic acid, asparagine, glutamic acid, histidine, isoleucine, leucine, methionine, and phenylalanine), in both children and adults with short bowel syndrome. When used for the treatment of patients with short bowel syndrome, the combination of therapeutically effective concentrations of amino acids and an effective amount of carbohydrate carrier provides increased levels of cellular uptake of amino acids into the intestinal epithelium, thereby providing a greater benefit to the patient and decreasing the amounts of amino acids that must be administered in order to achieve satisfactory therapeutic levels.

The combination of amino acids and carbohydrate carrier can be administered by a variety of pharmaceutically acceptable routes, including tablets, caplets, or capsules coated for delivery to the intestines or colon, as well as enema solutions or suspensions. Therapeutic dosages can be determined by the patient's physician, taking into consideration the age, size, and nutritional status of the patient.

Enhancing Amino Acid Absorption in Dialysis Patients

Dialysis patients commonly exhibit malnutrition. However, supplementation with a mixture of 8 essential and 9 nonessential amino acids has been shown to improve both health and mood of dialysis patients. (Mastroiacovo, P., et al., *Clin. Ther.* (1993) 15(4): 698-704.) In the method of the present invention, a combination of amino acids, in therapeutically effective amounts, is combined with an effective amount of a carbohydrate carrier to enhance solubility and cellular uptake of the amino acids, thereby increasing the therapeutic effect of amino acid supplementation and decreasing the dosage of amino acid required to achieve therapeutic effect.

A preferred mode of administration for dialysis patients is an enteric coated capsule, caplet, tablet, or coated bead containing a therapeutically effective amount of each of a variety of amino acids in combination with an effective amount of a carbohydrate carrier, such as sucrose or a polyol such as xylitol or sorbitol. For administration to diabetic patients, the preferred carbohydrate carrier is a polyol.

Enhanced Absorption of Glutamine for the Treatment of Wounds

Glutamine is precursor for the synthesis of nucleotides. It is both an activator of protein synthesis, and an inhibitor of protein degradation. It is an activator of glycogen synthesis, as well as a metabolic substrate for rapidly dividing cells. It is also an energy source for epithelial cells. Treatment of wounds, whether superficial or non-superficial, with the composition described for enhancing amino acid absorption, increases the absorption of glutamine into epithelial tissues, promoting more rapid wound healing. In addition to promoting wound healing by increasing glutamine absorption, however, the method provides a treatment which protects the wound from infection with pathogenic organisms. Filling infected wounds with sugar has been a practice for centuries. Honey has long been known to have antibacterial properties, due, in part, to the hypertonic sugar concentration. (Basson, N. et al., *J. Dent. Assoc. S. Afr.* (1994) 49(7): 339-341; Jeddar, A., et al., *S. Afr. Med. J.* (1985) 67(7): 257-258; Willix, D., et al., *J. Appl. Bacteriol.* (1992) 73(5): 388-394.)

A combination of sugar and povidone-iodine has been effective in promoting rapid healing, reducing bacterial contamination, and filling of defects with granulation tissue when used to treat patients for wounds, burns, and ulcers. (Knutson, R., et al., *South Med. J.* (1981) 74(11: 1329-1335.) However, while adding to the antibacterial properties of the hypertonic sugar environment, povidone-iodine kills white blood cells.

Combining glutamine with a carbohydrate carrier, therefore, provides a dual benefit for wound care: the increased glutamine absorbed by the epithelial cells provides an energy source for the epithelial cells, promoting cell division and healing, while also providing an energy source for the white blood cells needed to protect the underlying tissues from bacterial invasion, and the carbohydrate carrier protects the surface of the wound from bacterial contamination by providing an environment in which the high osmotic pressure and low water availability prevents microbial growth.

For wound care, the combination of a therapeutically effective amount of glutamine and a carbohydrate carrier, preferably sucrose or honey, is applied topically as a semi-solid formulation of a high concentration of sugar mixed with water and glutamine. Alternately, the combination is provided as a thick syrup for topical application to the affected area. Another alternative method of application is to provide the formulation as a solid to be applied to the wound area, drawing its aqueous fraction from the wound environment. Such a preparation, if provided in powdered or crystalline form, can be easily placed in a first-aid kit or other emergency care kit for wound treatment.

The combination can be especially effective for the treatment of burns, where the primary goals of treatment are protection of the tissue from infection and rapid regeneration of new tissue.

Enhancing Glutamine Absorption for the Treatment of Mucositis and Stomatitis

Mucositis is an inflammatory reaction, characterized by burn-like lesions or ulcerative lesions of the epithelial tissue of the gastrointestinal tract from mouth to anus. It may result from exposure to either ionizing radiation or chemotherapeutic agents. Stomatitis is any inflammatory reaction affecting the oral mucosa, with or without accompanying ulceration. Mucositis, particularly, is often further complicated by infection of the ulcerative tissue.

Studies have previously shown that oral application of glutamine solutions can improve the symptoms accompanying mucositis in some bone marrow transplant patients and chemotherapy patients. (Skubitz, K., and P. Anderson, J. Lab. Clin. Med. (1996) 127(2): 223-228; Anderson, P., et al., Bone Marrow Transplant (1998) 22(4): 339-344; Anderson, P., et al., Cancer (1998) 83(7): 1433-1439; U.S. Pat. No. 5,545,668 (Skubitz, et al., Aug. 13, 1996); and U.S. Pat. No. 5,438,075 (Skubitz, et al., Aug. 1, 1995.) Using the composition and method described herein, increased and effective intracellular glutamine concentrations can be delivered to epithelial tissues of the gastrointestinal system for the treatment of mucositis or stomatitis without increasing the absolute glutamine dosage.

In the method of the invention, the composition can be provided, for example, as a mouthwash, swish and swallow preparation, lozenge, or hard candy for treatment of oral ulcerations. For esophageal ulcers, a drink, including a sugared drink, a milkshake, or a frozen slurry can be used. Biodegradable inserts can also be used to treat the mouth and throat. Children, as well as adults, with mucositis or stomatitis can be treated using any of these preparations, but may prefer a preparation of carbohydrate, glutamine, and flavorings delivered as a popsicle or in combination with sherbet, an ice, or ice cream. These methods of delivery provide the added benefit of soothing cold on the ulcerative tissue. A chewing gum preparation, preferably a chewing gum with a semi-solid or liquid center, can also be used for the treatment of oral and esophageal ulcers.

For gastric ulcer therapy, tablets, caplets, capsules, or coated beads containing the carbohydrate/glutamine composition can be administered. For intestinal ulcerations, coated tablets, caplets, capsules, or coated beads can be administered for either enteric or colonic delivery. Methods for providing enteric coatings or coatings for colonic delivery are known in the art and have been described previously herein.

Enhancement of Glutamine Absorption for the Treatment of Cryptosporidiosis

*Cryptosporidium parvum* is a leading cause of persistent diarrhea in developing countries. Due to its resistance to chlorine, it has also become a threat in some United States water supplies. Cryptosporidiosis is particularly problematic in AIDS patients, the elderly, and the very young, in whom it causes a severe, life-threatening diarrhea. *Cryptosporidium parvum* infects the intestinal tissue, but does not infect beyond the most superficial surface of the intestinal epithelium. In a piglet model, approximately two-thirds of the intestinal villus surface area was damaged during *Cryptosporidia* infection. In the remaining epithelial tissue, increased glutamine metabolism is associated with a sodium-hydrogen exchange coupled to a chloride transport mechanism. Because of its direct association with the chloride transport mechanism, glutamine can be particularly therapeutic for repair of tissue damaged by *Cryptosporidium* infection. (Guerrant, R., *Emerging Infectious Diseases* (1997) 3(1): 51-57.) Infected tissue has lost much of the absorptive surface area, however, and the method of the present invention, by treating the patient with the composition of carbohydrate carrier and a therapeutic dose of glutamine, enhances glutamine uptake in the remaining cells to compensate for the decreased absorptive surface area.

The composition can be administered using a coated capsule, tablet, or caplet for intestinal delivery. Alternately, the composition can be infused or administered as an enema solution to coat the intestinal lining with the glutamine/carbohydrate carrier and enhance glutamine absorption into the remaining intestinal epithelial cells.

The method can also be useful as a factor in disease prevention, since glutamine is known to provide a primary energy source for white blood cells, which migrate among the cells of the intestinal lining and are responsible for destruction of pathogenic organisms such as *C. parvum*. Enhancement of glutamine absorption into the epithelial and white blood cells by the method of the present invention therefore provides a method for improving the immune response while maintaining the structural integrity of the epithelial lining of the intestine. For patients at risk for *Cryptosporidium* infection, enteric-coated capsules can be administered to maintain epithelial cell integrity and improve the immune response.

Enhancement of Glutamine Absorption to Improve Post-Surgical Wound Healing in the Gastrointestinal Tract Following surgical resection within the oral cavity, the intestine, or bowel, epithelial tissue damage can be treated by the method of the present invention to increase tissue integrity and promote wound healing. Following oral surgery, a swish and swallow preparation, mouthwash, lozenge, candy, or chewing gum preparation containing the composition of the present invention can be provided to the patient to allow easy administration of a therapeutically effective dose of glutamine in combination with a carbohydrate carrier. Particularly in patients who have undergone oral surgery, non-cariogenic carbohydrate carriers are preferred. Such sugar carriers include, for example, maltitol, lactitol, sorbitol, and xylitol. The most preferable polyol carbohydrate carrier for incorporation into the composition is xylitol.

Following intestinal surgery, the composition can be administered in the form of a coated tablet, caplet, capsule, or coated bead. The tablet, caplet, capsule, or coated bead can be coated with an organic solvent, such as, for example, cellulose acetate phthalate, cellulose acetate trimellitate, cellulose acetate succinate, hydroxypropyl methyl cellulose phthalate, hydroxypropyl methyl cellulose acetate succinate, and carboxy methyl ethyl cellulose, for enteric delivery. A tablet, caplet, or capsule can be coated with an acrylic-based resin to dissolve at higher pH (pH 7) to provide delivery to the distal ileum and colon. Alternatively, delivery of the glutamine/carbohydrate carrier composition can be provided in the form of a suppository, using a base such as cocoa butter or other glyceride, or as a rectal tablet without a conventional suppository base. Such compositions for suppository use have been described by Mizuno, et al., in U.S. Pat. No. 4,462,984, and Harwood, et al., in U.S. Pat. No. 4,439,194.

For treatment of diabetic patients, xylitol is the preferred carbohydrate carrier, as sorbitol is not absorbed in the intestine and could cause added intestinal discomfort.

Enhancement of Glutamine Absorption for Treatment of Low Birth Weight Infants

Neu, et al., have reported that very-low-birth-weight neonates who receive enteral glutamine supplementation have an increased survival rate. (J. Pediatrics, (1997) 131(5): 691-699.) The method of the present invention provides increased therapeutic intracellular glutamine dosages with decreased actual glutamine administration. In low-birth-weight neonates, particularly, achievement of the desired effect with smaller doses of nutrient can be essential.

For delivery of the composition, an enteral feeding tube is preferred. Any one of a number of carbohydrate carriers can be chosen, although sucrose and high fructose corn syrup are preferred. The therapeutic dosage of glutamine can be determined by the individual physician, using standard means of dosage calculation, bearing in mind that glutamine absorption is enhanced by combination with the carbohydrate carrier to levels of at least ten times higher than that achieved by administration of glutamine alone. Excipients can be added to the feeding formula, including flavorings and stabilizers. Added nutrients can also be included, including vitamins, amino acids, and recommended nutrients such as lactoferrin.

Enhancement of Glutamine Absorption to Treat Dermatological Lesions of Viral and Bacterial Origin A number of viral illnesses can be recognized by epithelial lesions. Among these are, for example, herpetic lesions around the mouth, the lesions associated with impetigo, and the painful lesions known as shingles, characteristic of varicella-zoster virus. The method of the present invention can be used to treat such lesions by topically applying the glutamine/carbohydrate carrier composition to the affected area. The glutamine component of the composition aids in healing by providing energy to the epithelial cells, while the sugar provides antibacterial properties to protect the damaged or infected tissue from further infection.

For topical application, a lotion or cream is preferred, incorporating glutamine, a carbohydrate carrier, and excipients such as stabilizing agents, gelling agents, or thickening agents.

Enhancement of Glutamine Absorption to Treat Patients Infected with Human Immunodeficiency Virus Gastrointestinal lymphoid tissue harbors more than 90% of the total lymphocytes in the body. Studies have shown that the gastrointestinal epithelium contains a large population of $CD34^+$ CD4-progenitors. (Mattapallil, J., et al., *J. Virol.* (1999) 73(5): 4518-4523.) The gastrointestinal tract has also been demonstrated to be a major site of $CD4^+$ T cell depletion and viral replication in simian immunodeficiency virus infection. Other studies have shown that glutamine enhances production of T lymphocyte-derived cytokines. (Yaqoob, P. and P. Calder, Cytokine (1998) 10(10): 790-794.) Enhancing glutamine absorption into the intestinal mucosa by the method of the present invention therefore can provide a therapeutic benefit to HIV-infected patients, particularly those patients who are in the early stages of infection. Enhancement of the cytokine response to the viral infection can contribute to viral destruction by the immune system at the site of significant viral replication.

The glutamine/carbohydrate carrier composition can be administered in the form of an enteric-coated tablet, caplet, capsule, or coated bead. Suitable sugar carriers will preferably include, for example, sucrose, glucose, high fructose corn syrup, and xylitol.

Daily administration of recommended dietary levels of glutamine is preferred, since administration of this quantity of glutamine by the method of the present invention can result in an increased delivery of glutamine to the intestinal epithelium by a factor of, for example, 10-30×. Therefore, administration of more moderate amounts can produce an even greater intracellular concentration of glutamine than has been previously been achieved by administration of higher dosages of glutamine alone.

Enhancement of Glutamine Absorption for Cancer Therapy

Glutamine supplementation increases selectivity of both radiation therapy and chemotherapy for tumor cells. Glutamine supplementation decreases tumor growth, and in combination with chemotherapy or radiation therapy, enhances the decrease in tumor volume. It is also shown herein that glutamine supplementation enhances natural killer cell activity.

Glutamine supplementation enhances tolerance to chemotherapeutic agents and to radiation therapy. It is believed that this is accomplished by providing normal cells with an energy source and a means to accomplish cellular repair, The composition and method of the present invention provide increased glutamine absorption into gastrointestinal epithelial cells. Once absorbed into these cells, more glutamine is made available to circulate to other tissues of the body.

Enhancement of absorption of glutamine also provides a means to increase glutathione production in the intestine. Cancer therapy can therefore consist of, or be enhanced by, daily administration of glutamine in admixture with an amount of carbohydrate carrier, such as, for example, sucrose, glucose, xylose, xylitol, high fructose corn syrup or corn syrup solids effective to increase glutamine absorption into the gastrointestinal epithelium. The composition and method can be used for both human and veterinary cancer therapy.

Daily doses of glutamine will be determined by the individual patient's physician, taking into consideration factors which are known by those of skill in the art to affect dosage calculation, such as, for example, body size and age. Recommended daily doses of glutamine for cancer therapy are preferably at least at the maximum dietary intake of 3-4 grams per day, although lower doses can be administered, since the composition and method of the present invention increase glutamine absorption by at least a factor of ten, and more preferably, 100.

Other Uses for a Method for Increased Amino Acid Absorption

Although the method for treating physiological disorders in patients has been described primarily in terms of administration of glutamine, the invention is not intended to be limited to a method of administering enhanced levels of glutamine alone. For example, D-serine has been demonstrated to be therapeutic for the treatment of schizophrenia when administered in conjunction with antipsychotic medications. (Tsai, G., et al., *Biol. Psychiatry* (1998) 44(11): 1081-1089.) Enhanced absorption of D-serine into the intestinal epithelia after oral administration, can, therefore, provide a method for increasing available D-serine for systemic circulation. Canavan disease, an autosomal genetic disorder, is proposed to benefit from supplementation of dietary aspartic acid. (Baslow, M. And T. Resnik, *J. Mol. Neurosci.* (1997) 9(2): 109-125.) Early detection of the disease, therefore, can be accompanied by aspartic acid supplementation by the method of the present invention to enhance uptake of aspartic acid, an amino acid with an aqueous solubility of only 0.778 g/100 g at 25° C., to protect against the progressive degeneration of the brain which is characteristic of the disease.

These are only two examples of a number of physiologic conditions which can be therapeutically treated using enhanced amino acid absorption provided by the method of the present invention. As amino acids are identified as having therapeutic value, dietary supplementation can be further enhanced by providing the amino acid supplement in combination with a carbohydrate carrier as described by the method of the invention.

Veterinary Use for Enhanced Amino Acid Absorption into Epithelial Cells

The early-weaned pig develops intestinal atrophy, and glutamine supplementation has been proposed to prevent intestinal epithelial damage and provide a benefit in swine production. (Wu, et al., *J. Nutr.* (1996) 126 (10): 2578-84.) The composition and method of the present invention can be used to enhance amino acid absorption into those epithelial tissue cells, thereby decreasing costs associated with amino acid supplementation. The composition and method are also useful for veterinary treatment of dogs and other mammals in whom chemotherapy has been initiated. For example, doxorubicin, associated with gastrointestinal ulcers in human chemotherapy patients, is the recommended treatment for a number of other mammalian cancers, including canine hemangiosarcoma. The composition and method of the present invention provide enhanced amino acid absorption into the damaged epithelium of the mammalian subject, as well as increasing systemically available amino acid by increasing absorption into the gastrointestinal epithelium.

The invention will now be illustrated by the following non-limiting examples.

EXAMPLE 1

Evaluation of Cellular Uptake of Glutamine in Combination With Sucrose and Sorbitol The composition of the present invention has been shown to improve solubility and cellular absorption of an amino acid, glutamine, into human gastrointestinal epithelial cells, as illustrated in the following example.

1. Materials and Methods

Distilled, deionized water (107 ml) was added to 207 grams of a mixture of sucrose, sorbitol, and glutamine with excipients (Aesgen-14) as listed in Table 1.

TABLE 1

| Aesgen-14 (AES-14) | | | |
| --- | --- | --- | --- |
| L-glutamine | 240.0 Kg | 57.94 w %* | 50.00% w/v** |
| Sucrose | 144.0 Kg | 34.77 w % | 30.00% w/v |
| Crystalline Sorbitol | 13.44 Kg | 3.24 w % | 2.80% w/v |
| Glycerin | 14.0 Kg | 2.92 w % | 2.52% w/v |
| Sodium Phosphate Monobasic (Anhydrous) | 2.6 Kg | 0.63 w % | 0.54% w/v |
| Avicel Cellulose Gel Type CL-611 | 874.0 g | 0.18 w % | 0.17% w/v |
| Citric Acid (Anhydrous) | 280.0 g | 0.07 w % | 0.06% w/v |
| Xanthan Gum | 230.0 g | 0.05 w % | 0.04% w/v |
| Carrageenan | 230.0 g | 0.05 w % | 0.04% w/v |
| Artificial Flavor | 230.0 g | 0.05 w % | 0.04% w/v |
| Methylparaben | 207.0 g | 0.04 w % | 0.04% w/v |
| Potassium Sorbate Powder | 180.0 g | 0.04 w % | 0.04% w/v |
| 30% Simethicone Emulsion | 115.0 g | 0.02 w % | 0.02% w/v |

*Weight percents are expressed as percent of total weight of dry ingredients for reconstitution with water in a 240 ml bottle.
**Weight/volume percents are expressed as percent of total volume in aqueous mixture.

As a control, 200 milliliters of distilled, deionized water was added to 50 grams of L-glutamine (Ajinomoto, Raleigh N.C.) and mixed by agitation. Both samples were allowed to stand for 1 day at room temperature. The supernatant was decanted from the residue and used for the cellular uptake determination.

On Day 1, cells from a human gastrointestinal epithelial cell line (CaCo) were plated at a density of $0.5 \times 10^6$ cells per well in a 6-well tissue culture dish. On Day 2, culture media was replaced with either normal growth medium or medium deficient in L-glutamine.

On Day 3, cells cultured in both normal growth medium ("normal") and L-glutamine deficient growth medium ("starved") were evaluated for comparison of glutamine uptake using the Aesgen-14 solution in parallel with the L-glutamine solution, according to the following protocol: Two milliliters of test material (either Aesgen-14 or L-glutamine solution) was added to the appropriate wells, then incubated at 37° C. At time points 0, 10, 20, 40, and 60 seconds the test material was aspirated and the cells washed three times (3×) with chilled (4° C.) phosphate buffered saline (PBS), followed by the addition of 1.0 ml of perchloric acid. Cells were harvested by scraping, then aspiration by pipet into a 1.7 ml tube.

The harvested cells were sonicated for 10 seconds, and 500 μl of sonicated cells were transferred into a 1.7 ml tube. The perchloric acid was neutralized by the addition of 130 μl of 2M KHCO$_3$, and the resulting mixture was frozen overnight at −80° C.

Upon thawing, the sample was centrifuged for 10 minutes at 14,000 rpm and the supernatants were transferred to new 1.7 ml tubes and frozen at −80° C. The resulting clarified samples were thawed and diluted 1:3 with deionized water. Fifty microliters were withdrawn, added to 10 microliters complete o-phthaldialdehyde (Sigma P-0532), and mixed by agitation. After incubation for two minutes at room temperature, a 20 μl sample was injected on a Hypersil® C18 Elite 5 μm HPLC column using 70:30 acetonitrile:water as the mobile phase. Glutamine levels, measured as μg/ml, were detected at 340 nm.

2. Results

Results are shown in Table 2 as μg/ml mean cellular glutamine uptake:

TABLE 2

|  | Incubation Time (Seconds) | | | | |
| --- | --- | --- | --- | --- | --- |
|  | 0 | 10 | 20 | 40 | 60 |
| Normal cells + Aesgen 14 | 1.00 | 1568.55 | 900.60 | 1185.88 | 1765.13 |
| Normal cells + L-glutamine | 3.53 | 10.30 | 2.48 | 3.23 | 4.85 |
| Starved cells + Aesgen 14 | 0.00 | 613.10 | 672.93 | 1213.40 | 1053.85 |
| Starved cells + L-glutamine | 1.33 | 1.43 | 1.49 | 2.23 | 49.96 |

As summarized above, glutamine uptake is significantly increased in both normal cells (363×) and in starved cells (21×) in cells treated with Aesgen-14 as compared to cells treated with aqueous L-glutamine alone.

EXAMPLE 2

Effect of AES-14 on Drug Uptake and Permeability

The cellular uptake and permeability-enhancing effect of a sucrose-containing vehicle on five model drugs (saturated solutions of L-glutamine, L-asparagine, glycylsarcosine, and acyclovir; and a half-saturated solution of L-glutamine) across Caco-2 cell monolayers were measured in this experiment. Uptake and permeability of each compound was measured in the apical-to-basolateral direction, with and without vehicle.

Methods

Materials. Two amino acids (L-glutamine, L-asparagine), a dipeptide (glycylsarcosine), and a therapeutic agent (acyclovir) with low permeability were studied. Each compound was tritiated. $^{14}$C-mannitol was used as an evaluation of monolayer/cell integrity (i.e. as a low uptake/permeability marker).

Uptake and Permeability Assessments. Compound cellular uptake into and permeability across Caco-2 monolayers was measured. Caco-2 monolayers were grown using a recently developed, rapid culture system, that requires 4 days rather than 21 days. Lentz et al., (2000), Int. J. Pharm., 200(1): 41-51.

Uptake and permeability studies were conducted in duplicate at 37° C. and 50 oscillations per min across Caco-2 monolayers in either (a) blank AES-14 (i.e., AES-14 without L-glutamine) or (b) Hank's balanced salt solution (HBSS) containing 10 mM HEPES buffer (solution pH=6.8). HBSS was used when no pharmaceutical vehicle was present for each of the four compounds. Blank AES-14 was the matrix for L-asparagine, glycylsarcosine, acyclovir, and "half-saturation" L-glutamine studies when a vehicle effect is considered. AES-14, which contains L-glutamine, was studied for L-glutamine. Monolayer integrity was monitored using $^{14}$C-mannitol permeability. Mannitol uptake was also studied.

Uptake and permeability studies were conducted using Transwell® inserts in the apical to basolateral direction, at intervals of 10 sec., 60 sec., and 5 min. Donor solution included a nine saturated systems (except half strength L-glutamine) were the source solutions for the uptake/permeability studies. Saturated solutions were obtained by utilizing 5.4 g L-glutamine/100 ml, 1 g L-asparagine/10 ml, 2 g glycylsarcosine/10 ml, and 16 mg acyclovir/10 ml system concentrations (Kristol, (1999), J. Pharm. Sci., 88: 109-110), wherein excess solid solute was present to assure saturation:

Saturated solution of L-glutamine in HBSS (5.4 g/100 ml)
Saturated solution of L-asparagine in HBSS (1 g/10 ml)
Saturated solution of glycylsarcosine in HBSS (2 g/10 ml)
Saturated solution of acyclovir (16 mg/10 ml) in HBSS AES-14
Saturated solution of L-asparagine in blank AES-14 (1 g/10 ml)
Saturated solution of glycylsarcosine in blank AES-14 (16 mg/10 ml)
2.3 g/100 ml L-glutamine in blank AES-14 (i.e. half-saturated L-glutamine).

$^{14}$C-mannitol and $^{3}$H-drugs were quantified by liquid scintillation counting. For uptake studies, at designated time points (10 sec, 60 sec, and 5 min), the donor solution was aspirated off. The cell monolayer was washed twice with ice cold HBSS to remove any residual binding and then dissolved in 1 ml of the cell solubilizing agent, Solvable®. The cell lysate (0.5 ml) was added to 5 ml scintillation cocktail (Econosafe®) and counted on liquid scintillation counter (Beckman LS5801, Columbia, Md.). For permeability studies, 0.5 ml of received solution was added to 5 ml scintillation cocktail (Econosafe®) and counted on liquid scintillation counter.

Since saturated solutions of unknown concentration of drugs were used, absolute uptake could not be calculated. Hence, the vehicle effect on uptake is considered below (FIGS. 3-7) in terms of the relative drug uptake into cell monolayer from vehicle vs non-vehicle (i.e., ratio of uptake, after normalized for slight differences in radiolabel tracer).

Permeability (3) in each experiment was calculated (FIGS. 8-12) using eq 1:

$$P = \frac{\frac{dM}{dt}}{A \cdot C_d}$$

where P is permeability, dM/dt is rate of drug mass accumulation (i.e., radioactivity) in receiver compartment, A is area, and Cd is donor drug concentration (i.e., radioactivity). Polli et al., (1998), Pharm. Res., 15: 47-52. Permeability is an absolute measure (units of cm/Sec or velocity) and can be determined even though the absolute drug concentrations were not known.

Results

Figure 7:
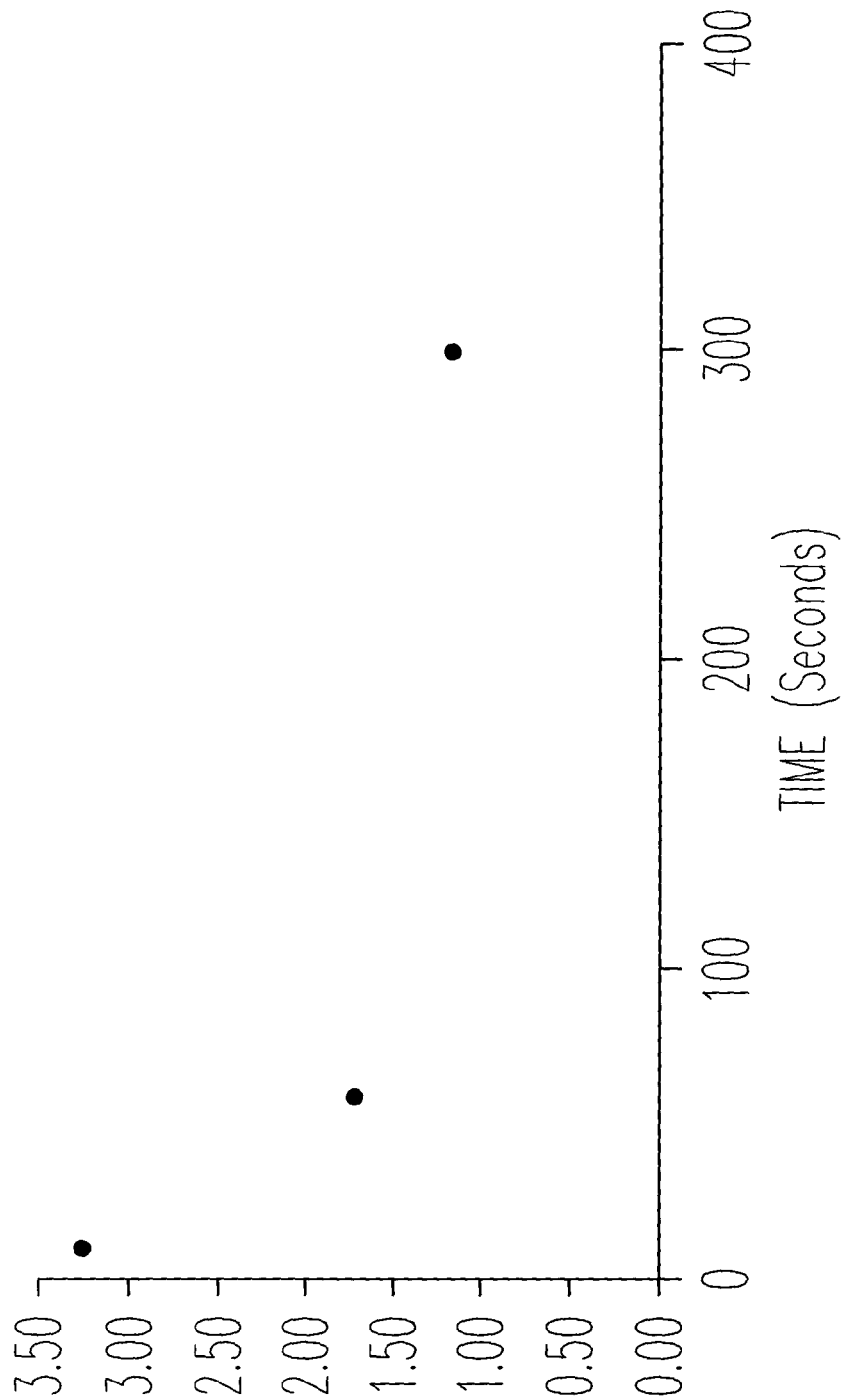
FIG. 7 depicts the relative effect of vehicle on L-glutamine cellular uptake (from half saturation).
Figure 8:
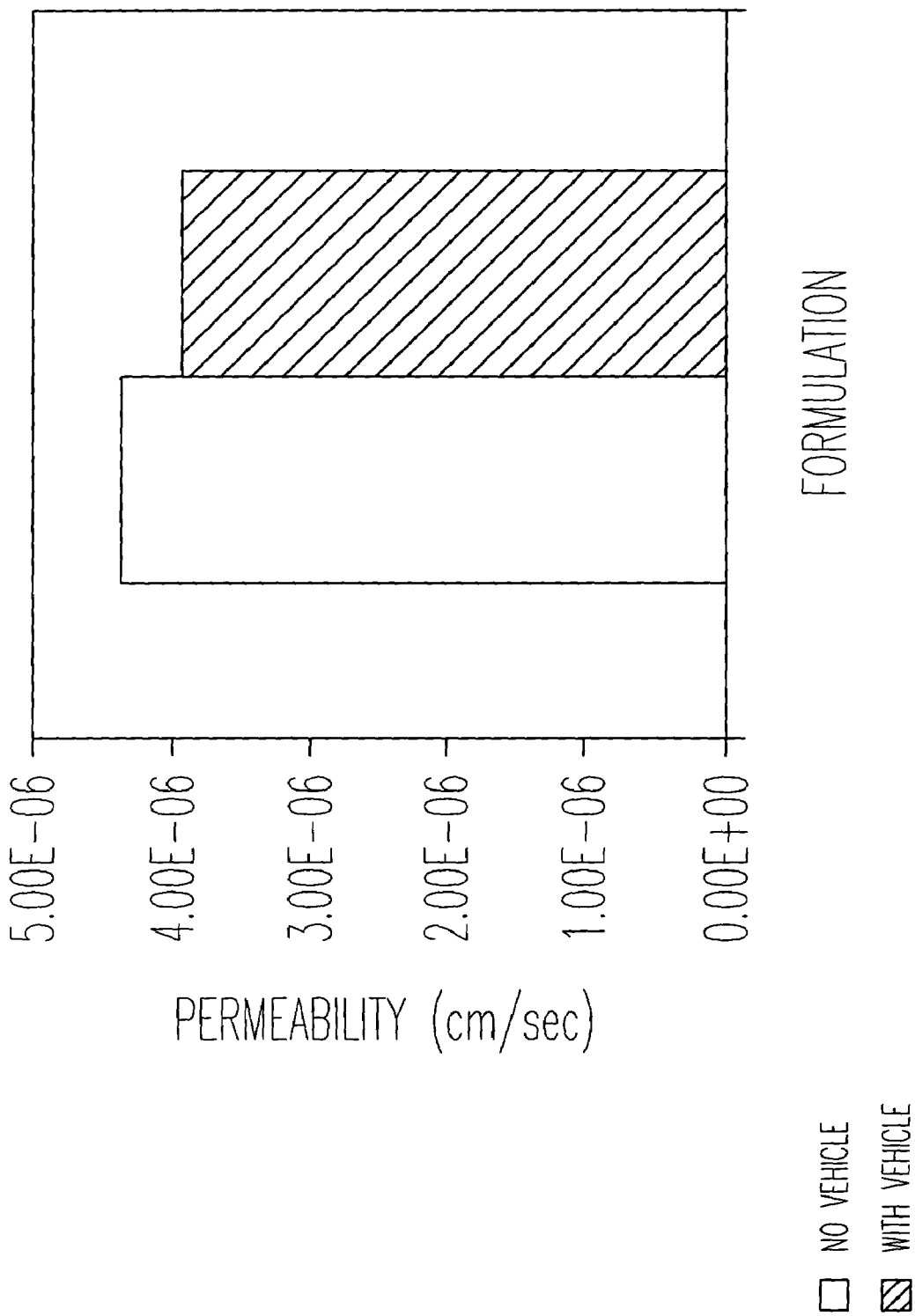
FIG. 8 depicts the CaCo-2 permeability of L-glutamine.
Figure 9:
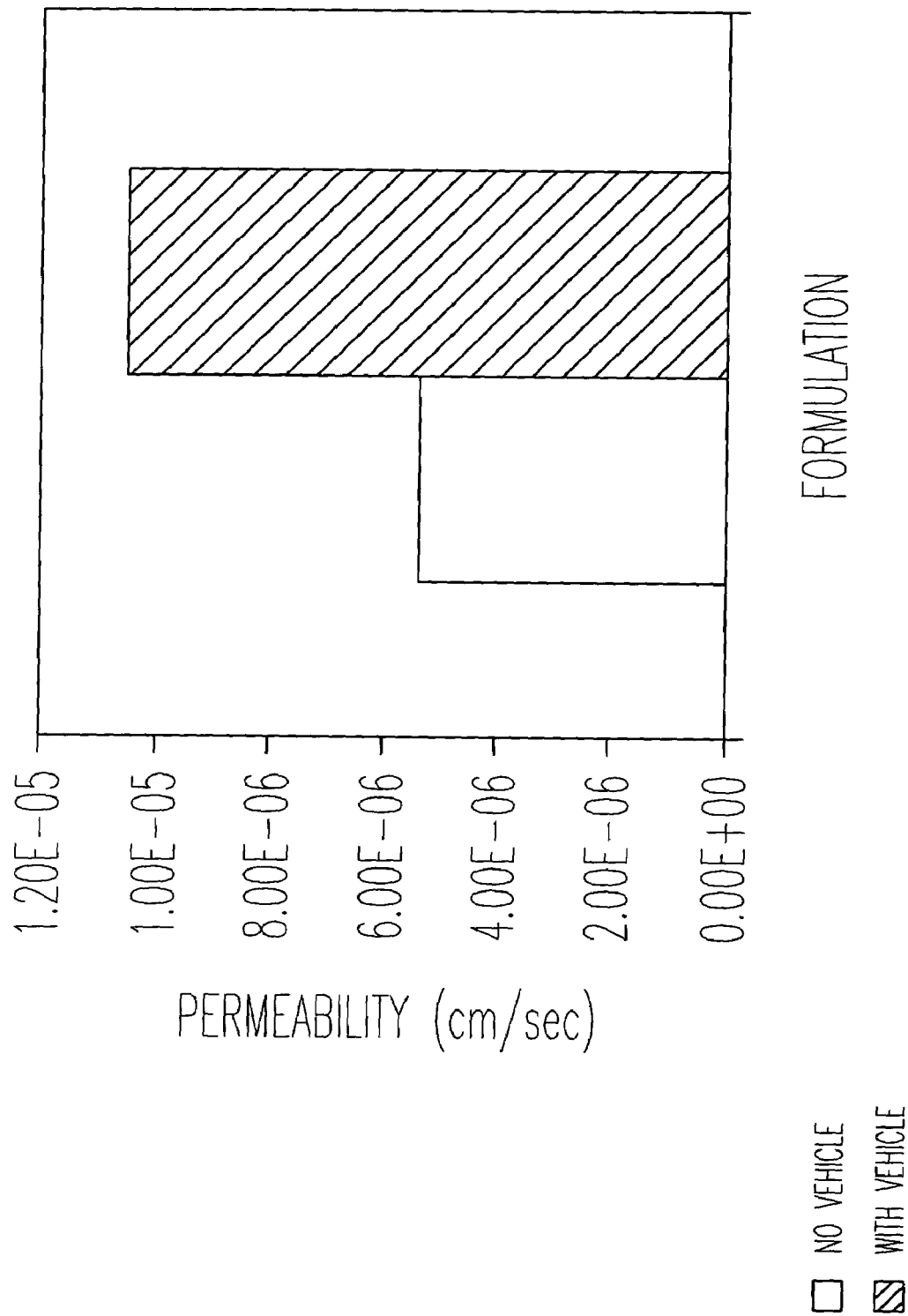
FIG. 9 depicts the CaCo-2 permeability of glycylsarcosine.
Figure 10:
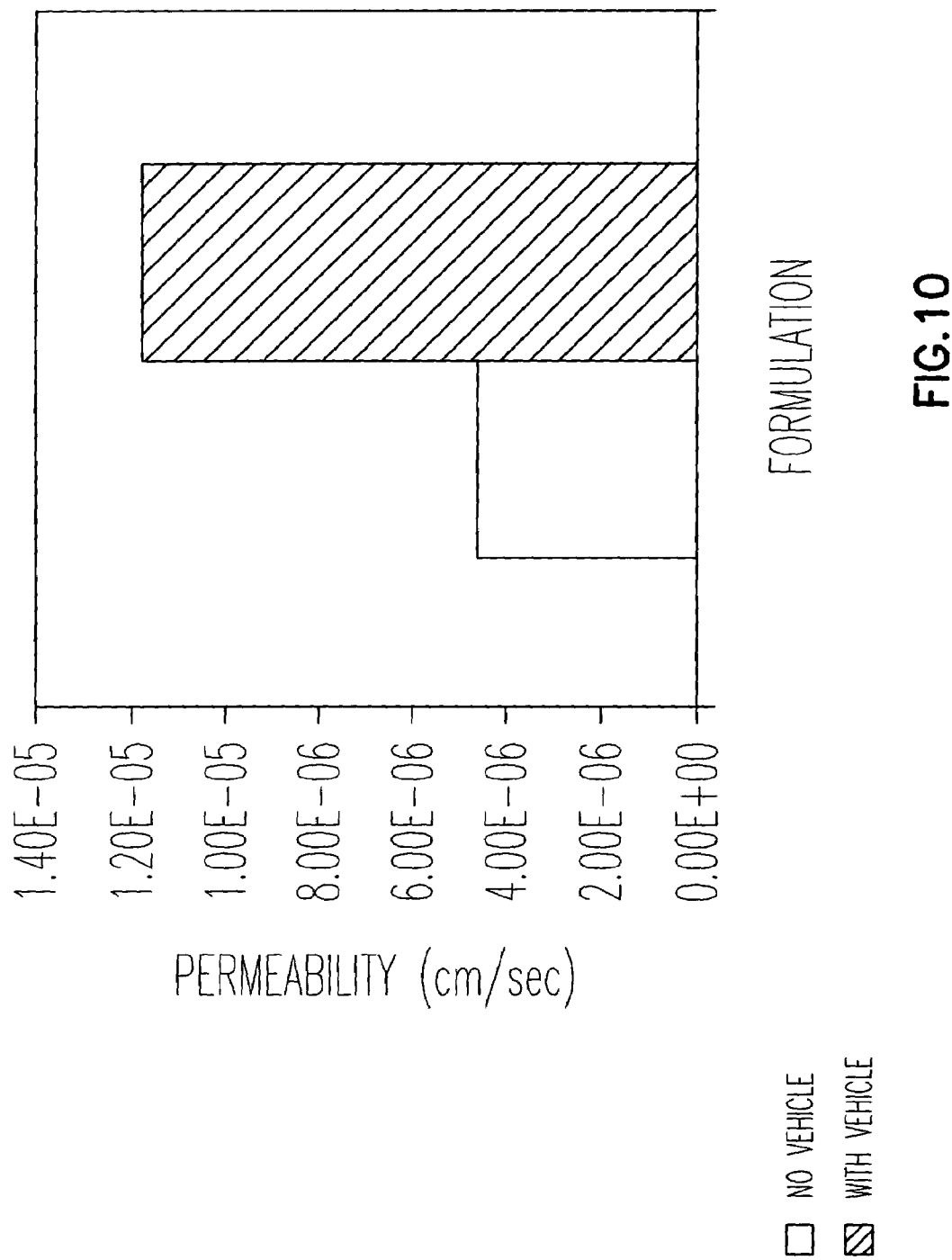
FIG. 10 depicts the CaCo-2 permeability of L-asparagine.
Figure 11:
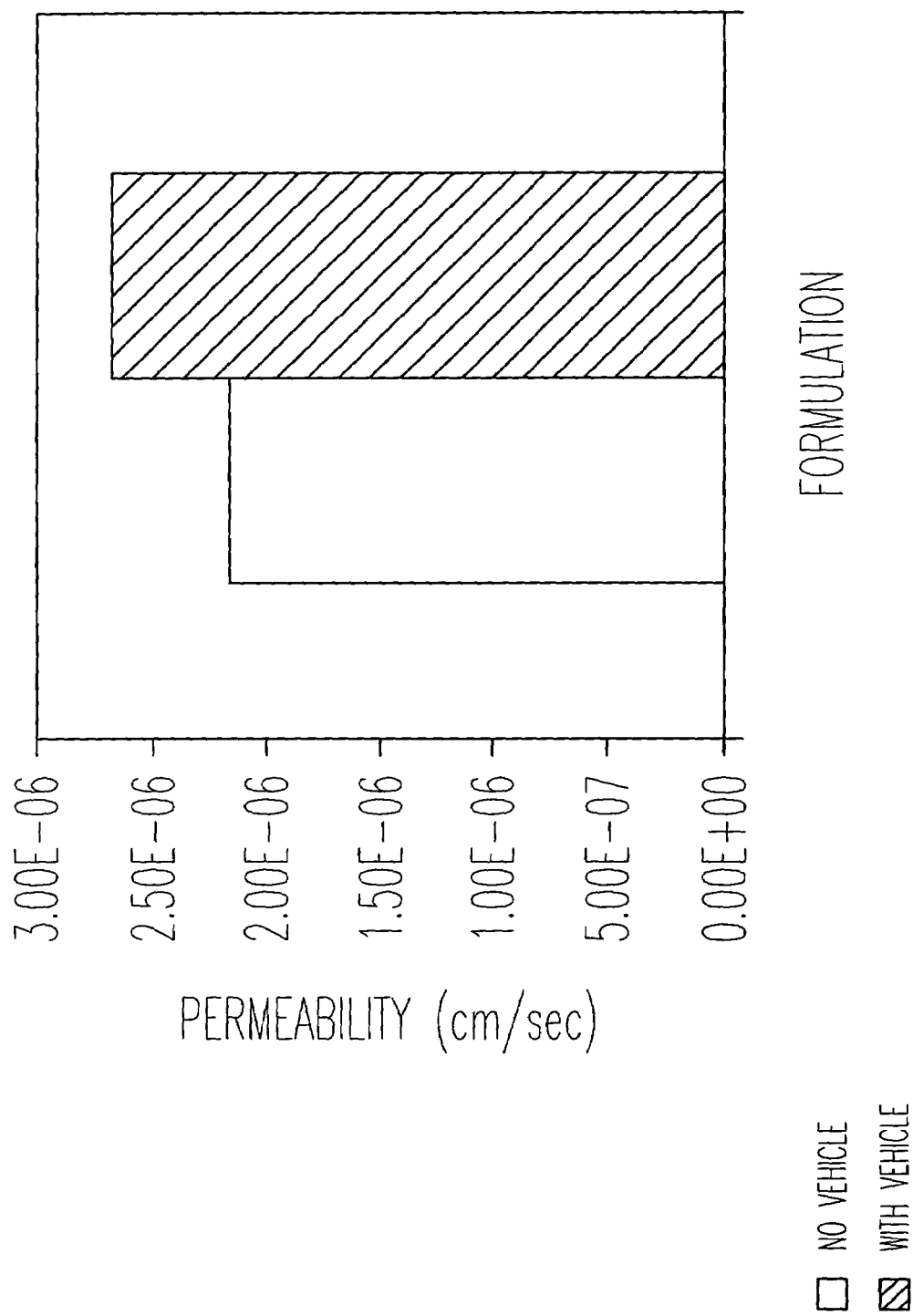
FIG. 11 depicts the CaCo-2 permeability of acyclovir.
Figure 12:
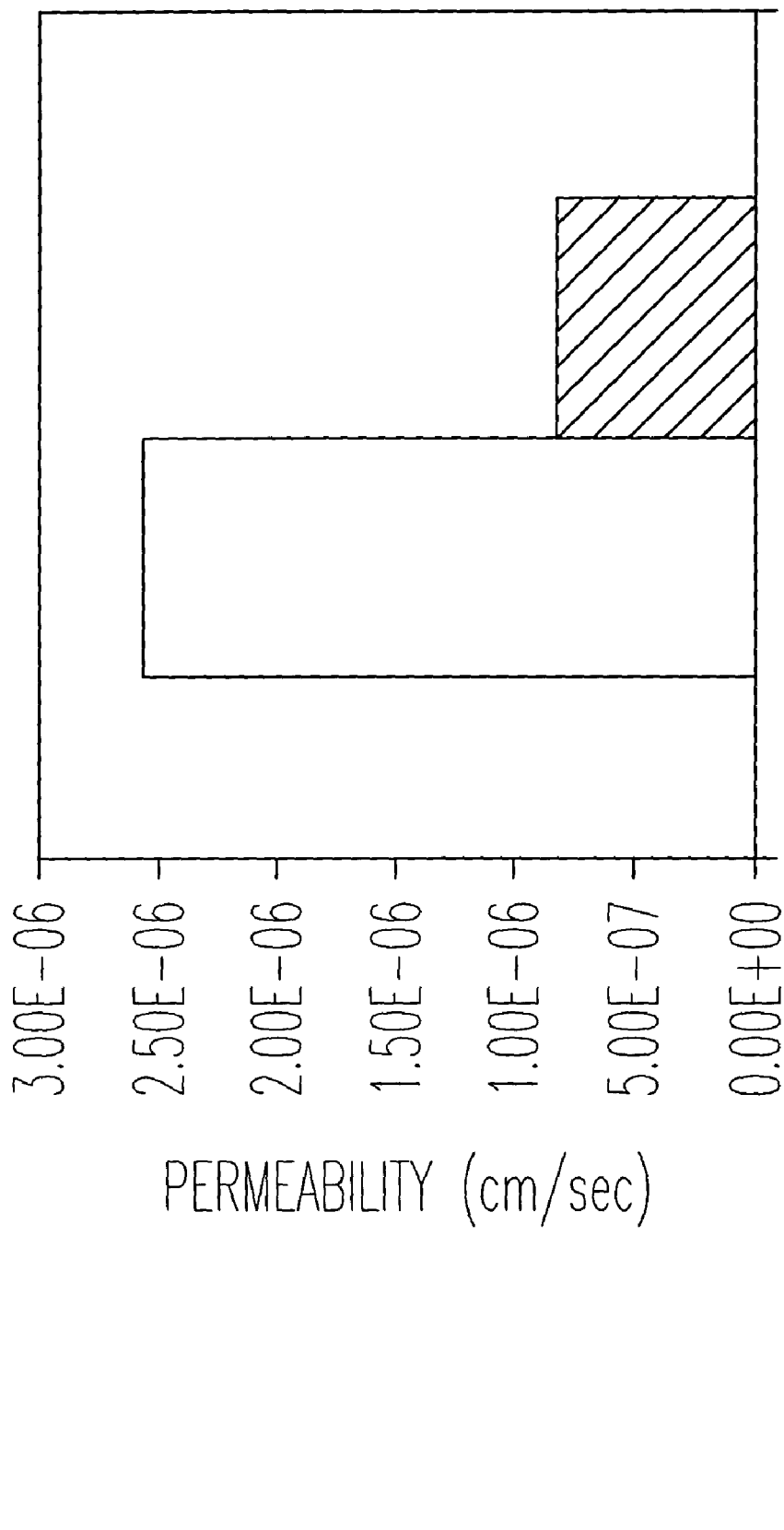
FIG. 12 depicts the CaCo-2 permeability of L-glutamine (from half saturation).

Uptake. In FIGS. 3-7, the relative effect of vehicle on L-glutamine, glycylsarcosine, L-asparagine, acyclovir, and L-glutamine (half-strength) uptake into cells is shown. If uptake (normalized for slight differences in donor radiolabel) were identical from each vehicle and HBSS, the relative uptake would be 1.0. For all four drugs and half-strength L-glutamine, the relative uptake exceeded 1.0. In FIGS. 3-6, for L-glutamine, L-asparagine, glycylsarcosine, and acyclovir, vehicle enhanced cellular drug uptake about four-fold. To perhaps a lesser extent, vehicle enhanced half-strength L-glutamine (FIG. 7).

In Table 2 below, vehicle had no effect on mannitol relative uptake. These mannitol studies, which were performed simultaneously with those in FIG. 3-7, indicated the vehicle effect differentiates mannitol from the other compounds, in terms of uptake enhancement. Thus, the uptake of the saccharides per se is apparently not increased, and the term "biologically active agent" can be read to exclude the saccharides present in the solution, dispersion, or gel.

TABLE 2

Relative Effect of Vehicle on Mannitol Cellular Uptake

| Time (sec) | L-glutamine study | Glycyl-sarcosine study | L-argine study | Acyclovir study | L-glutamine (half-strength) study |
|---|---|---|---|---|---|
| 5 | 0.52 | 0.83 | 1.65 | 1.24 | 1.20 |
| 60 | 0.80 | 1.51 | 0.77 | 0.85 | 0.57 |
| 300 | 0.63 | 1.06 | 0.43 | 0.43 | 0.30 |

Permeability. In FIGS. 8-12, the relative effect of Aesgen-14 vehicle on L-glutamine, glycylsarcosine, L-asparagine, acyclovir, and L-glutamine (half-strength) permeability is shown. Unlike the uptake data presented above, which shows the relative vehicle effect on uptake (i.e., the ratio of uptake with vehicle vs. without vehicle), permeability is an absolute measurement, and is calculated for each formulation (no vehicle and with vehicle). Since two-fold variation in permeability is within typical experimental variation, these results indicate that vehicle had no effect on permeability. Similarly, vehicle had no effect on mannitol permeability (Table 3).

Figure 13:
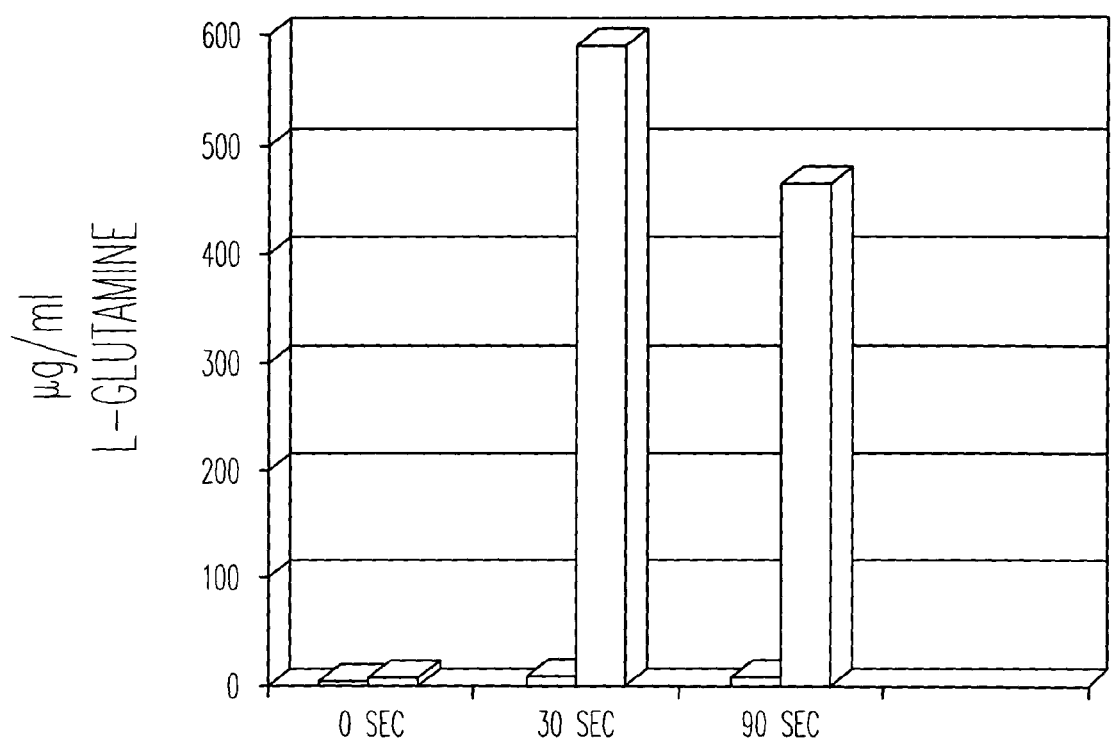
FIG. 13 depicts the effect of Aesgen-14 on L-glutamine uptake into human fibroblasts (right boxes) vs. saturated L-glutamine (left boxes).
Figure 14:
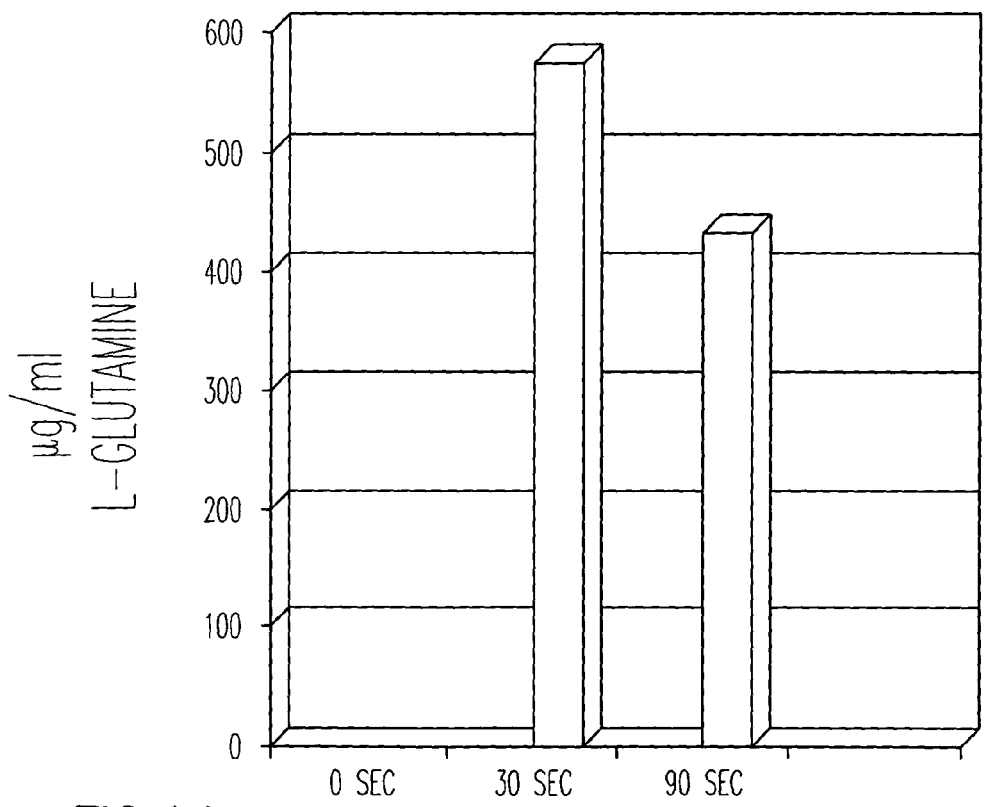
FIG. 14 depicts the effect of Aesgen-14 on L-glutamine uptake into human umbilical and endothelial cells.

In FIG. 13 the effect of Aesgen-14 vehicle on L-glutamine uptake into human fibroblasts (right boxes) vs. uptake of saturated L-glutamine (left boxes) is shown. FIG. 14 depicts the effect of vehicle on L-glutamine absorption into human endothelial cells. On the chart, the effect of saturated L-glutamine alone was not visible.

It should be noted that 5 minutes represents a very brief time frame for traditional Caco-2 permeability studies. It is unlikely that steady-state is achieved after 5 minutes, reducing the probability of observing any possible vehicle effect.

Summary

L-glutamine, L-asparagine, glycylsarcosine, and acyclovir represent two amino acids, a peptide, and an anti-viral agent, each with poor passive membrane penetration properties under normal physiological conditions. Hence, enhancement of their cellular uptake and membrane permeability is advantageous, from a drug delivery perspective. For saturated solutions of L-glutamine, L-asparagine, glycylsarcosine, and acyclovir, AES-14 vehicle enhanced their cellular drug uptake about four-fold. This enhancement of drug uptake into cells occurred immediately (i.e., <<1 min), and was sustained over the time period studies (5 min.). To perhaps a lesser extent, vehicle enhanced half-saturated L-glutamine. Vehicle had no effect to mannitol uptake. Regarding permeability over a very brief 5 minute period, vehicle had no effect for any compound.

TABLE 3

Caco-2 Permeability of Mannitol

| Study | Mannitol Permeability without Vehicle (cm/sec) | Mannitol Permeability with Vehicle (cm/sec.) |
|---|---|---|
| L-glutamine | $3.80 \times 10^{-9}$ | $9.16 \times 10^{-7}$ |
| Glycylsarcosine | Below LOQ | $1.48 \times 10^{-6}$ |
| L-asparigine | $3.80 \times 10^{-6}$ | $9.48 \times 10^{-7}$ |
| Acyclovir | $1.14 \times 10^{-6}$ | $1.46 \times 10^{-6}$ |
| L-glutamine (half-strength) | $1.49 \times 10^{-6}$ | Below LOQ |

EXAMPLE 3

Oral AES-14 Restores Gut Glutathione Production Disrupted by DMBA

Introduction: The mechanism by which oral glutamine (GLN) prevents DMBA-induced breast cancer is unknown. While GLN triples the negative extraction of gut glutathione (GSH) in rats, 7,12-dimethylbenz[a]anthracene (DMBA) significantly disrupts it. Actual gut GSH flux has not been reported. We hypothesized that the gut is a producer of GSH, DMBA blocks gut GSH production, and supplemental oral GLN antagonizes this effect.

Methods: 80 Sprague-Dawley rats were randomized to 4 groups (n=20/group): DMBA+GLN, DMBA+FA, OIL+GLN, OIL+FA. Rats (age 50 days) were gavaged with a 1-time dose of 20 mg DMBA or oil. Rats were gavaged with AES-14 (1 gm GLN/kg/day) or an isonitrogenous amount of Freamine (FA) from 1 week before till sacrifice at 1 week after DMBA (greatest effect on gut GSH extraction). Arterial and portal blood was taken for GLN and GSH levels, and blood flow measured using 14-C-PAH. Gut GLN and GSH fluxes (uptake or production) were calculated.

Figure 15A:
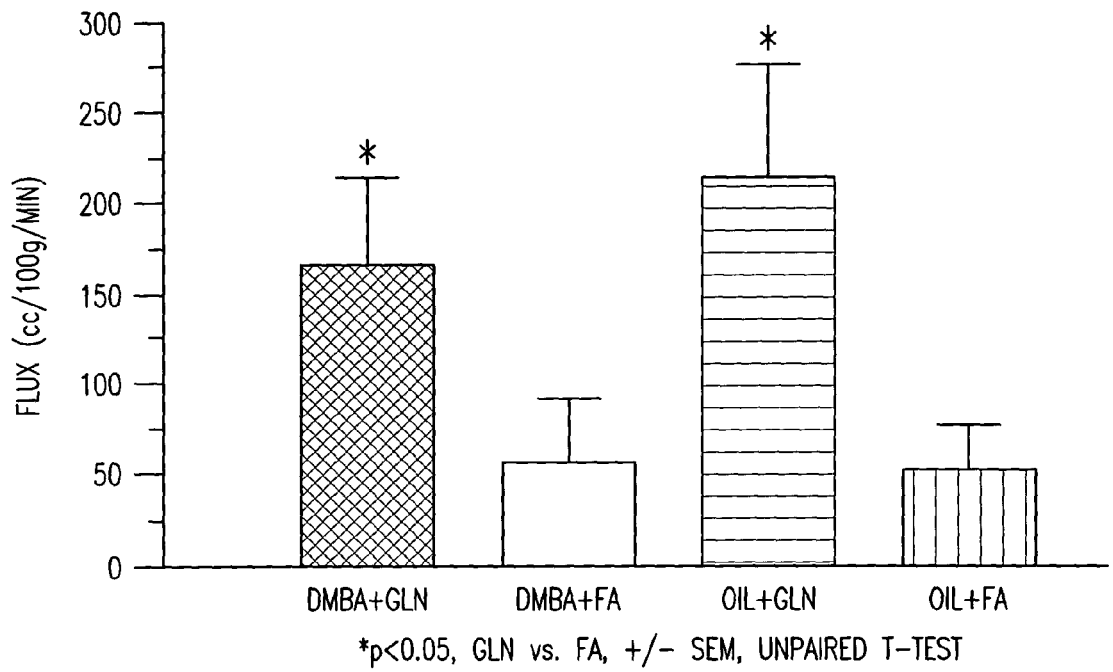
FIG. 15 shows the gut glutamine flux (panel A) and gut glutathione flux (panel B) of rats treated with DMBA+GLN (AES-14), DMBA+freeamine, oil+GLN (AES-14), and oil+freeamine.
Figure 15B:
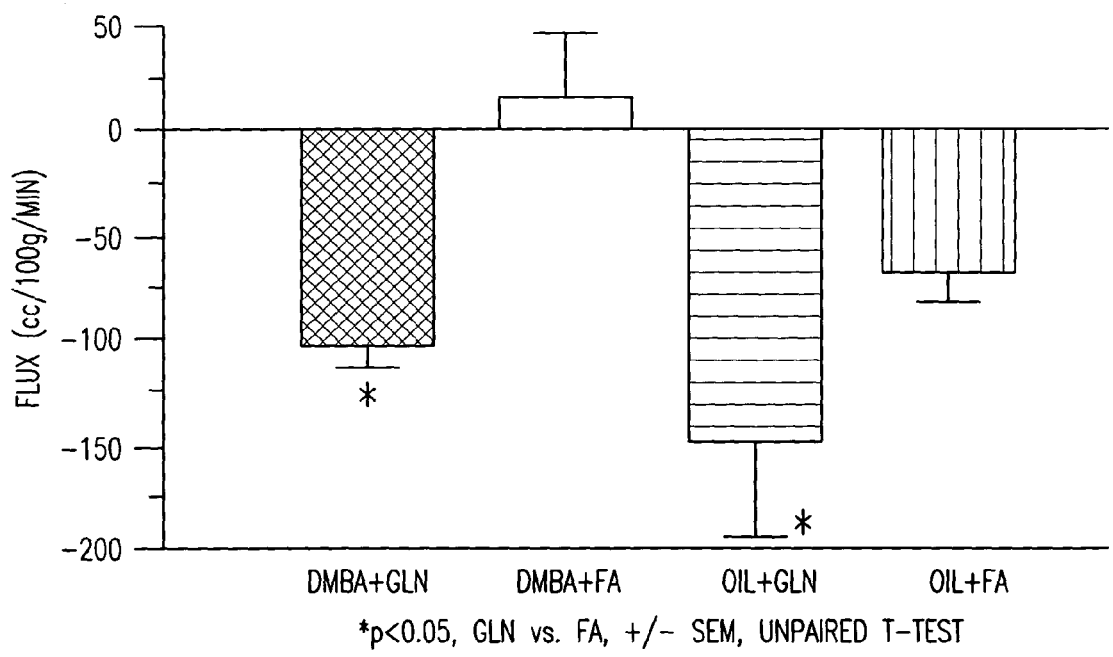

Results: DMBA abrogated the normal GSH production (negative flux) in OIL+FA while not affecting GLN metabolism (FIG. 15). GLN maintained GSH production in DMBA+GLN (FIG. 15).

Conclusions: Oral administration of AES-14 restores to normal GSH production in DMBA-treated animals suggesting one of the mechanism(s) by which GLN prevents breast cancer in this model. Unchanged uptake of GLN in the DMBA-treated animals may indicate a block in GSH transport rather than actual intracellular production.

EXAMPLE 4

Oral AES-14 Protects Breast Tissue Against Radiation Injury

The cosmetic result after breast conservation therapy (BCT) is limited, in part, by radiation injury to the skin and surrounding tissue. In preclinical studies, glutamine (GLN) has been shown to significantly reduce both acute and chronic radiation injury to the small bowel possibly through upregulation of glutathione (GSH) metabolism. Oral administration of AES-14 to provide GLN doubles normal intracellular breast GSH without increasing GSH in breast tumor tissue. We therefore hypothesized that GLN may safely prevent radiation injury to normal breast tissue in BCT patients.

This theory was tested in two parts. First, biopsies from human breast tumors before and after 3 days of oral AES-14 indicated no significant change in intracellular tumor GSH. A Phase III pilot study in which 17 patients were randomized to oral AES-14 (30 gm GLN/day, approximately 0.5 gm GLN/kg/day) or placebo from one week prior until one week after radiation therapy (5,000 cGy) was performed. Patients were followed weekly for 7 weeks and every 3 months for 2 years for acute and chronic radiation injury using the RTOG scales, skin biopsy at 0 and 7 weeks, GLN and GSH levels, US, mammogram density, lymphedema, quality of life and performance status.

The RTOG acute radiation morbidity scoring criteria for skin ranges from 0 (no change) to 4 (necrosis). A score of 2 (moist desquamation) was considered failure of treatment. Patients receiving oral AES-14 scored an average of 0.9±0.2, SEM compared to 1.4±0.2 in the placebo group. All patients in the placebo group reached a score of 2 or greater during the first 7 weeks. Two of 8 placebo patients required radiation therapy delay. Another patient scored 3 of 4 but did not delay radiation. Only 4 of 9 patients in the AES-14 group scored a high of 2, none a 3 (p=0.03 AES-14 vs. placebo, Fisher Exact). At 12 months, 4 of 8 patients in the placebo group complained of pain for which 3 required narcotics, 6 of 8 had significant edema and 4 of 8 marked increased density and firmness of the radiated breast. In the AES-14 group 2 of nine complained of mild pain not requiring narcotics, none had edema and one patient had minimal increased density of the breast (p=0.01, AES-14 vs. placebo, Fisher Exact). At 2 year follow-up, 2 placebo had local recurrence and none in the GLN group. Cosmetic scores averaged excellent (9.2±0.6) in the AES-14 group versus fair to good (7.3±1.0) in the placebo group.

The results of this pilot study suggest that oral GLN supplementation is a safe and effective way to reduce both acute and chronic radiation morbidity to the breast and may improve cosmesis.

EXAMPLE 5

Effect of Glutamine (AES-14) Supplementation on Serum IGF-1 Levels

Higher insulin-like growth factor-1 (IGF-1) levels are correlated with higher rates of cellular proliferation in the breast in vitro and in vivo (Ma, J. et al., JNCI 91:620, 1999; Hinkinson, S. E., et al., Lancet 351:1393, 1998). We hypothesized that the inhibition of tumor growth seen with oral glutamine may be secondary to lowering of serum IFG-1 levels. This is based on the knowledge that one mechanism of elimination of IGF-1 is through IGF-1 complexing with GSH. Increased levels of GSH to the liver would accelerate this elimination.

Methods:

One-hundred-ninety-two female Sprague-Dawley rats age 50 days were randomized to gavage with 1 gm/kg/day Gln in a 3% aqueous solution, isonitrogenous freeamine (a mixture of essential and non-essential amino acids, FA), or water, pair-fed with a defined diet of TD96163 chow, and gavaged with 100 mg/kg DMBA in sesame oil vs. control oil gavage at time 0. The 100 mg/kg dose of DMBA and the same timing was used in the remaining experiments to promote 100% tumorigenesis in the control groups. Rats from each group (n=48) were sacrificed at weeks 1, 2, 4, and 11. Arterial Gln, serum IGF-1 levels, and tumor growth were measured over time. Serum IGF-1 levels were measured using DSL-2900 Rat Radioimmunoassay Kit (Diagnostic Systems Laboratories, Inc., Texas) following the manufacturer's instructions.

Figure 16:
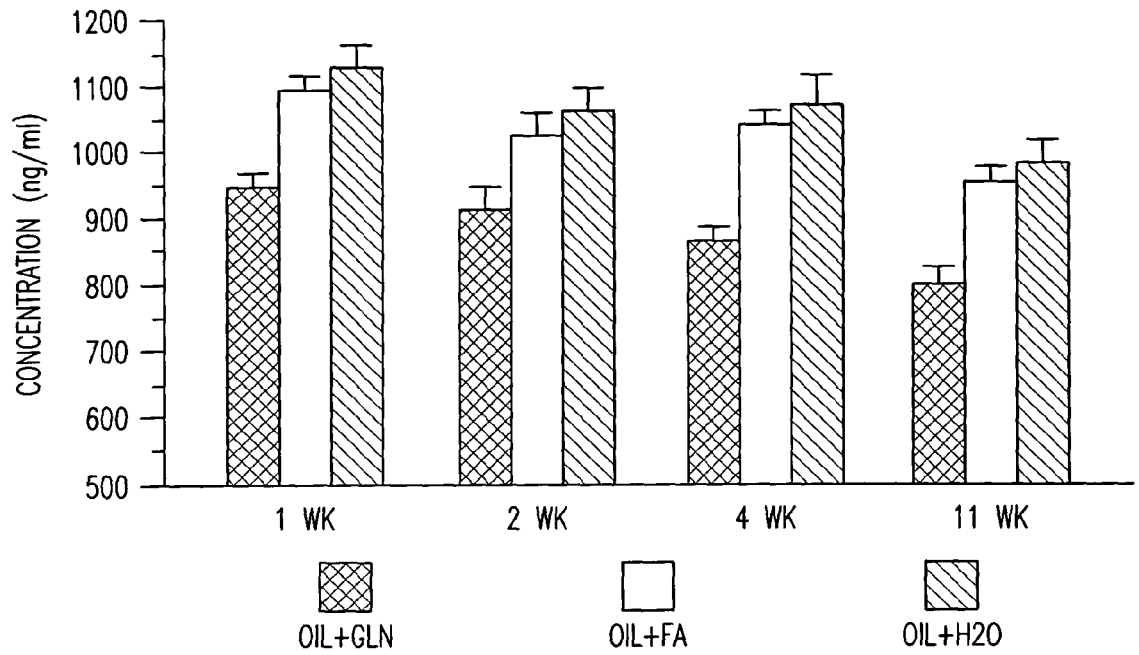
FIG. 16 shows the serum IGF-1 concentration in rats 1-11 weeks after gavage with sesame oil, treated following the oil gavage with oral AES-14 (GLN), isonitrogenous freeamine (FA), or water.
Figure 17:
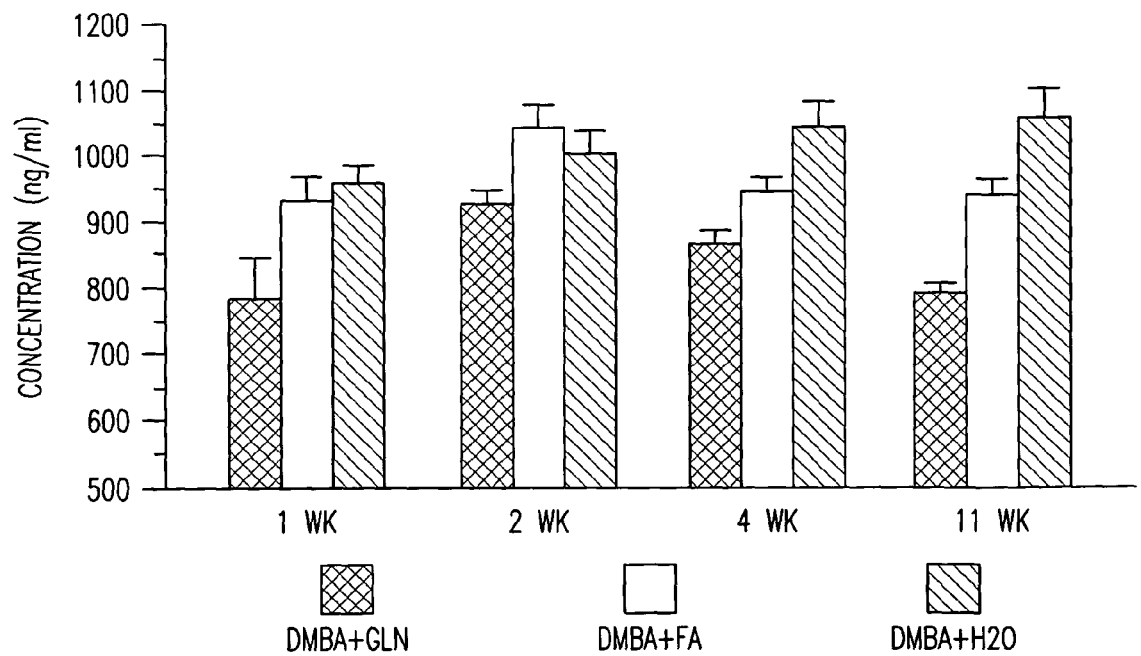
FIG. 17 shows the serum IGF-1 concentration in rats 1-11 weeks after gavage with DMBA in sesame oil, treated following the DMBA gavage with oral AES-14 (GLN), isonitrogenous freeamine (FA), or water.

Results:

Oral Gln as AES-14 significantly raised arterial Gln and GSH levels (~10%, data not shown) while lowering IGF-1 serum levels (~10-30%) (FIGS. 16 and 17). The lower IGF-1 levels were sustained over time in the presence or absence of DMBA. Supplemental oral Gln again significantly reduced the carcinogenesis of DMBA (100 mg/kg) in this rat model by 50% vs DMBA+FA and DMBA+$H_2O$, p<0.05. This compares with a 80 to 90% reduction using 80 mg/kg DMBA. The decrement in IGF-1 levels and decreased tumor growth in the Gln groups is similar to that seen with tamoxifen in this model (Jordan, V C, Reviews on Endoc. Rel. Cancer (October Suppl) 49-55, 1978).

EXAMPLE 6

Glutamine Supplementation Inhibits Tumor Development in 7,12-dimethylbenz[a]anthracene-induced Breast Cancer Through Enhancement of Apoptosis Introduction:

Despite the fact that GLN stimulates tumor cell growth in vitro, GLN supplementation significantly reduces tumor growth in vivo and enhances tumor kill with both radiation and chemotherapy (Klimberg et al., *JPEN*, 16: 1606-09 (1992), Farr et al., *JPEN*, 18: 471-76 (1994), Rouse et al., *Ann. Surg.*, 221: 420-26 (1995) and). It has been postulated that the inhibitory effect of GLN on tumor growth occurs by stimulation of glutathione (GSH) production (Feng et al., *Surg. Forum, XLVII:* 524-526 (1996)). GSH is the most abundant natural antioxidant and plays a central role in the body's defense against infection, free radicals and carcinogens (Larsson et al., In: The Metabolic and Molecular Basis of Inherited Disease (Eds. Scriver C F, Beaudet A L, Sly W S & Vallee D), McGraw Hill, New York 8th edition p. 2205-2216 (2001)). Recent studies however, have established that GSH levels are elevated in breast, colon, ovary and lung cancer tissues as compared with normal tissue. The elevated tumor GSH levels were associated with increased resistance to chemotherapy (Schnelldorfer et al., *Cancer,* 89: 1440-1447 (2000)). Therefore, selective depletion of tumor GSH could inhibit tumor growth and presents a new promising strategy in cancer prevention.

It is now generally accepted that inhibition of apoptosis plays a role in the carcinogenic process. Functional studies have determined that the elevated expression of anti-apoptotic Bcl-2 family members (Bcl-2, BCl-$X_L$, Mcl-1, A1) or diminished expression of proapoptotic Bcl-2 family members (Bad, Bax, Bid, Bik, Bak, Bcl-Xs) can inhibit the mitochondrial pathway (Kaufmann et al., *BioEssays,* 22:1007-1017 (2000) and Reed, *J. Cell Biol.,* 124: 1-6 (1994)). A positive correlation between the levels of GSH and Bcl-2 has been suggested (Voehringer, *Free Radic. Biol. Med.,* 27: 945-950 (1999) and Hall, *Eur J of Clin. Investig.,* 29:238-245 (1999)). It has been established for example, that Bcl-2 over-expression in the mitochondrial outer membrane inhibited the formation of reactive oxygen species in cells exposed to a number of apoptotic triggers (Hockenbery et al, *Cell,* 75: 241-251 (1993)). DMBA is a polycyclic aromatic hydrocarbon, metabolized in the organism through an oxidation to produce a diol-epoxide, which forms DNA adducts (Dipple et al., *Chem.-Biol. Interactions,* 20: 17-26 (1978) and Wei, *Med. Hypth.,* 39:267 (1992)). A single dose of DMBA to pubertal rats induces mammary carcinomas of ductal origin in 100% of the animals approximately 11 weeks after the DMBA application (Huggins et al., *Nature,* 189: 204-207 (1961)). We have previously shown that the DMBA-induced breast cancer in rats was associated with a significant inhibition of GSH production, causing GSH depletion (Cao et al., *J. Surg. Res.,* 100:135-140 (2001) GLN supplementation however, significantly diminished tumor growth and restored the decreased GSH levels in blood, breast tissue and gut mucosa (Klimberg et al., *Am. J. Surg.*, 172:418-424 (1996)). Based on those results we hypothesized that GLN stimulates apoptosis in the cancer cells through their GSH depletion. Therefore, here the effect of GLN on the levels of GSH and enzyme activity of caspase-3 in tumor cells, as well as the gene expression of caspase-3, Bcl-2, Bax and p21 in tumors using relative RT-PCR was studied.

Materials and Methods:

Experimental animals and treatment. Time-dated pubertal female Sprague-Dawley rats (Harlan Sprague-Dawley, Indianapolis, Ind.) less than 50 days old and weighing approximately 150 g were used. All studies were approved by the Animal Care and Use Committee at the Central Arkansas Veterans Healthcare System. The rats were maintained in standard cages in the animal care facility and were subjected to a 12-hour dark/light cycle. During the study period, the rats were pair-fed a predefined diet of chow (TD 96163) and were given water ad libitum. At age of 50 days old, the rats were randomized into 2 experimental groups and received a single dose of 100 mg/kg DMBA in sesame oil as a vehicle. All the animals were gavaged once a day with either a GLN (1 g/kg/day) suspension formulation (AES-14) (n=16) or water (n=16) for the duration of the entire experiment. The animals were examined weekly for tumor development and their body weights were recorded. The animals were sacrificed 11 weeks after the DMBA application, and tumor number, volume and weight were recorded. Tumor volumes were calculated using a standard formula: width$^2$×length×0.52 (Ingber et al., *Phys. Rev.*, 42: 7057 (1990)), and expressed as cubic centimeters. Ten tumors from each experimental group were used in the present Example. Tissue samples were collected, immediately frozen in dry ice and kept at −80° C. until used.

GSH measurement. GSH and GSSG contents in the tumors were measured via a standard enzymatic recycling method, as described by Tietze (*Ann. Biochem.*, 27:502-522 (1969)) and modified by Anderson (In: Glutathione, vol. 1, Dophin D (ed). New York: John Wiley & Sons, pg. 340-365). Briefly, 0.5 g tissue were homogenized with 2.5 ml 5% 5-sulfosalicylic acid, the protein content was measured and the samples were centrifuged at 5000×g, 5° C. for 15 minutes. Ten µl of the supernatant were added to 1 ml of reaction mix (0.2 mM reduced nicotineamide adenine dinucleotide phosphate, 0.6 mM 5,5-dithio-bis-2-nitrobenzoic acid and 1.33 units GSH reductase) and the absorbance was measured at 412 nm. To determine GSH disulfide (GSSG) content, 0.5 ml of the supernatant was mixed with 10 ul 2-vinyl pyridine and 60 ul triethanolamine in order to remove GSH via the method of Griffith (*Anal. Biochem.*, 106:207-212), then measured according to the above procedures. The data were normalized by milligram of protein and expressed as nM/mg protein.

Caspase-3 Assay. The enzymatic activity of the caspase-3 in the tumorous tissues was measured by a Caspase-3 Colorimetric Assay (R&D System, Minneapolis, Minn.). Briefly, 100 µg tissue extract were mixed with 50 µl reaction buffer and 5 µl caspase-3 substrate DEVD, conjugated to chromophore p-nitroanaline (pNA), and incubated at 37° C. for 1 hour. The intensity of the color reaction due to the release of p-nitroanilide was measured spectrophotometrically at 405 nm. Blank reading was subtracted from each sample reading before calculation. Data are expressed as absorbance (OD) at 405 nm.

RNA extraction and detection of gene products by relative RT-PCR. Total RNA was isolated by RNeasy Mini Kit (Qiagen, Chatsworth, Calif.). RNA (1 µg) was reverse transcribed using Ready-To-Go You-Prime First-Strand Beads (Amersham Pharmacia Biotech Inc, Piscataway, N.J.) and oligo (dT) (Promega, Madison, Wis.). First-strand cDNA (3 µl) was used as a template for the subsequent PCR-amplification with the following primers: caspase-3, forward, 5'CGATGCAGCTAACCTCAGAGA (SEQ ID NO:1), reverse, 5'CCTTCCGGTTAACACGAGTGA (SEQ ID NO:2); p21, forward: 5' GATCCTGGTGATGTCCGACCT (SEQ ID NO:3), reverse: 5' GGAACTTTGACTTCGC-CACTGA (SEQ ID NO:4). Bax- and Bcl-2 were examined using Rat Bax Dual-PCR Kit and Rat Bcl-2 Dual-PCR Kit (Maxim Biotech, Inc, San Fransisco, Calif.). The PCR was performed in a total of 25 µl with Taq PCR Master mix purchased from Qiagen (Chatsworth, Calif.) and 0.20 pmol of each primer for the amplification of caspase-3 and p21 or as suggested by the manufacturer for Bax and Bcl-2. Thirty-five cycles of reaction at 94° C. (60 sec) and the appropriate annealing temperature (90 sec), followed by 10 min at 72° C. were carried out in Perkin-Elmer 2400 thermal cycler. The amount of each of the transcripts was quantified by concurrently amplifying the 18S ribosomal unit as an internal control (Ambion, Austin, Tex.). Amplified cDNA was subjected to electrophoresis in 1.5% agarose gels containing 100 ng/ml ethidium bromide. At the completion of electrophoresis, gels were viewed and photographed under UV light. The amount of each transcript was calculated relative to the levels of 18S rRNA amplified from the same sample in the same tube.

Densitometry. The area and density of the bands resulted from RT-PCR were measured using Scion Image Program for IBM (Scion Corporation). The ratio of the signals of each target gene and 18S rRNA was calculated individually. The results were expressed as relative arbitrary units and were analyzed statistically.

Statistical Analysis. Comparisons between the groups were performed by a one-way analysis of ANOVA using statistical software StatView for Windows, version 4.5. All data was expressed as mean±Standard Error (SE). Results with P<0.05 were considered statistically significant.

Results:

Carcinogenicity of DMBA. There was no significant difference in the mean body weight of the animals from both groups at the beginning of the study or at the sacrifice. All the rats gained weight during the study period of 11 weeks. Fifty percent of the rats in the GLN-supplemented group did not have tumors at the end of the study. Most of the animals in this group had a single tumor, two rats had 3 tumors each. In the group that received water instead of GLN, 100% of the rats developed breast tumors and 6 of the animals had 3 and 4 tumors each. The total number of tumors in the experimental group fed with GLN was 12, versus 26 in the group fed with water. The weight of the tumors in the GLN treated group varied between 0.6 and 6 g, with an average tumor weight of 3.8 g, versus 0.07 to 19.7 g, with an average weight of 3.9 g in the water-treated group.

Figure 18A:
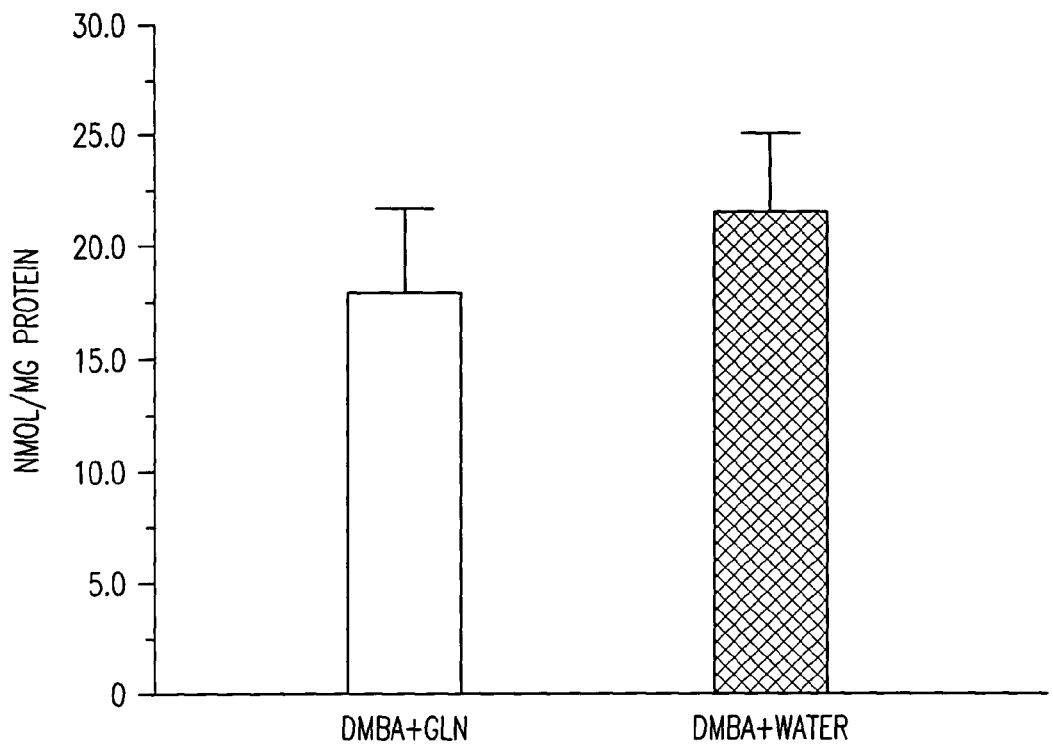
FIG. 18 shows the effect of GLN (AES-14) supplementation on the tumor levels of GSH (panel A) and GSSG (panel B) in experimental DMBA-induced breast cancer. Measurements were performed in triplicate. The results are expressed as nmol/mg protein with standard error bars shown.
Figure 18B:
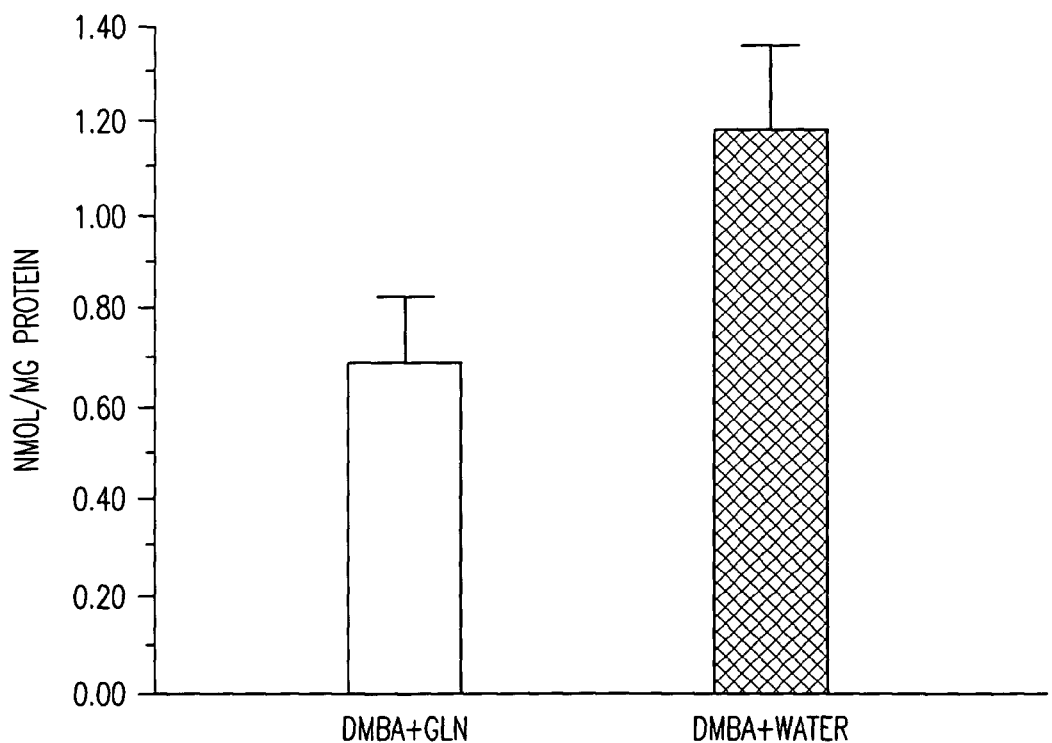

Supplemental GLN decreases the levels of tumor GSH. The decrease in the levels of the reduced glutathione was 22% (mean values±SE, 18.00±3.713 vs. 22.980±3.535), P<0.05 (P=0.4) (FIG. 18 panel A). More than a 40% decrease in the levels of oxidized glutathione in the tumors was established as a result of GLN supplementation (mean values of GSSG concentration in ng/µg protein±SE, 1.188±0.171 in the GLN-treated group versus 0.703±0.131 in the tumors from the group received water, P<0.05) (FIG. 18 panel B).

Figure 19:
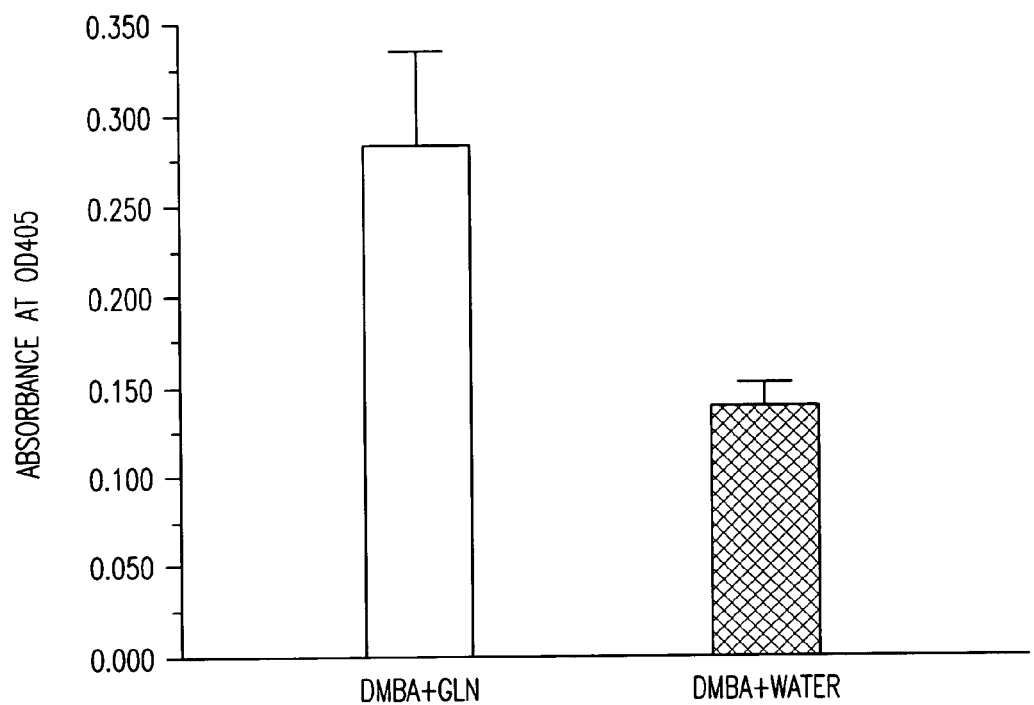
FIG. 19 shows the effect of GLN (AES-14) supplementation on caspase-3 enzymatic activity of DMBA-induced mammary gland tumors. The results are expressed as Absorbance at 405 nm with standard error bars shown. Measurements were performed in triplicate.

Effect of GLN supplementation on caspase-3 enzyme activity. The caspase-3 enzyme activity was found to be significantly increased in the tumorous tissue from animals treated with GLN (mean values±SE, 0.283±0.183 vs. 0.140±0.035 in optical density units at 405 nm, P<0.05) (FIG. 19).

Figure 20:
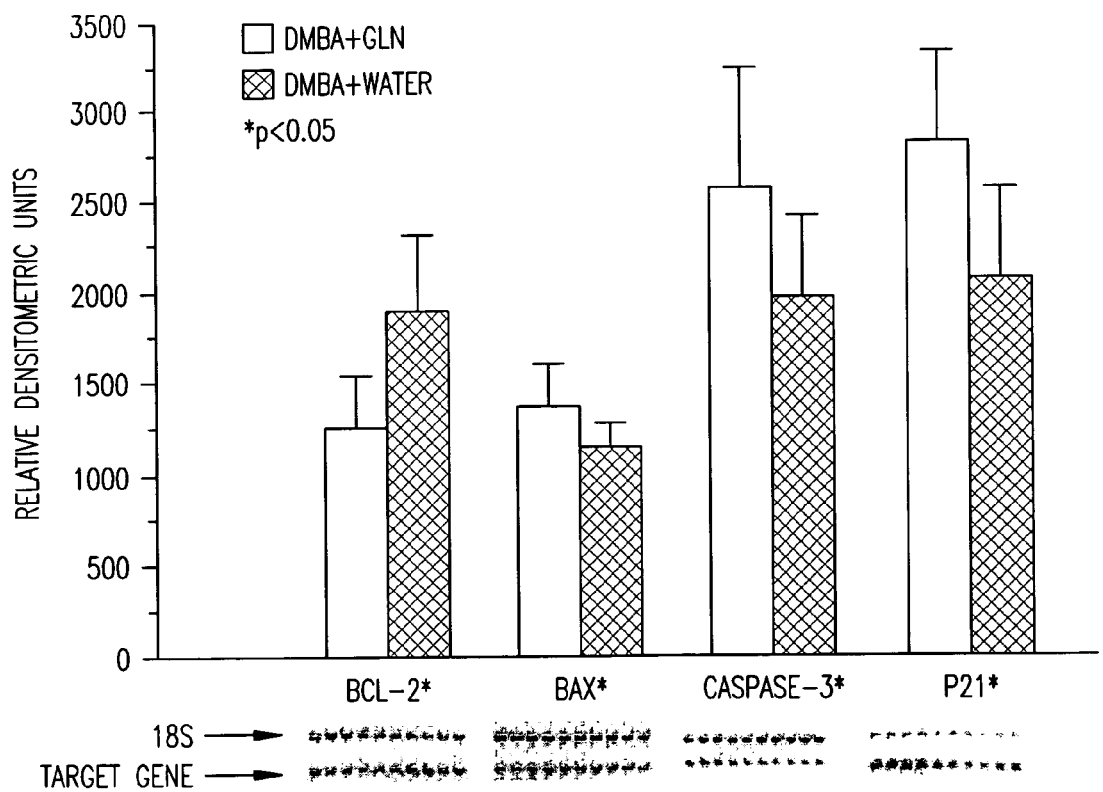
FIG. 20 shows the effect of GLN (AES-14) supplementation on mRNA expression of Bcl-2, Bax, caspase-3 and p21 in mammary tumors of rats treated with DMBA as established by relative RT-PCR. The results are expressed as arbitrary units with standard error bars shown. A representative (n=5) inverted agarose gel picture is presented under each column.

GLN down-regulated Bcl-2 and up-regulated Bax, caspase-3 and p21. The results from the gene expression analysis obtained by means of relative RT-PCR and quantitative densitometric analysis are presented on FIG. 20. GLN supplementation resulted in 34% inhibition of Bcl-2 in the tumors collected from animals that received GLN in comparison with the animals that were gavaged with water (mean values±SE, 1265±88 vs 1893±130, in arbitrary units, P<0.05). At the same time GLN enriched diet resulted in 27% increase in the expression of Bax (mean values±SE, 1371±79 vs 1150±41, in arbitrary units, P<0.05); 23% in the expression of caspase-3 (mean values±SE, 2579±213 vs 1989±141, in arbitrary units, P<0.05); and 24% in the expression of p21 (mean values±SE, 2851±177 vs 2167±161, in arbitrary units, P<0.05).

Discussion

The main focus of this Example was on the effect of GLN on tumor cell levels of GSH and activation of apoptosis. The results have established that GLN supplementation resulted in a 20% decrease of GSH and 41% decrease in GSSG. Most importantly, the decrease in tumor GSH correlated with almost a 50% increase in the enzyme activity of caspase-3. The increased caspase-3 activity was associated with up-regulation of caspase-3 and Bax gene expression as shown by relative RT-PCR analysis. GLN down-regulated the main anti-apoptotic protein Bcl-2 by 34% in the cancer cells. In addition, up-regulation of p21, an inhibitor of cyclin-dependent kinases, known to control cell proliferation, was demonstrated.

The importance of GSH depletion in promoting apoptosis has been demonstrated in several in vitro models (Bojes et al., *Biochem J.*, 325:315-319 (1997), Ho, et al., *Mol. Carcinog.*, 19: 101-113 (1997), and Roth et al., *Nutrition*, 18: 217-221 (2002)). Changes in the GSH levels have been found to affect apoptosis by regulating the expression of the Bcl-2 family of proteins (Bojes et al., *Biochem J.*, 325:315-319 (1997) and Voehringer, *Free Radic. Biol. Med.*, 27:945-950 (1999). It has also been suggested that GSH depletion is necessary and sufficient to induce cytochrome c release, which is the key event in the apoptotic mitochondrial signaling pathway. The mitochondrial alterations associated with apoptosis involve opening of the channels and release of cytochrome c into the cytosol, which is thought to cause translocation of some of the pro-apoptotic members of the Bcl-2 family from cytosol to the mitochondria and results in activation of apoptosis (Coppola et al., *Biochem. Soc. Trans.*, 28:56-61 (2000)). Obrador et al. (*Free Radic. Biol. Med.*, 3:642-650 (2001) reported that GLN-enriched diet activated the apoptotic cell death through a change in the glutathione redox status within tumor mitochondria. GLN is not traditionally thought of as a rate-limiting substrate for the synthesis of GSH, although GLN enhances GSH synthesis in normal cells and not in tumor cells. In the present Example, decreased levels of GSH and GSSG in the tumor tissue samples collected from rats fed with GLN (18 ng/mg protein after GLN vs. 23 ng/mg protein without GLN) were found. The effect of GLN on the levels of GSSG was more impressive—more than 40% decrease in the tumors. However, the strong reduction of GSSG which correlated with the increase caspase-3 activity in our experimental model is not consistent with the suggestion that increased levels of GSSG stimulate apoptosis (Celli et al., *Am. J. Physiol.*, 275:G749-G757 (1998)).

A number of studies have shown that GLN supplementation is beneficial in surgery, wound healing, trauma, AIDS, and prevention of complications associated with chemotherapy, radiation and bone marrow transplant (Labow et al., *World Journal of Surgery*, 24: 1503-1513. (2000) and Karinch et al., *Journal of Nutrition*, 131: 2535S-2577S (2001)). Several clinical trials have pointed out the importance of GLN in various clinical conditions (Piccirillo et al., *Hematologica*, 88:192-200 (2003)), but the molecular mechanisms that lie behind those beneficial effects of GLN are still not clear. In vitro studies established that GLN deprivation caused rapid elevation in the expression of growth arrest- and DNA damage-inducible genes (GADD45 and GADD153) in several human breast cell lines (Abcouwer et al., *J. Biol. Chem.*, 274: 28645-28651 (1999)). We have found that in DMBA-induced breast cancer GLN supplementation resulted in down-regulation of phosphatidylinositol-3 kinase (PI-3K)/Akt signaling pathway in the tumor surrounding normal tissue (Example 7).

In our experimental model of breast cancer, a single dose of DMBA to pubertal rats induces mammary carcinomas of ductal origin that mimics some aspects of human breast cancer and is a suitable model for studying the process of tumorigenesis. Oral GLN supplementation significantly inhibited tumor development and reversed the depressed GSH levels. The present results indicate that GLN supplementation significantly enhances the apoptosis of cancer cells possibly through GSH depletion. Increased gene expression of p21 suggests also the involvement cell cycle regulatory proteins. This result is consistent with established relation between GSH and the control of cell cycle checkpoints (Gansauge et la., *Cell Growth Differ.*, 9: 611-617 (1998)).

Altogether, the results from this Example suggest that GLN supplementation stimulates apoptosis in cancer cells in vivo possibly through reduction of GSH and modulation of gene expression of pro-apoptotic and anti-apoptotic members of the Bcl-2 family of proteins, and cell-cycle regulatory protein p21. These results provide a basis for further studies to clarify the exact molecular mechanisms of action of GLN in cancer in order to obtain information about its clinical application.

Conclusions:

The present Example established that GLN supplementation significantly reduces GSH levels in tumors. Since it is believed that there is a strong correlation between intracellular GSH levels and Bcl-2 mediated apoptosis, the effects of GLN-induced modulation of GSH on the involvement of apoptotic pathways in DMBA-induced breast cancer of female Sprague-Dawley rats were examined. Eleven weeks after the DMBA application 50% of the animals that received GLN during the entire experiment were free of tumors. A significant decrease in GSH levels and an increase in caspase-3 activity in the tumor cells from animals that received GLN. In addition, this Example established that GLN supplementation resulted in up-regulation of caspase-3, bax and p21 gene expression and down-regulation of Bcl-2 expression. Overall, these results suggest that GLN supplementation is a critical regulator of GSH synthesis in the organism under catabolic stress and inhibits DMBA-induced carcinogenesis in mammary glands through stimulation of apoptosis.

EXAMPLE 7

Oral Glutamine Supplementation Inhibits PI-3K/Akt Signaling in Experimental Breast Cancer Introduction 7,12-dimethylbenz[a]anthracene (DMBA) administration to pubertal rats causes breast tumors and inhibits glutathione (GSH) production. It is known that oral glutamine (GLN) supplementation significantly reduces tumor development. The present Example was designed to investigate the involvement of the IGF-1-activated phosphatidylinositol-3 kinase (PI-3K)/Akt apoptotic signaling pathway.

The hypothesis behind this Example was that the down-regulated IGF-1 would affect apoptotic cell signaling in the mammary gland tissue. The present Example establishes that dietary GLN supplementation significantly altered the protein expression of the members of PI-3K/Akt signaling cascade in the target tissue, promoting the process of apoptosis.

Materials and Methods

Experimental Animals and Treatment

A total of 40 time-dated pubertal female Sprague-Dawley rats (Harlan Sprague-Dawley, Indianapolis, Ind.) less than 50 days old and weighing approximately 150 g were used. All studies were approved by the Animal Care and Use Committee at the Central Arkansas Veterans Healthcare System. The rats were maintained in standard cages in the animal care facility and were subjected to a 12-hour dark/light cycle. During the study period, the rats were pair-fed a predefined diet of chow (TD 96163) and were given water ad libitum. At age of 50 days old, the rats were randomized into the following 4 groups (n=16): DMBA+GLN, DMBA+water, Oil+GLN and Oil+water and received a single dose of 100 mg/kg DMBA in sesame oil as a vehicle or sesame oil alone. All the animals were gavaged once a day with either a GLN (1 g/kg/day) suspension formulation (AES-14) or water for the duration of the entire experiment. The animals were examined weekly for tumor development and their body weights were recorded. The animals were sacrificed 11 weeks after the DMBA application; tumor number, volume and weight were recorded. Tumors and breasts were collected and immediately frozen in dry ice. Tissue samples were stored at −80° C. until used. Samples from tumors were fixed in 10% buffered formalin, embedded in paraffin, stained with Hematoxylin and Eosin stain, and examined microscopically for morphological changes.

Protein Extracts

Protein extracts were prepared from mammary gland tissue (frozen at −80° C.) by homogenization in the following lyses buffer: 10 mM Tris HCl, pH 7.6/5 mM EDTA/50 mM NaCl/30 mM $Na_4P_2O_7$/50 mM NaF/200 µM $Na_3VO_4$/1% Triton-X 100 and 1 tablet/50 ml buffer of Protease Inhibitor Cocktail Tablets (Roche Diagnostics GmbH, Mannheim, Germany). Homogenates were incubated at 4° C. overnight on an orbital shaker and centrifuged at 14,000 rpm at 4° C. for 30 min. The protein concentrations of the supernatants were measured using the Bio-Rad Protein Assay (Bio-Rad Laboratories, Hercules, Calif.).

SDS-PAGE and Immunoblotting

Forty micrograms of protein from each sample were fractionated on 10% polyacrylamide gels and transferred onto PVDF membrane using a Mini vertical Gel System (Thermo E C, Holbrook, N.Y.) (Sambrook et al., Molecular Cloning: A Laboratory Manual, $2^{nd}$ edition, Cold Spring Harbor, The Laboratory Press, 1987). Membranes were stained in 0.2% Ponso S after the transfer in order to control the equal loading of proteins. Following blocking with 5% non-fat milk in TBS-T buffer (100 mM Tris, pH 7.5; 150 mM NaCl; 0.1% Tween 20) buffer for 1 hr at room temperature, the membranes were incubated overnight at 4° C. (or 2 hr at room temperature) in primary antibody, diluted in 5% milk or 5% BSA and in HRP-labeled secondary antibody for 1 hour at RT. The equal protein loading was verified by re-probing the membranes with anti-1 actin antibody. Proteins were visualized using the ECL detection system (Amersham Biosci., Piscataway, N.J.). The following primary antibodies were used as recommended by the manufacturers: anti-IGF-1, anti-Bcl-2 and anti-β actin (Santa Cruz Biotech., Inc., Santa Cruz, Calif.), anti IGF-1R, anti-Akt, and anti-Bad (Cell Signaling Technology, Beverly, Mass.). The secondary antibodies (HRP-labeled anti-rabbit, anti-mouse and anti-goat) were purchased from Santa Cruz Biotech, Inc.

Densitometry

The area and density of the bands resulted from Western blotting were measured using Scion Image Program for IBM (Scion Corporation, Maryland, USA). The results, expressed in integrated density units/1000 were analyzed statistically.

Statistical Analysis

Data was expressed as mean±SE. Comparisons between the groups were performed by one-way analysis of ANOVA using statistical software StatView for Windows, version 4.5. Results with P<0.05 were considered statistically significant.

Results

There was no significant difference in the mean body weight among groups at the beginning of the study or at the sacrifice. All the rats gained weight during the study period of 11 weeks. Fifty percent of the rats in the GLN-supplemented group did not have tumors at the end of the study. Six of the animals in this group developed a single tumor and two had 3 tumors each. In the group that received water instead of glutamine, 100% of the rats developed breast tumors and 6 of the animals had 3 and 4 tumors each. The total number of tumors in the experimental group fed with GLN was 12, versus 26 in the group fed with water. The weight of the tumors in the GLN treated group varied between 0.6 and 6 g, with an average tumor weight of 3.8 g, versus 0.07 to 19.7 g, with an average weight of 3.9 g in the water-treated group.

The histological study of the tumors established that all of the tumors in both groups were malignant adenocarcinoma, as had been reported previously in the breast cancer model (Russo et al., *Lab. Invest.*, 57: 112-137 (1987) and Fukunishi, *Acta Path. Jap.*, 18: 51-72 (1968)).

The protein expression of IGF-1, its receptor IGF-1R, Akt, Bad and Bcl-2 by Western blot analysis in homogenates from non-tumorous and tumorous breast tissue extracts was determined. To establish more precisely the effect of GLN supplementation on the expression of the above proteins within the DMBA+GLN group, their levels in animals bearing tumors (DMBA+GLN, tumors) and animals which did not developed tumors (DMBA+GLN, no tumors) were compared.

Figure 21:
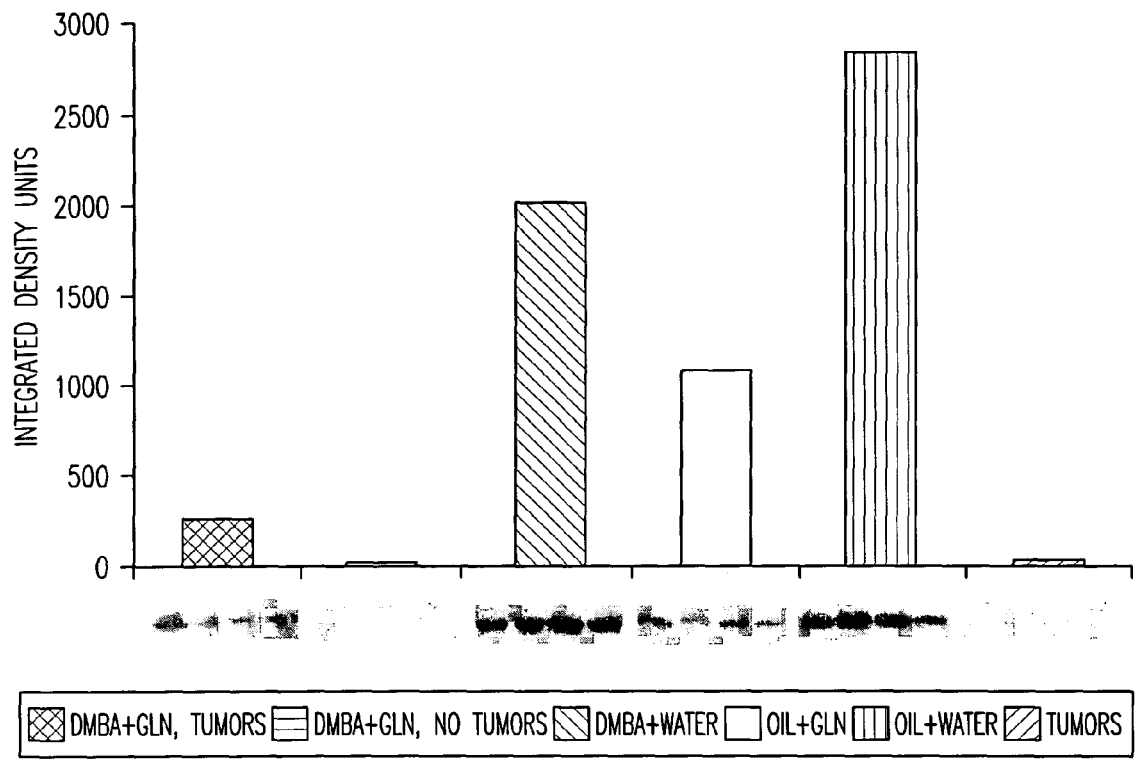
FIG. 21 shows inhibition of IGF-1 protein expression in non-tumorous breast tissue by GLN (AES-14) supplementation in the DMBA breast cancer model.

IGF-1. The results showed that GLN supplementation significantly down-regulated the expression of insulin-like growth factor-1 (IGF-1) in the DMBA-treated group in comparison with DMBA+water group (FIG. 21). More than 8 times lower levels of IGF-1 were found in the DMBA+GLN-with-tumors group in comparison with DMBA+water group (mean±SE, 238±82 vs. 1990±563 in integrated density units, P-0.008). No IGF-1 expression in the animals without tumors in the DMBA+GLN group was found. Reduction in the IGF-1 expression was also established in the control group, which received GLN, in comparison with the group that was fed with water (mean±SE, 1078±368 vs. 2836±1044 in integrated density units), although P for the interaction was not statistically significant P=0.1). No IGF-1 expression was detected in the tumorous tissue.

IGF-1R. GLN supplementation resulted in 2-fold reduction of IGF-1 receptor (IGF-1R) protein expression in breast tissue in the DMBA+GLN group in comparison with the expression in the group that received DMBA+water. There was no difference in the protein levels of IGF-1R in the breast tissue extracts from tumor-bearing rats treated with DMBA+

Figure 22:
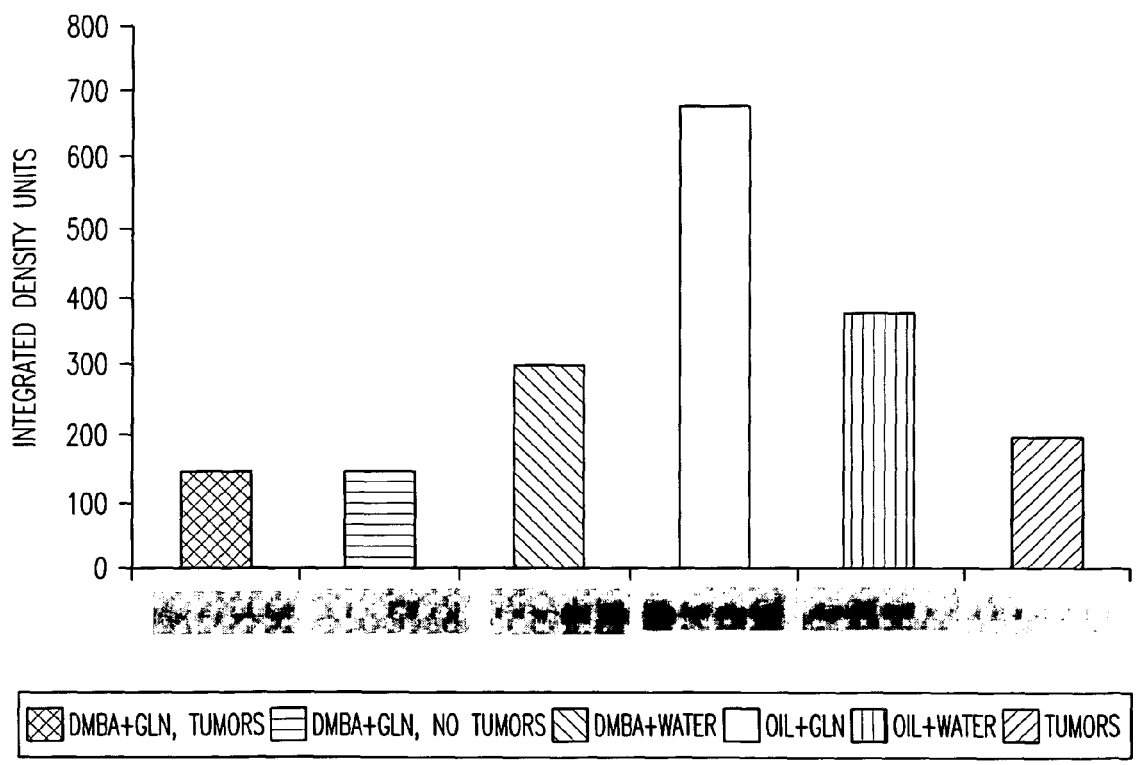
FIG. 22 shows the effect of dietary GLN (AES-14) on protein expression of IGF-1R in experimental DMBA-induced breast cancer.

GLN and rats without tumors from the same group (mean±SE, 141±12 vs. 142±32 in integrated density units) (FIG. 22). The differences in the expression in both groups treated with DMBA+GLN versus the DMBA+water group (mean±SE, 296±67) were statistically significant (P<0.05). GLN caused a statistically significant increase in the level of IGF-1R in the breast tissue of the control group versus the group gavaged with water (mean±SE, 674±150 vs. 368±34 in integrated density units, P=0.006). Tumorous tissues (mean±SE, 188±62) showed a statistically significant decrease in the levels of IGF-1R in comparison with the Oil+GLN and Oil+water groups (tumors vs. Oil+GLN, P=0.03; tumors vs. Oil+water, P=0.02). The differences in the IGF-1R levels in the tumorous and non-tumorous tissues from the DMBA+GLN and DMBA+water groups were not statistically significant.

Figure 23:
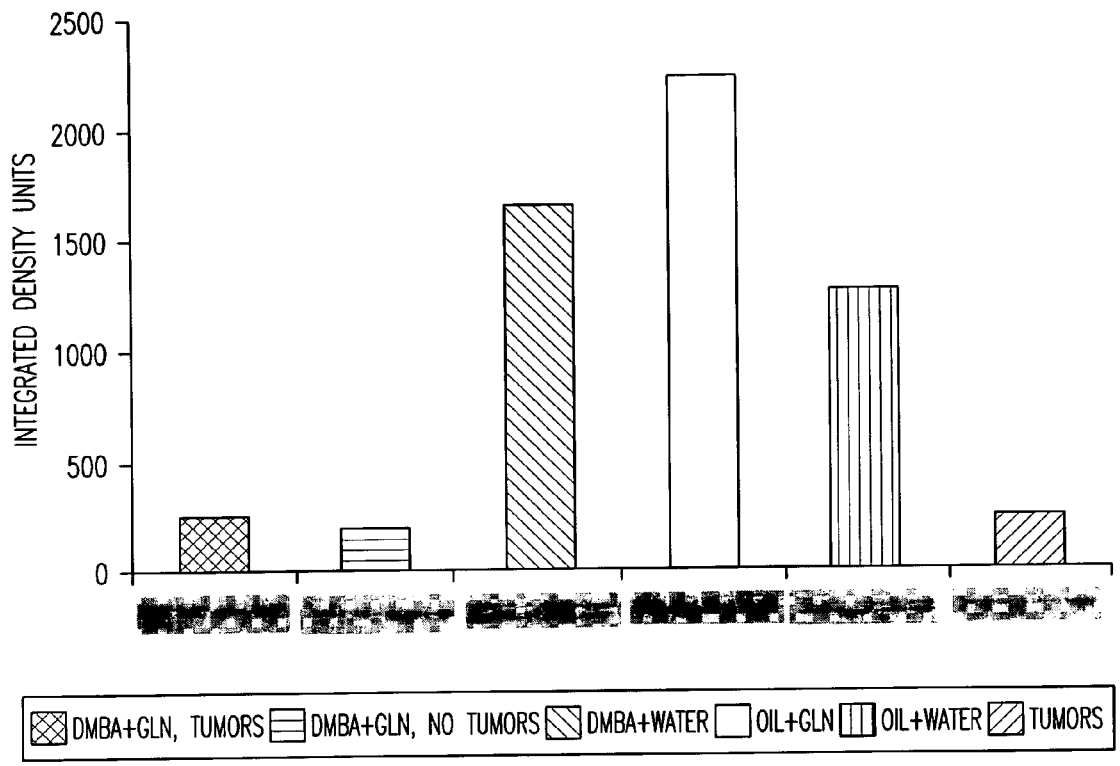
FIG. 23 shows the inhibitory effect of dietary GLN (AES-14) supplementation on Akt protein expression in experimental breast cancer of rats.

Akt. The protein expression of Akt was also significantly affected in the DMBA+GLN group (FIG. 23). GLN supplementation caused an almost 8-fold reduction of Akt expression (Akt protein levels) in the DMBA+GLN-without tumors group, compared with the expression in DMBA+water group (mean±SE, 1649±425 vs. 191±17, P<0.05) and more than 7-fold in DMBA+GLN-with tumors (mean±SE, 258±46). An approximately 2-fold increase in the Akt levels in GLN-supplemented control group versus the water group (mean±SE, 2243±288 vs 1253±291 in integrated density units, P=0.03) was found. Tumorous tissue samples showed a statistically significant reduction in Akt levels as compared with the Akt expression in the other groups (mean±SE, 229±46 in integrated density units, P<0.05).

Figure 24:
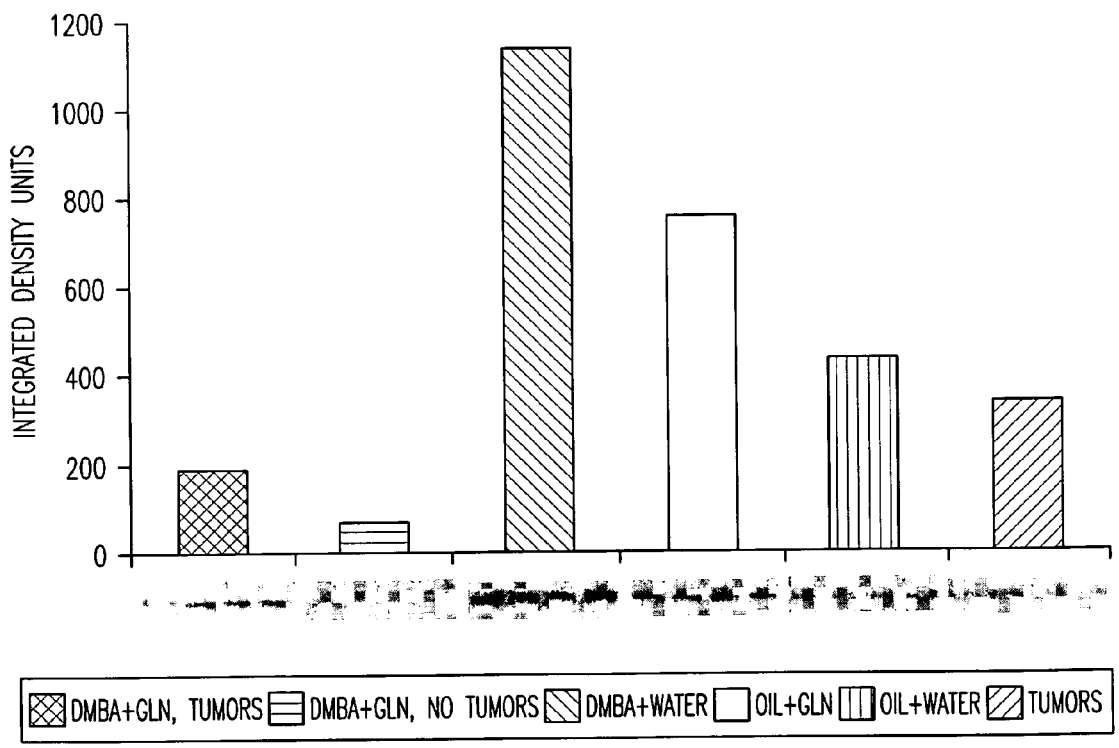
FIG. 24 shows the reduction of Bcl-2 protein expression in non-tumorous tissue samples from rats with experimental DMBA-induced breast cancer.

Bcl-2. Bcl-2 protein expression was approximately 20 times lower in the DMBA+GLN-without-tumors group than in the DMBA+water group (mean±SE, 63±7.3 vs 1253±214 in integrated density units, P=0.03) (FIG. 24). Eight-fold reduction of Bcl-2 was found in the DMBA+GLN-with-tumors group (mean±SE, 184.07±50) vs. DMBA+water. In the control groups, Bcl-2 levels were higher in the GLN-fed animals compared with the group that received water alone, but this was not statistically significant (mean±SE, 757±147 vs 429±102 in integrated density units, P=0.09). Tumors showed lower Bcl-2 levels than breast tissue of the DMBA+water group and the control groups, but higher than breast tissue of animals in the DMBA+GLN group (mean±SE, 331±86.8 in integrated density units).

Figure 25:
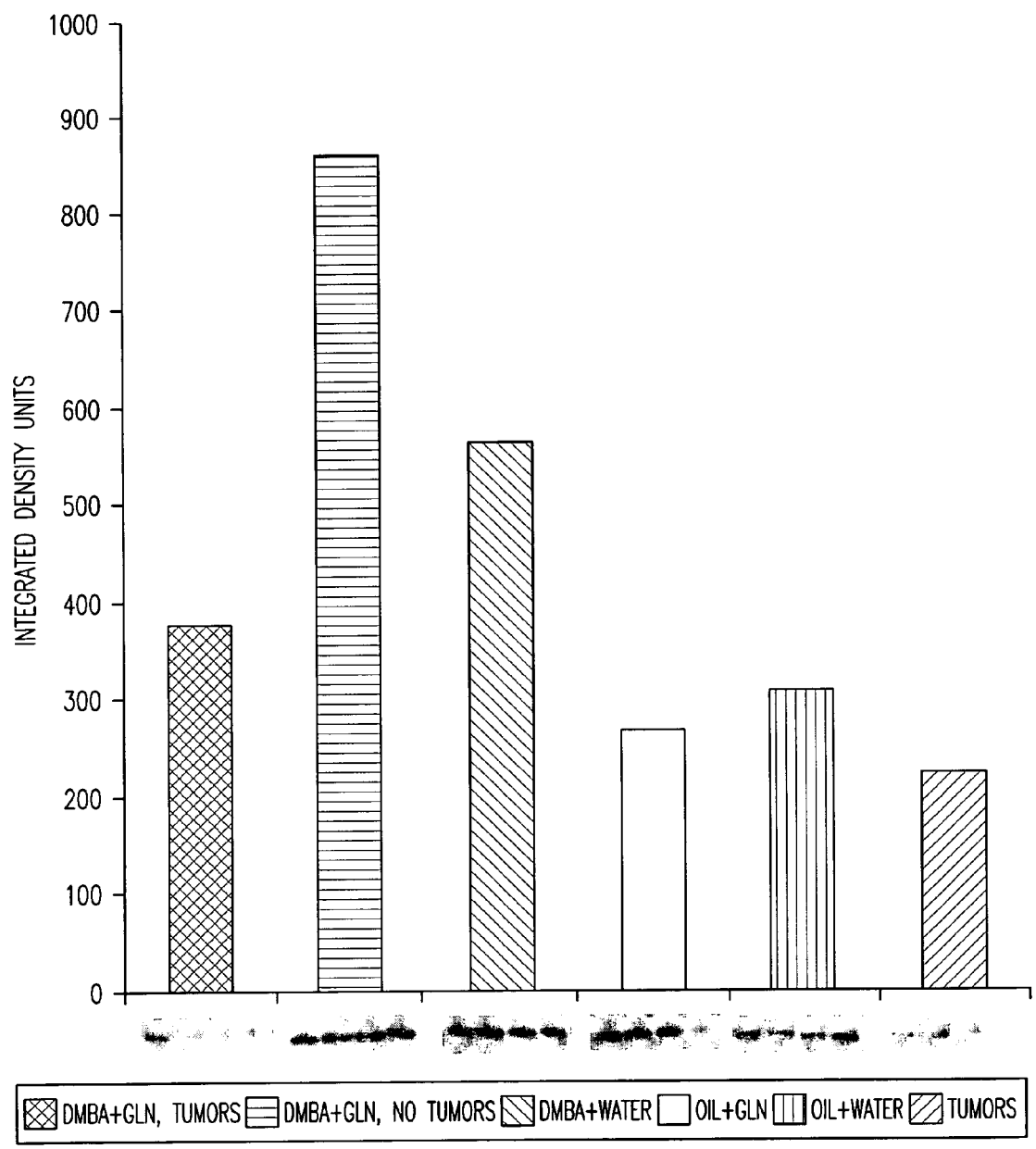
FIG. 25 shows the effect of GLN supplementation on Bad protein expression in the DMBA-induced breast cancer model.

Bad. GLN supplementation resulted in up-regulation of Bad protein expression in the DMBA+GLN-without-tumors group versus the DMBA+water group (mean±SE, 863±122 vs. 565±114, P=0.01) (FIG. 25). The levels of Bad in the DMBA+GLN-without-tumors animals were higher also in comparison with levels of DMBA+GLN-with-tumors animals (mean±SE, 376±116) (P<0.05). There were no statistically significant differences in Bad expression in the control groups (mean±SE, 266±57 for Oil+GLN, 308±55 for Oil+water). Tumorous tissue (mean±SE, 221±33 in integrated density units) did not show significant alterations in Bad expression compared to the control groups.

Discussion

In an experimental model of breast cancer, known as Huggins model, a single dose of DMBA to pubertal rats induces mammary carcinomas of ductal origin in 100% of the animals approximately 11 weeks after the DMBA application (Russo et al., Lab. Invest., 57: 112-137 (1987)). DMBA (a polylycyclic aromatic hydrocarbon) is metabolized through an oxidation to produce a diol-epoxide, which binds to DNA, creating point mutations (Fukunishi, Acta Path. Jap., 18: 51-72 (1968)). The results of Example 3 showed that oral GLN supplementation significantly reduced DMBA-induced tumor development and stimulated the depressed gut glutathione (GSH) synthesis that results from tumor growth. GLN is also associated with up-regulation of the decreased NK cell activity and decreased levels of IGF-1 and TGF-beta in the circulation (Farr et al., JPEN, 18(6): 471-476 (1994), Feng et al., Surg. Forum, XLVII: 524-526 (1996), and Cao et al., J. Surg. Res., 100: 135-140 (2001)). Although the mechanisms which underlie these effects of dietary GLN are not known, the involvement of apoptotic signaling system(s) might be suggested. The present results show that dietary GLN significantly down-regulated the protein expression of IGF-1, its receptor IGF-1R and the Akt apoptotic signaling pathway in the mammary gland tissue. The most impressive effect of GLN was the strong up-regulation of the pro-apoptotic protein Bad in the animals that did not develop tumors as a result of DMBA treatment compared to tumor bearing animals from the same group. The elevated tissue levels of Bad indicate stimulation of apoptosis as a counter-effect to the DMBA-induced tumorigenesis, resulting in the inhibition of tumor development.

It has been postulated that the inhibitory effect of GLN on tumor growth occurs by stimulation of glutathione (GSH) production (Farr et al., JPEN, 18(6): 471-476 (1994)). GSH is the most abundant antioxidant in the cell and plays a crucial role in the detoxification of carcinogenic xenobiotics thereby preventing DNA adduct formation (Karinch et al., Journal of Nutrition, 131: 2535S-2577S (2001)). In cells, glutathione exists normally in its reduced (thiol) form (GSH) and in minor amounts (<10%) as glutathione disulfide (GSSG) (Abcouwer et al., J. of Biol. Chem., 274: 28645-28651 (1999)). Its protective action is based on oxidation of the thiol group of its cysteine residue, resulting in the formation of GSSG; which in turn, is catalytically reduced back to GSH by glutathione reductase. GSH depletion is necessary and sufficient to induce cytochrome c release, which is the key event in the apoptotic mitochondrial signaling pathway. The mitochondrial alterations associated with apoptosis involve opening of the channels and release of cytochrome c into the cytosol, which seems to cause translocation of some of the pro-apoptotic members of the Bcl-2 family from cytosol to the mitochondria and results in activation of apoptosis (Larsson et al., 8 edn. New York: Mc Gray Hill, 2001).

The present study established that GLN supplementation modulated the apoptotic-related proteins Bcl-2 and Bax.

Conclusions:

GLN supplementation resulted in significant decrease in the levels of IGF-1, IGF-1R, Akt and Bcl-2 in non-tumorous samples. At the same time, the levels of pro-apoptotic protein Bad were significantly elevated. The samples collected from tumor tissues showed lower levels of IGF-1, Akt, Bcl-2, Bad and IGF-1R in comparison with non-tumorous. GLN supplementation inhibited the PI-3K/Akt pathway that is thought to be important in increasing cell survival during tumorigenesis. These results are in agreement with our hypothesis that GLN counteracts the effects of DMBA and blocks carcinogenesis in vivo.

EXAMPLE 8

Effect of DMBA on Glutathione Transport

Introduction: Oral intake of 7,12-dimethylbenz[a]anthracene (DMBA) causes mammary carcinomas in experimental rats and is associated with a depressed gut glutathione (GSH) production and a marked decrease in the portal glutathione levels. We therefore hypothesized that DMBA causes inhibition in the GSH transport across jejunal basolateral membrane and thus reduces GSH efflux. In order to prove this hypothesis, GSH transport through the jejunal basolateral membrane vesicle was examined.

Methods: The transport of GSH in the jejunal basolateral membrane vesicles (BLMV) was investigated in Sprague-Dawley rats treated with a single dose of 100 mg/kg DMBA (n=15) or sesame oil (n=15) as controls. The animals were pair-fed pre-defined chow and were given water ad libitum. All rats were sacrificed one week after the DMBA administration. Jejunal basolateral membrane vesicles (BLMV) were prepared using Percoll Colloidal PVP coated silica differential centrifugation technique. All steps were carried out at 2-4° C. Jejunal mucosal scraping was homogenized in isolation buffer containing 180 mM sucrose/2 mM Tris being adjusted to pH 7.40 by 2 mM Hepes using a Polytron homogenizer (Brinkman, Rexdale, ON), at setting 2 to 6 then 6 to 2, over 55 seconds. The homogenate was centrifuges for 10 minutes at 1000 g. The supernatant was filtered through four layers gauze and recollected. The supernatant containing basolateral membrane material then was centrifuged 15 minutes at 22,000 g. The loosely packed upper portion of pellet was washed out carefully, aspirated and suspended to 12 ml in isolation buffer. 1.4 ml Percoll was added and stirred lightly for 20 minutes. This suspension was centrifuged 35 minutes at 42,000 g. Two bands were formed. The top 2.4 ml of the gradient containing basolateral membrane was recollected and diluted with washing buffer, which is composed of 60 mM KCL/60 mM sucrose/2 mM Tris being adjusted to pH 7.40 with 2 mM Hepes. Again, this suspension was centrifuged for 90 minutes at 60,000 g. The membrane fraction was carefully washed out from the top of Percoll pellet with washing buffer. This final suspension was titrated to a protein concentration 12-15 ug/ul with washing buffer for further investigation. Protein concentration was determined by the Bio-Rad protein assay (Bio-Rad Laboratories, Hercules, Calif.).

The uptake of [$^3$H]Glutathione was measured by a rapid mixing/filtration technique. 40 ul of radioactive uptake buffer was placed at the bottom of a 12×75 mm Borosilicate Glass Culture Tube (Fisher scientific). To initiate the binding reaction, 20 ul of membrane vesicles was added and vibrated rapidly for 8 seconds controlled by a timer (Gralab Instruments, Centerville, Ohio). At the end of 8 seconds, 1 ml stop buffer containing 150 mM NaCl/10 mM Hepes/10 mM Tris was added. All of solution was aspirated out and discharged onto a filter in an uptake/vacuum apparatus. Another 9 ml cold stop buffer washed the filter membrane through. The filter membranes extracting the basolateral membrane vesicles was removed and placed in scintillation vials. Three ml Aquasol (Packard BioScience, Meriden, Conn.) was added to the vials and the vials were kept at room temperature for 16 hours until the filter membrane was dissolved. All vials were counted with liquid scintillation system LS 1801 (Beckman coulter, Fullerton, Calif.).

Results: The results showed that DMBA caused inhibition of GSH uptake in the jejunal basolateral membrane vesicles, which demonstrated that the Na$^+$ dependent amino acid transporter system, defined as System ASC/B$^0$ (Bode, BP (2001) *J. Nutrition* 131: 2539S-2542S) was inhibited by DMBA administration. The rate of total GSH uptake by BLMV in the DMBA group (FIG. 26) was decreased by 42% in comparison with the control group. The portal blood GSH concentration (FIG. 27) was decreased by 34% and the gut mucosa GSH (FIG. 28) was increased two-fold.

Conclusions: Both GSH transport and portal GSH concentration in rats gavaged with DMBA were significantly decreased (p<0.05, unpaired t-test). One of the mechanism(s) by which DMBA decreases gut GSH release and induces carcinogenesis might be through the significant depression of GSH efflux due to an inhibition of the GSH transport system. Decreased gut GSH efflux and portal GSH levels enhances the development of DNA adduct in liver that result in carcinogenesis. GLN has been shown to overcome the depression of GSH efflux probably through this transport mechanism.

EXAMPLE 9

Effect of Glutamine (AES-14) on the Enzyme Activity in the Gamma-Glutamyl Cycle

Oral glutamine (GLN) (AES-14) was found to diminish tumor development in the 7,12-Dimethybenz[a]anthracene (DMBA)-induced breast cancer model. This was associated with a significant increase of glutathione (GSH) levels in the normal host tissues and a decrease in GSH level in tumors. In the gamma-glutamyl cycle involving GSH synthesis, there are two key enzymes: γ-glutamyl transpeptidase (GT), which transports amino acids to provide substrates for GSH synthesis and γ-glutamylcysteine synthetase (GCS), which is the rate-limiting enzyme in GSH synthesis. We hypothesized that oral GLN would differentially affect these enzymes in order to restore host GSH and deplete tumor GSH.

Methods: Female Sprague-Dawley rats were randomized into six groups: DMBA+GLN, DMBA+FA, DMBA+H$_2$O, Oil+GLN, Oil+FA, Oil+H$_2$O. At age of 50 days, rats received a single dose of 100 mg/kg DMBA or sesame oil and were randomly gavaged with GLN (AES-14) (1 gm/kg/day) or isonitrogenous amount of Freamine (FA) or water (H$_2$O) by gavage starting 1 week before the dosing of DMBA until sacrifice. The jejunum mucosa and tumor tissues were collected and assayed for GT and GCS activity. GT activity was determined using the method of Wahlefeld and Bergmeyer (Wahlefeld A W, Bergmeyer H U: Routine method. In Bergmeyer H U, Bergmeyer J, Graβ1 M eds. Methods of enzymatic analysis, 3$^{rd}$ edition, vol III, Verlag Chemie, Weinheim, Deerfield beach, Fla. 1983, p. 352). Briefly, 0.1 g tissue was homogenized in 5 volumes of homogenizing buffer (100 mM Tris/HCl, 150 mM sodium chloride, 0.1% v/v tritonX-100, PH=8) using PowderGen 125 homogenizer. The homogenate was added to a mixture of enzyme substrates (2.9 mM L-γ-glutamyl-3-carboxy-4-nitroanilide; pH 7-7.5 and 100 mM Tris/glycylglycine, pH 8.25). The increase in the absorption was monitored continuously at 405 nm for 3 min. The protein concentration was determined by BioRad protein assay.

The GT activity was calculated using the following formula:

$$GT \text{ Activity (U/mg protein)} = \frac{\text{Rate} \times TV \times 1000}{\varepsilon \times SV \times LP \times PC}$$

Where:
Rate=Change in absorbance per minute at 405 nm (ΔABS/min)
TV=Total reaction mixture volume (ml)
SV=Sample volume (ml)
LP=Lightpath (10 mm in this case)
PC=Protein concentration (mg protein/l)
ε=Millimolar absorptivity of cana at 405 (0.951ΔABS/mmol/l/mm in this case)
1000=Converts units millimole to units micromole.
One unit of GT activity was defined as that amount of enzyme that would catalyze the formation of one micromole of 3-carboxy-4-nitroaniline (cana) per minute under the conditions of the assay procedure.

GCS activity was measured using the methods of Sekura and Meister (Sekura, R., et al. (1977) *J. Biol. Chem.* 252: 2599) and Taussky and Shorr (Taussky, H. H., et al. (1953) *J. Biol. Chem.* 202:675) The tissue (0.1 g) was homogenized in a homogenizing solution (150 mM potassium chloride, 5 mM 2-mercaptoethanol, and 1 mM magnesium chloride) at a ratio of 1:5 (w/v). Ten µl of the homogenate were added to 0.5 ml of a reaction mixture, containing 10 mM sodium L-glutamate, 10 mM L-α-aminobutyrate, 20 mM magnesium chloride, 5 mM sodium ATP, 2 mM sodium EDTA, 100 mM pH 8.2 Tris/HCl buffer, and 10 µg bovine serum albumin and incubated for 30 min at 37° C. in a shaking water bath. The reaction was terminated by adding 0.5 ml of 10% trichloroacetic acid. The mixture was centrifuged at 1500 RPM, 4° C. for 10 min and 100 µl of the supernatant were added to 0.5 ml 12.6% trichloroacetic acid, and a 0.4 ml Fe-reagent (10% ammonium molybdate, 5% ferrous sulfate in ION sulfuric acid) and the optical density was measured at 720 nm. A standard curve was used to determine the concentration of inorganic phosphate. The protein concentration of each sample was measured by BioRad protein assay. The enzyme γ-GCS activity was calculated as following formula:

$$GCS\ activity = \frac{ABS_{RXN} - ABS_{BL}}{Slope \times PC}$$

Where, $ABS_{RXN}$=the absorbance of sample after reaction at 720 nm $ABS_{BL}$=the absorbance of control at 720 nm Slope=the slope of the standard curve PC=the protein concentration of sample homogenate.

The enzyme GCS activity was expressed as microgram inorganic phosphate formed per milligram protein.

Figure 29:
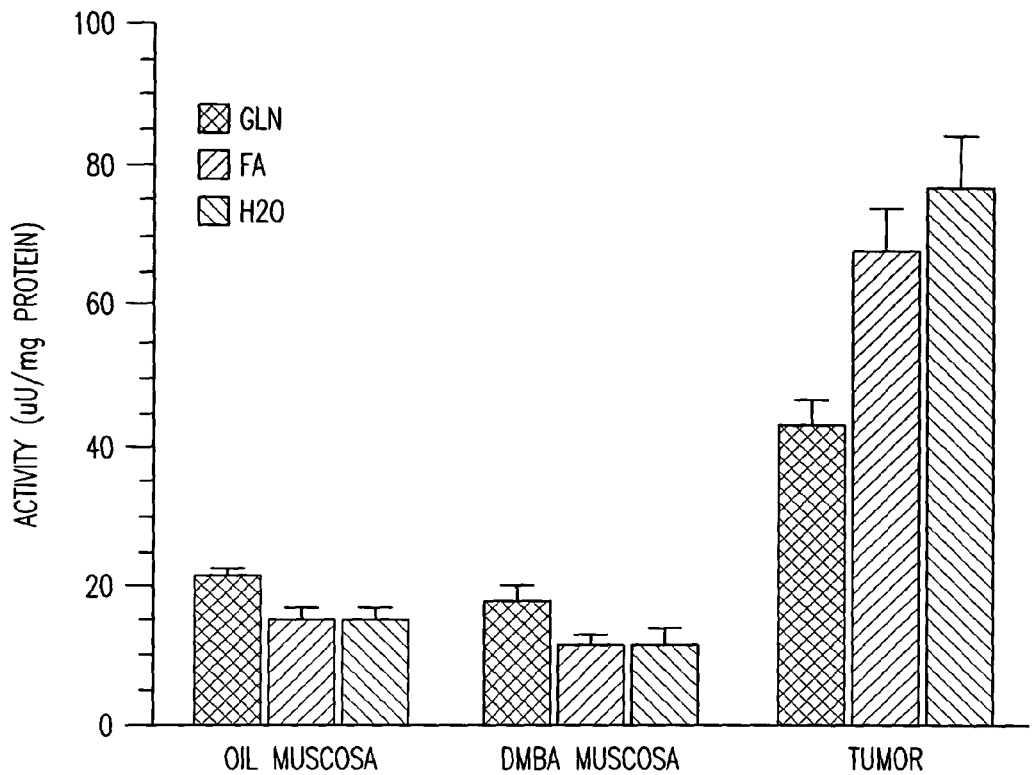
FIG. 29 shows the gamma-glutamyl transpeptidase (GT) activity of mucosal tissues of rats fed sesame oil and the mucosal and tumor tissues of rats gavaged with DMBA.
Figure 30:
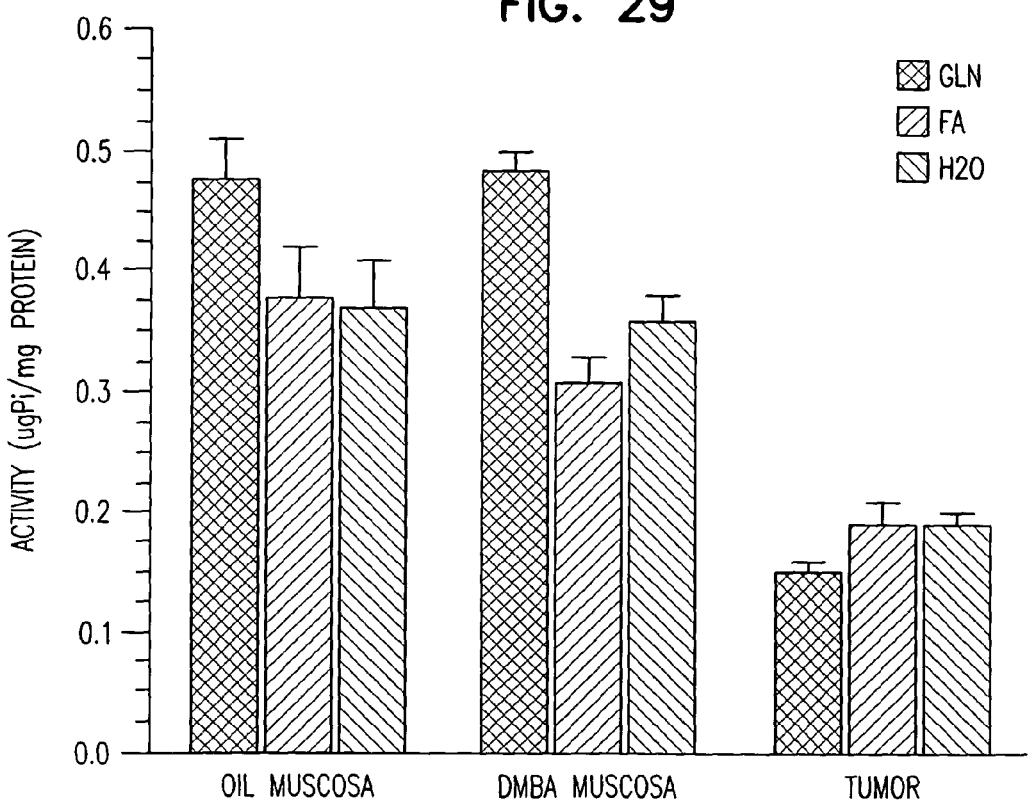
FIG. 30 shows the gamma-glutamylcysteine sythetase activity of mucosal tissues of rats fed sesame oil and the mucosal and tumor tissues of rats gavaged with DMBA.

Results: Oral GLN significantly increased host tissue GT and GCS activity but inhibited tumor tissue GT and GCS activity (FIGS. 29 and 30).

Conclusions: Oral GLN stimulates GSH synthesis in the host through up-regulation of the enzyme activity of GT and GCS. At the same time, GLN causes a decrease in the tumor GSH synthesis through reducing the enzyme activity of these key enzymes. The reduction of tumor GSH makes cancer cells more susceptible to radiation and chemotherapy while the increase in host GSH makes the patient less susceptible to the normal tissue damage. This differential effect results in a widened therapeutic window and possible increased host survival.

EXAMPLE 10

Effect of Glutamine Supplementation on Natural Killer Cell Cytotoxicity Over Time We hypothesized that glutamine may act to prevent DMBA-induced cancer by reversing the previously reported DMBA-induced depression of natural killer (NK) cell cytotoxicity.

Methods:

Rats were treated as in Example 5.

NK cell cytotoxicity was measured as follows: Aseptically removed spleens were minced using a sterile scalpel, and lymphocytes were teased from the splenic capsule with warm RPMI 1640 (Gibco BRL, Life Technologies Inc., Grand Island, N.Y.). The resulting cells were poured into 50 ml conical tubes, which were filled with ammonium chloride (0.83%) (Sigma Chemical Co., St. Louis, Mo.) to lyse the red cells. The cell solution was then centrifuged for 10 minutes at 1000 rpm. The supernatant was decanted, and the cell pellet was vortexed with RPMI (no GLN) and centrifuged again. Next, the cells were resuspended in approximately 10 ml of RPMI containing 10% fetal bovine serum (PBS) (Gibco BRL, Life Technologies Inc., Grand Island, N.Y.) supplemented with 1% GLN. This cell suspension was placed in Petri dishes and incubated in 6% $CO_2$ at 37° C. for 30 minutes. After incubation to assure adherence of the monocytes, the nonadherent lymphocytes were counted (1:1 with crystal violet stain). Approximately $7 \times 10^6$ total cells from each spleen were incubated for 3 days in RPMI containing 10% FBS and recombinant human IL-2 (500 U/ml). This cell suspension was used for determination of NK cell cytotoxicity by a four-hour 51-Chromium release assay with the NK cell-sensitive mouse tumor cell line, YAC-1. The NK cytotoxicity is expressed in lytic units (LU). LU is defined as the number of effector cells per $10^6$ mediating 20% target cell lysis. The calculation of the NK activity is expressed as the following equation:

$$Percent\ specific\ lysis\ (\%) = \frac{Experimental\ release - Spontaneous\ release}{Maximum\ release - Spontaneous\ release} \times 100$$

Figure 31:
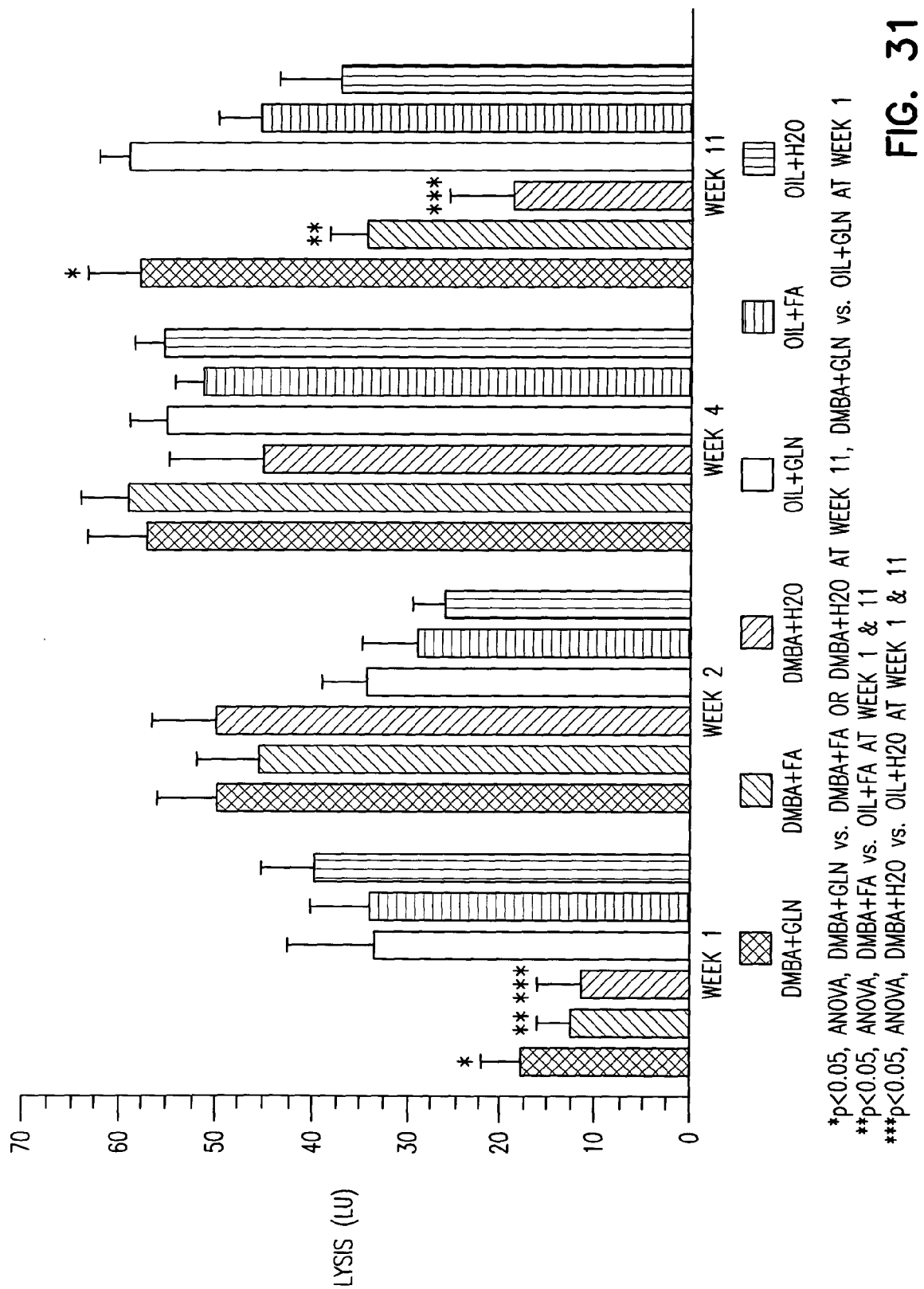
FIG. 31 shows the natural killer cell activity of NK cells sampled from rats 1-11 weeks after gavage with DMBA in sesame oil or sesame oil control (oil) and orally administered during the study period following the gavage AES-14 (GLN), freeamine (FA), or water.

Results:

NK cell activity was lower in the DMBA group only at week 1 and week 11 (FIG. 31). At week 2 there was a significant unexplained elevation of NK cell cytotoxicity in the DMBA group over that of non-DMBA controls. Oral Gln fully reversed the late but not the early depression of NK cell activity. However, oral Gln partially reversed the DMBA-induced depression of NK cell activity at 1 week as well.

The invention is described with reference to various specific and preferred embodiments and techniques. However, it should be understood that many variations and modifications may be made while remaining within its scope.

All referenced publications, patents and patent documents are hereby incorporated by reference, as though individually incorporated by reference.

What is claimed is:

1. A method of protecting normal tissue against damage from radiation therapy the method comprising:
   orally administering to a human subject afflicted with breast cancer and treated with radiation therapy an aqueous composition comprising a therapeutically effective amount of glutamine or a pharmaceutically acceptable salt thereof, and about 20-40 wt-% carbohydrate in an amount effective to increase the absorption of glutamine by the subject, wherein the composition protects the normal breast tissue or associated non-mucosal upper body tissue against damage from the radiation therapy.

2. The method of claim 1 wherein the composition prevents increased breast density or lessens the severity of increased breast density.

3. The method of claim 1 wherein the composition prevents edema or lessens the severity of edema.

4. The method of claim 3 wherein the edema is of breast tissue.

5. The method of claim 1 wherein the tissue is skin.

6. The method of claim 1 wherein the composition protects the appearance of the tissue.

7. The method of claim 1, wherein the amount of glutamine administered is at least 0.5 mg per day per kg body mass of the subject.

8. The method of claim 7 wherein the amount of glutamine administered is 0.2 g to 3.0 g per day per kg body mass of the subject.

9. The method of claim 1, wherein the amount of glutamine administered to the subject is less than 0.5 g per kg per day.

10. The method of claim 1, wherein the amount of glutamine administered to the subject is less than 0.1 g per kg per day.

11. The method of claim 1, wherein the carbohydrate comprises one or more monosaccharides or disaccharides.

12. The method of claim 1, wherein the carbohydrate comprises a sugar alcohol.

13. The method of claim 1, wherein the weight ratio of total carbohydrate to glutamine in the composition is 0.5:1 to 50:1.

14. The method of claim 1, wherein the weight ratio of total carbohydrate to glutamine is at least 4:1 in an aqueous solution, either after preparation with an aqueous solvent or after delivery in an aqueous environment of the subject.

15. The method of claim 1, wherein the composition comprises no more than 5 naturally occurring amino acids other than glutamine.

16. The method of claim 15 wherein the composition comprises no naturally occurring amino acids other than glutamine.

17. The method of claim 1, wherein the composition is administered after or while administering radiation therapy to the subject.

18. The method of claim 17 wherein the composition is administered before administration of the radiation therapy to the subject.

* * * * *

UNITED STATES PATENT AND TRADEMARK OFFICE
CERTIFICATE OF CORRECTION

| | | |
|---|---|---|
| PATENT NO. | : 7,709,529 B2 | Page 1 of 1 |
| APPLICATION NO. | : 10/633402 | |
| DATED | : May 4, 2010 | |
| INVENTOR(S) | : V. S. Klimberg et al. | |

It is certified that error appears in the above-identified patent and that said Letters Patent is hereby corrected as shown below:

On Page 2, in column 2, under "Other Publications", line 11, delete "senstivity" and insert -- sensitivity --, therefor.

On Page 3, in column 1, under "Other Publications", line 25, delete "R.adiation" and insert -- Radiation --, therefor.

On Page 3, in column 1, under "Other Publications", line 68, delete "Transpoeter" and insert -- Transporter --, therefor.

On Page 4, in column 1, under "Other Publications", line 25, delete "Commitee" and insert -- Committee --, therefor.

In column 6, line 62, delete "omithine," and insert -- ornithine, --, therefor.

In column 19, lines 23–24, delete "omithine," and insert -- ornithine, --, therefor.

In column 24, line 63, delete "repair," and insert -- repair. --, therefor.

In column 29, line 7, delete "FIG." and insert -- FIGS. --, therefor.

In column 34, line 11, delete "Fransisco," and insert -- Francisco, --, therefor.

In column 37, line 66, delete "anti-1" and insert -- anti-β --, therefor.

In column 43, line 19, delete "ION" and insert -- 10 N --, therefor.

In column 44, line 8, delete "(PBS)" and insert -- (FBS) --, therefor.

Signed and Sealed this

Twenty-second Day of June, 2010

David J. Kappos
*Director of the United States Patent and Trademark Office*